United States Patent
Patel et al.

(10) Patent No.: US 7,405,228 B2
(45) Date of Patent: *Jul. 29, 2008

(54) ANTIBACTERIAL CYANO-(SUBSTITUTED)-METHYLENEPIPERIDINOPHENYL OXAZOLIDINONES TARGETING MULTIPLE RIBONUCLEOPROTEIN SITES

(75) Inventors: Mahesh V Patel, Chikalthana Aurangabad (IN); Prasad K Deshpande, Chikalthana Aurangabad (IN); Milind D Sindkhedkar, Chikalthana Aurangabad (IN); Shrikant V Gupte, Chikalthana Aurangabad (IN); Yati Chugh, Chikalthana Aurangabad (IN); Nitin Shetty, Chikalthana Aurangabad (IN); Milind C Shukla, Chikalthana Aurangabad (IN); Ravindra D Yeole, Chikalthana Aurangabad (IN); Noel J De Souza, Chikalthana Aurangabad (IN)

(73) Assignee: Wockhardt Limited, Bandra (East) Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/616,888

(22) Filed: Jul. 10, 2003

(65) Prior Publication Data
US 2004/0063954 A1 Apr. 1, 2004

Related U.S. Application Data

(60) Provisional application No. 60/395,164, filed on Jul. 11, 2002.

(30) Foreign Application Priority Data
Apr. 21, 2003 (IN) .................... 392/MUM/2003

(51) Int. Cl.
A61K 31/421 (2006.01)
A61K 31/454 (2006.01)
C07D 413/10 (2006.01)
C07D 401/10 (2006.01)

(52) U.S. Cl. ................ 514/326; 546/209
(58) Field of Classification Search ........... 546/209; 514/326
See application file for complete search history.

(56) References Cited

U.S. PATENT DOCUMENTS

2004/0087633 A1* 5/2004 Koh et al. ............ 514/362

* cited by examiner

*Primary Examiner*—Patricia L Morris
(74) *Attorney, Agent, or Firm*—Ladas and Parry LLP

(57) ABSTRACT

The present invention provides agents having high antimicrobial activity for preventing and treating infectious diseases. Thus, the present invention provides novel cyano-(substituted)-methylenepiperidinophenyl oxazolidinone derivatives, processes for making the compounds, as well as antimicrobial compositions containing said derivatives as active ingredients and methods of treating bacterial infections with the said derivatives.

12 Claims, No Drawings

ANTIBACTERIAL CYANO-(SUBSTITUTED)-METHYLENEPIPERIDINOPHENYL OXAZOLIDINONES TARGETING MULTIPLE RIBONUCLEOPROTEIN SITES

This application claims the benefit of U.S. Provisional Application(s) No(s).: 60/395,164 Jul. 11, 2002 and incorporates the same by reference.

FIELD OF THE INVENTION

The present invention relates to the field of cyano-(substituted) methylenepiperidinophenyl oxazolidinones having antibacterial activity against Gram-positive and Gram-negative bacteria. While not being bound to any theory, it is thought that the antibacterial activity is based on the their ability to inhibit bacterial ribonucleoprotein through differential binding at single/multiple ribonucleoprotein sites. The invention also relates to processes for making the compounds, to pharmaceutical compositions containing the compounds and to methods of using the compounds including treating bacterial infections with the compounds.

BACKGROUND OF THE INVENTION

Oxazolidinones represent a novel chemical class of synthetic antimicrobial agents. Following a chequered historical development since about the early-1980s, a watershed event took place with the clinical development and release for medical use in the late 2000s of the first representative, Linezolid, of this class[1,2] This advance enabled the profiling of the unique properties of the members of this class, which is that they display activity against important Gram-positive human and veterinary pathogens including methicillin-resistant Staphylococcus aureus (MRSA), vancomycin resistant enterococci (VRE) and β-lactam resistant Streptococcus pneumoniae (PRSP). The oxazolidinones also show activity against Gram-negative aerobic bacteria and Gram-positive and Gram-negative anaerobes[3].

The deficiencies of this class of oxazolidinones have also surfaced. They are inactive against Enterobacteriaceae[4]. They are generally bacteriostatic and do not display activity at a useful level against aerobic fastidious Gram-negative pathogens, as well as Gram-negative anaerobes. Moreover their potency for atypical respiratory pathogens such as Mycoplasma pneumoniae, M. hominis, Ureaplasma urealyticium and Chlamydia species is of a borderline range which could result into unacceptable clinical efficacy for the treatment of respiratory tract infections[3].

Other limitations that have appeared through the clinical development studies and use of Linezolid and its potential successors in development are that the class has a propensity to induce myelosuppression with consequent thrombocytopenia[5]. Inhibition of monoamine oxidase by oxazolidinones has prompted a recommendation made to clinicians that clinical use of members of this class be done with caution during concomitant usage of adrenergic or serotonergic agents and selective serotonin reuptake inhibitors[6].

Linezolid is shown to have two targets in cells for its inhibitory effects. It binds to the 50S subunit within domain V of the 23S or RNA peptidyl transferase center near the interface with the 30S subunit, thereby blocking the formation of the tMet-tRNA-ribosome-mRNA ternary complex. In addition, linezolid associates with the nascent 50S particle and stops the assembly process[7].

Considering that the oxazolidinones are bacteriostatic, as indeed are most other agents that inhibit bacterial protein synthesis, there is a strong likelihood that resistance can emerge under selective pressure during therapy, specially for infections which require a bactericidal therapy to be used. The significant concern related to this class of antibacterials is attributed to this essentially bacteriostatic effect against their prime target pathogens such as staphylococci, enterococci and pneumococci. It is pertinent to quote from the Adis R&D Insight report (Document 013296 dated Dec. 27, 2001) that an oxazolidinone AZD 2563 under clinical development is described to be "ineffective against linezolid-resistant S. pneumoniae". This concern is further aggravated due to the recent reports of emergence of Linezolid-resistant strains of enterococci and staphylococci in clinics. In fact the first clinical isolates of E. faecium, E. faecalis and S. aureus resistant to linezolid have recently been described[8]. Also, resistant strains have been generated by serial passage techniques, the resistance being associated with specific mutations in the 23S rRNA gene[9].

Our own studies have also led to the identification of novel Linezolid-resistant strains, an embodiment of this invention. It has been reported that in-vitro staphylococci and enterococci resistant to linezolid can be selected only with difficulty[8], which through genome characterization studies have shown the resistance to be associated with specific mutations in the 23S rRNA nucleotide sequence. The linezolid-resistant strain of S. pneumoniae ATCC 6303 LR has guanine replacing adenine at the nucleotide position 2160 of 23S rRNA. Similarly, our Linezolid-resistant strains of S. aureus Smith & MRSA 032 have uracil replacing guanine at nucleotide position 2447. These three resistant mutants, harbouring changes in the molecular targets of linezolid, showed significant elevation of MIC values for Linezolid indicating the loss in affinity of the drug to its ribosomal targets.

"Fine tuning" of this class of agents to improve the affinity of its members for the ribosome at existing or altered single or multiple target sites is conceivable, resulting thereby in significantly increasing their potency, and in incorporating bactericidal activity against Linezolid-sensitive/-resistant strains.

The present invention describes a novel series of oxazolidinones which display increased potency, and incorporate bactericidal activity, in contrast to the earlier-described bacteriostatic activity, against Linezolid-sensitive/-resistant strains, thus indicating a differential binding at the conventional site/s of the ribonucleoprotein and/or targeting multiple such receptor sites. In addition, using comparative molecular field analysis[10], a study of literature-described oxazolidinones and the novel compounds of the present invention has enabled the identification of newer/additional structural motifs of the oxazolidinone class, novel and non-obvious from the prior art, which support the activity against the Linezolid-sensitive/-resistant pathogens. There is no prior description of oxazolidinones displaying such bactericidal activity or useful activity against Linezolid-sensitive/-resistant or other oxazolidinone-resistant microbial pathogens.

The following publications may be referred to with respect to the statements made in the above-described background information.

[1] Slee AM, et al., Antimicrob. Agents Chemother (1987) 31:1791-1797;

[2] 2nd European Congress of Chemotherapy and 7th Biennial Conference on Antiinfective Agents and Chemotherapy (Final Program), (1998): 93;

[3]Diekema D J et al., Lancet 2001; 358: 1975-82;
[4]Zhanel GG et al., Canadian Journal of Infectious Diseases, 2001, 12: 379-390;
[5]Kuter D J et al., Pharmacotherapy, 2001: 21: 1010-1030;
[6]Ament P W et al., Am Fam Physician 2002, 65: 663-70;
[7]Shinabarger D, Exp. Opin. Invest. Drugs (1999) 8:1195-1202; Champrey W S et al., Curr. Microb. 2002, 44: 350-356;
[8]Zurenko GE et al, In 39th Interscience Conference on Antimicrobial Agents and Chemotherapy, Washington DC, (1999) abstr. 848; Gonzales RD et al., Lancet 2001; 357: 1179; Tsiodras S, et al., Lancet 2001; 358: 207-08;
[9]Swaney SM et al., In 38th Interscience Conference on Antimicrobial Agents and Chemotherapy, Washington DC, (1998) abstr. C-104;
[10]Pae, A. N. et al, Bioorg. & Med. Chem. Lett., 1999, 9:2685-90.

After filing of our pending provisional U.S. application No. 60/395,164 methylenepiperidinyl and methylenepyrrolidinyl oxazolidinone antibacterial agents were described in Kim H Y et al., Bioorg. & Med. Chem. Lett., (2003), 13:2227-2230.

Information Disclosure

There are several patents cited in the literature, which refer to oxazolidinones having antibacterial activity.

WO95/25106 dated Sep. 21, 1995 discloses substituted piperidino phenyloxazolidinones. This corresponds to U.S. Pat. No. 5,668,286 and EP 0 750 618.

WO96/13502 dated May 9, 1996 discloses phenyloxazolidinones having a multisubstituted azetidinyl or pyrrolidinyl moiety.

U.S. Pat. No. 5,574,055 dated Nov. 12, 1996 discloses oxazolidinone derivatives that can be used for prevention or control of depressive, panic and anxiety states.

Other publications are as follows:

WO 99/24428 dated May 20, 1999 discloses diazepenophenyloxazolidinone derivatives.

WO01/44212 dated Jun. 21, 2001 discloses benzoic acid esters of oxazolidinones having a hydroxyacetylpiperazine substituent.

WO 02/06278 dated Jan. 24, 2002 discloses substituted aminopiperidino phenyloxazolidinone derivatives.

U.S. Pat. No. 6,358,942 dated Mar. 19, 2002 discloses phenyloxazolidinones having a C—C bond to 4-8 membered heterocyclic rings.

WO 00/21960 dated Apr. 20, 2000 discloses heterocyclicphenyl oxazolidinones having the heterocycle linked through a carbon atom to the phenyl moiety.

WO 95/07271 (U.S. Pat. No. 5,688,792 dated Nov. 18, 1997) discloses oxazolidinones containing morpholine and thiomorpholine.

The following references disclose various oxazolidinones, which have a thiocarbonyl functionality.

U.S. Pat. No. 6,387,896 dated May 14, 2002.

WO 98/54161 dated Dec. 3, 1998 (U.S. 2002/0016323A1 Feb. 7, 2002);

WO 00/27830 dated May 18, 2000.

WO 01/09107 dated Feb. 8, 2001.

The following citations pertain to oxazolidinones some of which have a cyano substituent and others of which have heterocyclic moieties incorporated in the described molecules.

U.S. Pat. No. 5,977,373 dated Nov. 2, 1999 (WO 99/02525 dated Jul. 8, 1998) discloses thiadiazolyl and oxadiazolyl phenyloxazolidinones.

U.S. Pat. No. 5,910,504 dated Jun. 8, 1999 (WO 96/23788 dated Aug. 8, 1996) discloses heteroaromatic ring substituted phenyloxazolidinones.

U.S. Pat. No. 5,547,950 dated Aug. 20, 1996 and U.S. Pat. No. 5,700,799 dated Dec 23, 1997 [WO 93/23384] disclose oxazolidinone antimicrobials containing substituted diazine moieties.

Genin M. J. et al J. Med. Chem 2000, 43,953-970

Weidner-Wells et al. Biorganic and Medicinal Chemistry Letters 2001, 11, 1829-1832.

WO 01/58885A1 dated Aug. 16, 2001 discloses oxazolidinone thioamides with piperazine amide substituents.

Ryan B. et al., Exp. Opin. Invest. Drugs (2000) 9: 2959-60 discloses an oxazolidinone that is active against linezolid-resistant S.aureus.

The compounds of the present invention are novel, none of them having being previously reported in the literature. They are non-obvious over the compounds in the prior art by virtue of their being bactericidal, in contrast to the compounds of the prior art being generally bacteriostatic. They are active against linezolid-resistant strains, in particular against novel linezolid-resistant strains of this invention, in further particular against linezolid-resistant *Streptococcus pneumoniae* and against resistant *enterococci*, such activity features being disclosed here for the first time. There is no previous report of oxazolidinones of the structure presented in this invention which display activity against difficult-to-obtain linezolid-resistant strains. While not being bound by any theory, it is surmised by displaying such activity against linezolid-resistant strains, the compounds of the invention for the first time thus establish their ability to inhibit bacterial ribonucleoprotein through differential binding at single/multiple sites.

In addition, a Comparative Molecular Field Analysis (CoMFA), 3-dimensional quantitative structure activity relationship study, as described in more detail later in this specification, shows that in contrast to the prior art, which teaches that the electrostatic contributions play a more predominant role than the steric contributions, the compounds of the present invention require a comparatively higher steric contribution, more than one and a half times over the electrostatic contributions.

SUMMARY OF THE INVENTION

The present invention provides new compounds of the Formula I.

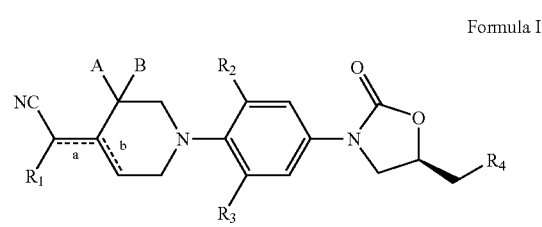

Formula I or pharmaceutical acceptable salts thereof, wherein

"a" represents a single bond or a double bond

"b" represents a single bond or a double bond

"a" and "b" cannot both be double bonds at the same time.

"A" and "B" are each and independently selected from H, $C_1$-$C_6$ alkyl, $CO_2Et$, or halogen.

When "a" is a double bond or "a" is a single bond and "A" is not H, CH$_3$, CO$_2$Et, or F R$_1$ is, H, alkyl, substituted alkyl, alkenyl, alkynyl, cycloalkyl, substituted cycloalkyl, alkanoyl, substituted alkanoyl, aralkanoyl, substituted aralkanoyl, alkoxycarbonyl, substituted alkoxycarbonyl, thioacyl, substituted thioacyl, aroyl, substituted aroyl, alkylmercapto, arylmercapto, heterocyclylcarbonyl, heterocyclylthiocarbonyl, aralkyl, aryl, substituted aryl, heterocyclyl, substituted herocyclyl, heteroaryl, substituted heteroaryl, cyano, carboxylic acid, carboxamido, amino, substituted amino, or halogen.

When "a" is a single bond and "A" is H, CH$_3$,CO$_2$Et, or F, then; R$_1$ is alkenyl, alkynyl, cycloalkyl, substituted cycloalkyl, alkanoyl, substituted alkanoyl, aralkanoyl, substituted aralkanoyl, alkoxycarbonyl, substituted alkoxycarbonyl, thioacyl, substituted thioacyl, aroyl, substituted aroyl, alkylmercapto, arylmercapto, heterocyclylcarbonyl, heterocyclylthiocarbonyl, aralkyl, aryl, substituted aryl, heterocyclyl, substituted herocyclyl, heteroaryl, substituted heteroaryl or carboxamido. R$_2$ and R$_3$ are the same or different and are hydrogen or halo;

R$_4$ is,

C$_1$-C$_6$ alkylsulphonyloxy, arylsulphonyloxy, amino, mono or di substituted amino, azido, nitrilo, substituted nitrilo, aminonitrilo, isocynato, formamido, C$_1$-C$_6$ alkyl amido, substituted C$_1$-C$_6$ alkyl amido, C$_1$-C$_6$ alkyl thiocarbonylamino, substituted C$_1$-C$_6$ alkyl thiocarbonylamino, sulphonamido, substituted sulphonamido, pthalamido, carbamato, substituted carbamato, ureido, substituited ureido, five to six membered heterocyclyl, or substituted five to six membered heterocyclyl.

In another aspect, the present invention also provides:

a pharmaceutical composition comprising a compound of Formula I or a pharmaceutically acceptable salt thereof, and a pharmaceutically acceptable carrier, a method for treating Gram-positive microbial infections in human or other warm-blooded animals by administering to the subject in need thereof a therapeutically effective amount of a compound of Formula I or a pharmaceutically acceptable salt thereof, a method for treating Gram-negative microbial infections in human or other warm-blooded animals by administering to the subject in need a therapeutically effective amount of a compound of Formula I or a pharmaceutically acceptable salt thereof.

The invention also includes novel intermediates and processes that are used to prepare compounds of Formula I.

DETAILED DESCRIPTION OF THE INVENTION

The present invention provides new compounds of the Formula I.

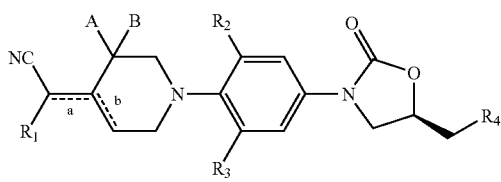

Formula I or pharmaceutical acceptable salts thereof, wherein

"a" represents a single bond or a double bond; and

"b" represents a single bond or a double bond.

"a" and "b" cannot both be double bonds at the same time.

"A" and "B" are each and independently selected from H, C$_1$-C$_6$ alkyl, CO$_2$Et, or halogen.

When "a" is a double bond or "a" is a single bond and "A" is not H, CH$_3$, CO$_2$Et or F, then R$_1$ is, H, alkyl, substituted alkyl, alkenyl, alkynyl, cycloalkyl, substituted cycloalkyl, alkanoyl, substituted alkanoyl, aralkanoyl, substituted aralkanoyl, alkoxycarbonyl, substituted alkoxycarbonyl, thioacyl, substituted thioacyl, aroyl, substituted aroyl, alkylmercapto, arylmercapto, heterocyclylcarbonyl, heterocyclylthiocarbonyl, aralkyl, aryl, substituted aryl, heterocyclyl, substituted herocyclyl, heteroaryl, substituted heteroaryl, cyano, carboxylic acid, carboxamido, amino, substituted amino, or halogen.

When "a" is a single bond and "A" is H, CH$_3$,CO$_2$Et, or F, then; R$_1$ is alkenyl, alkynyl, cycloalkyl, substituted cycloalkyl, alkanoyl, substituted alkanoyl, aralkanoyl, substituted aralkanoyl, alkoxycarbonyl, substituted alkoxycarbonyl, thioacyl, substituted thioacyl, aroyl, substituted aroyl, alkylmercapto, arylmercapto, heterocyclylcarbonyl, heterocyclylthiocarbonyl, aralkyl, aryl, substituted aryl, heterocyclyl, substituted herocyclyl, heteroaryl, substituted heteroaryl or carboxamido. R$_2$ and R$_3$ are the same or different and are hydrogen or halo;

R$_4$ is,

C$_1$-C$_6$ alkylsulphonyloxy, arylsulphonyloxy, amino, mono or di substituted amino, azido, nitrilo, substituted nitrilo, aminonitrilo, isocynato, formamido, C$_1$-C$_6$ alkyl amido, substituted C$_1$-C$_6$ alkyl amido, C$_1$-C$_6$ alkyl thiocarbonylamino, substituted C$_1$-C$_6$ alkyl thiocarbonylamino, sulphonamido, substituted sulphonamido, pthalamido, carbamato, substituted carbamato, ureido, substituited ureido, five to six membered heterocyclyl, or substituted five to six membered heterocyclyl.

"Alkyl" means carbon atom chains having C$_1$-C$_6$ number of carbon atoms which can be either straight chain or branched such as methyl, ethyl, propyl, butyl, pentyl, or hexyl.

"Substituted alkyl" means C$_1$-C$_6$ alkyl, straight chain or branched, bearing substituents like one or more aryl, hydroxy, substituted hydroxy for example methanesulphonyloxy, heterocyclyl, substituted heterocycyl, cyano, halo, for example fluorine or chlorine, amino, substituted amino.

"Alkenyl" means carbon atom chains having C$_2$-C$_6$ number of carbon atoms which can be either straight chain or branched such as ethene, propene, butene, pentene, hexene, butadiene, or hexadiene.

"Alkynyl" means carbon atom chains having C$_2$-C$_6$ number of carbon atoms which can be either straight chain or branched such as ethyne, propyne, butyne, pentyne, hexyne, butadiyne, or hexadiyne.

"Cycloalkyl" means C$_3$-C$_6$ carbocycles such as cyclopropyl, cyclobutyl, cyclopentyl, or cyclohexyl.

"Substituted cycloalkyl" means cycloalkyl substituted with a groups such as alkyl, hydroxyl, amino, substituted amino, alkoxycarbonyl, carboxamido, cyano or halogen.

"Alkanoyl" means C$_1$-C$_6$ number of carbon atoms to form an organic acid where the OH group has been deleted, such as formyl, HCO—; acetyl, or CH$_3$CO—.

"Substituted alkanoyl" means alkanoyl bearing substitutents like one or more alkyl, hydroxyl, amino, substituted amino, alkoxycarbonyl, carboxamido, cyano, or halogen.

"Aralkanoyl" means $C_1$-$C_6$ number of carbon atoms to form an aralkyl organic acid where the OH group has been deleted, such as phenylacetyl, $C_6H_5CH_2CO$—.

"Substituted aralkanoyl" means aralkanoyl bearing substitutents like one or more alkyl, hydroxyl, amino, substituted amino, alkoxycarbonyl, carboxamido, cyano, or halogen.

"Alkoxycarbonyl" means alkanoyl group substituted with alkyl ether such as methoxy, ethoxy, propyloxy so on.

"Substituted alkoxycarbonyl" means alkoxycarbonyl bearing substitutents like one or more alkyl, hydroxyl, amino, substituted amino, alkoxycarbonyl, carboxamido, cyano, or halogen.

"Thioacyl" means $C_1$-$C_6$ number of carbon atoms to form an thioorganic acid where the OH group has been deleted, such as thioformyl, HCS—; thioacetyl, $CH_3CS$—.

"Substituted thioacyl" means thioacyl bearing substitutents like one or more alkyl, hydroxyl, amino, substituted amino, alkoxycarbonyl, carboxamido, cyano, halogen.

"Aroyl" means $C_1$-$C_6$ number of carbon atoms to form an aryl organic acid where the OH group has been deleted, such as benzoyl, $C_6H_5CO$—.

"Substituted aroyl" means alkanoyl bearing substitutents like one or more alkyl, hydroxyl, amino, substituted amino, alkoxycarbonyl, carboxamido, cyano, halogen.

"Alkylmercapto" means alkylthiol in which H group is deleted such as $CH_3S$—, $C_2H_5S$— so on.

"Arylmercapto" means arylthiol in which H group is deleted such as $C_6H_5S$— so on.

"Heterocyclylcarbonyl" means groups such as carbonyl bearing heterocycles like morpholine, piperidine, piperazine and so on.

"Heterocyclylthiocarbonyl" means groups such as thiocarbonyl bearing heterocycles like morpholine, piperidine, piperazine and so on.

"Aralkyl" are groups such as benzyl, benzhydryl, trityl and so on.

"Aryl" stands for phenyl, naphthyl, so on.

"Substituted aryl" stands for aryl which may optionally be substituted with groups such as like one or more alkyl, hydroxyl, amino, substituted amino, alkoxycarbonyl, carboxamido, cyano, halogen.

"Heterocyclyl" means groups such as heterocycles like morpholine, piperidine, piperazine and so on.

"Substituted heterocyclyl" stands for herterocyclyl which may optionally be substituted with groups such as like one or more alkyl, alkoxycarbonyl, carboxamido, cyano, halogen.

"Heteroaryl" means groups such as heterocycles like pyrrole, furane, thiophene, pyrazole, imidazole, trizole, tetrazole, thiazole, pyridine, pyrimidine, and so on.

"Substituted heteroaryl" stands for herteroaryl which may optionally be substituted with groups such as like one or more alkyl, alkoxycarbonyl, carboxamido, cyano, halogen.

"Cyano" is —CN.

Carboxamido is —$CONH_2$.

"Substituted amino" stands for $NH_2$, in which one or more hydrogen atoms may be optionally substituted by $C_1$-$C_3$ alkyl groups also unsubstituted or optionally substituted by substituents as defined earlier in the specification under "substituted alkyl".

"Halogen" means atoms such as fluorine, chlorine, bromine, iodine. and pharmnaceutically acceptable salts thereof including isomers, polymorphs or pharmaceutical acceptable salts thereof.

Preferred salts are those of hydrochloride, hydrobronide, hydroiodide, sulphate, phosphate and salts of organic acids such as acetate, lactate, succinate, oxalate, maleate, fumarate, malate, tatrate, citrate, ascorbate, cinnamate, gluconate, benzoate, methane sulfonate and p-toluene sulfonate; lithium, sodium, magnesium, calcium and potassium salts, and amino acids salts such as alanine, arginine, asparagine, aspartic acid, cysteine, glutamine, glutamic acid, glycine, histidine, isoleucine, leucine, lysine, methionine, phenylalanine, proline, serine, threonine, tryptopham tyrosine or valine.

More particularly, the present invention currently provides compounds of Formula I, which can be represented as Formulae II, III and IV.

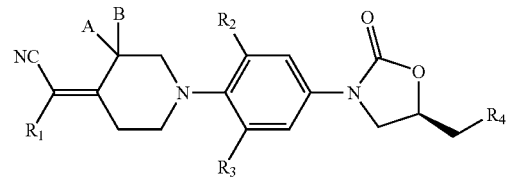

Formula II

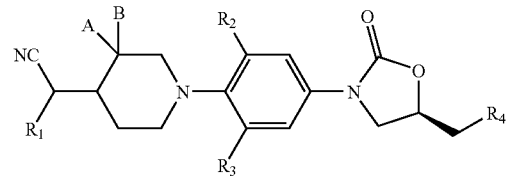

Formula III

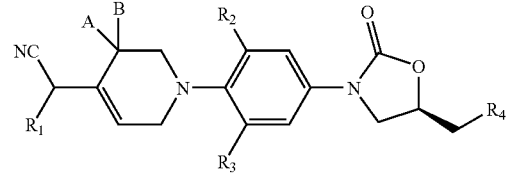

Formula IV wherein,
preferably A, B, $R_1$, and $R_2$, $R_3$ and $R_4$ are as defined above.

Preferred Compounds

Some preferred examples of the oxazolidinone derivatives represented by the general Formnula I and belonging to the subclass Formula II are as follows:

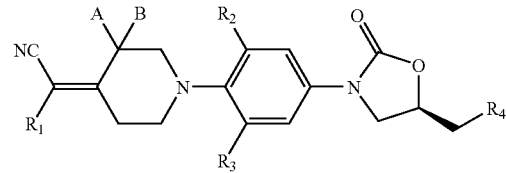

Formula II 1. (S)-{3-[4-(4-cyanomethylidene-piperidin-1-yl)-phenyl]-2-oxo-oxazolidin-5-ylmethyl}-azide;
2. (S)-N-{3-[4-(4-cyanomethylidene-piperidin-1-yl)-phenyl]-2-oxo-oxazolidin-5-ylmethyl}-formamide;
3. (S)-N-{3-[4-(4-cyanomethylidene-piperidin-1-yl)-phenyl]-2-oxo-oxazolidin-5-ylmethyl}-acetamide;
4. (S)-1-{3-[4-(4-cyanomethylidene-piperidin-1-yl)-phenyl]-2-oxo-oxazolidin-5-ylmethyl}-4-carboxyethyl-1,2,3-triazole;

5. (S)-1-{3-[4-(4-cyanomethylidene-piperidin-1-yl)-phenyl]-2-oxo-oxazolidin-5-ylmethyl}-4-cyano-1,2,3-triazole;
6. (R)-{3-[4-(4-cyanomethylidene-piperidin-1-yl)-phenyl]-2-oxo-oxazolidin-5-ylmethyl}-methanesulphonate;
7. (S)-N-{3-[4-(4-cyanomethylidene-piperidin-1-yl)-3-fluorophenyl]-2-oxo-oxazolidin-5-ylmethyl}-isocynate;
8. (S)-N-{3-[4-(4-cyanomethylidene-piperidin-1-yl)-3-fluorophenyl]-2-oxo-oxazolidin-5-ylmethyl}-formamide;
9. (S)-N-{3-[4-(4-cyanomethylidene-piperidin-1-yl)-3-fluorophenyl]-2-oxo-oxazolidin-5-ylmethyl}-acetamide;
10. (S)-N-{3-[4-(4-cyanomethylidene-piperidin-1-yl)-3-fluorophenyl]-2-oxo-oxazolidin-5-ylmethyl}-propionamide;
11. (S)-N-{3-[4-(4-cyanomethylidene-piperidin-1-yl)-3-fluorophenyl]-2-oxo-oxazolidin-5-ylmethyl}-2-dimethylpropionamide;
12. (S)-N-{3-[4-(4-cyanomethylidene-piperidin-1-yl)-3-fluorophenyl]-2-oxo-oxazolidin-5-ylmethyl}-3-dimethylbutanamide;
13. (S)-N-{3-[4-(4-cyanomethylidene-piperidin-1-yl)-3-fluorophenyl]-2-oxo-oxazolidin-5-ylmethyl}-2-hydroxyacetamide;
14. (S)-N-{3-[4-(4-cyanomethylidene-piperidin-1-yl)-3-fluorophenyl]-2-oxo-oxazolidin-5-ylmethyl}-2-pivolyloxyacetamide;
15. (S)-N-{3-[4-(4-cyanomethylidene-piperidin-1-yl)-3-fluorophenyl]-2-oxo-oxazolidin-5-ylmethyl}-N-methylacetamide;
16. (S)-{3-[4-(4-cyanomethylidene-piperidin-1-yl)-3-fluorophenyl]-2-oxo-oxazolidin-5-ylmethyl}-azide;
17. (S)-{3-[4-(4-cyanomethylidene-piperidin-1-yl)-3-fluorophenyl]-2-oxo-oxazolidin-5-ylmethyl}-amine;
18. (S)-{3-[4-(4-cyanomethylidene-piperidin-1-yl)-3-fluorophenyl]-2-oxo-oxazolidin-5-ylmethylamino}-prop-2-ene;
19. (S)-{3-[4-(4-cyanomethylidene-piperidin-1-yl)-3-fluorophenyl]-2-oxo-oxazolidin-5-ylmethylamino}-nitrile;
20. (S)-{3-[4-(4-cyanomethylidene-piperidin-1-yl)-3-fluorophenyl]-2-oxo-oxazolidin-5-ylmethylamino}-acetonitrile;
21. (S)-{3-[4-(4-cyanomethylidene-piperidin-1-yl)-3-fluorophenyl]-2-oxo-oxazolidin-5-ylmethylamino}-methylamine;
22. (S)-{N-{3-[4-(4-cyanomethylidene-piperidin-1-yl)-3-fluorophenyl]-2-oxo-oxazolidin-5-ylmethylamino}N-cyano}-prop-2-ene;
23. (S)-N-{3-[4-(4-cyanomethylidene-piperidin-1-yl)-3-fluorophenyl]-2-oxo-oxazolidin-5-ylmethyl}-2-cyanoacetamide;
24. (S)-N-{3-[4-(4-cyanomethylidene-piperidin-1-yl)-3-fluorophenyl]-2-oxo-oxazolidin-5-ylmethyl}-2-oxo-oxazolidin-4-yl-carboxamide;
25. (S)-N-{3-[4-(4-cyanomethylidene-piperidin-1-yl)-3-fluorophenyl]-2-oxo-oxazolidin-5-ylmethyl}-pyrrolidin-2-carboxamide;
26. (S)-1-{3-[4-(4-cyanomethylidene-piperidin-1-yl)-3-fluorophenyl]-2-oxo-oxazolidin-5-ylmethyl}-4-carboethoxy-1,2,3-triazole;
27. (S)-1-{3-[4-(4-cyanomethylidene-piperidin-1-yl)-3-fluorophenyl]-2-oxo-oxazolidin-5-ylmethyl}-5-carboethoxy-1,2,3-triazole;
28. (S)-1-{3-[4-(4-cyanomethylidene-piperidin-1-yl)-3-fluorophenyl]-2-oxo-oxazolidin-5-ylmethyl}-4-cyano-1,2,3-triazole;
29. (S)-N-{3-[4-(4-cyanomethylidene-piperidin-1-yl)-3-fluorophenyl]-2-oxo-oxazolidin-5-ylmethyl}-difluoroacetamide;
30. (S)-N-{3-[4-(4-cyanomethylidene-piperidin-1-yl)-3-fluorophenyl]-2-oxo-oxazolidin-5-ylmethyl}-trifluoroacetamide;
31. (S)-N-{3-[4-(4-cyanomethylidene-piperidin-1-yl)-3-fluorophenyl]-2-oxo-oxazolidin-5-ylmethyl}-chloroacetamide;
32. (S)-N-{3-[4-(4-cyanomethylidene-piperidin-1-yl)-3-fluorophenyl]-2-oxo-oxazolidin-5-ylmethyl}-dichloroacetamide;
33. (S)-N-{3-[4-(4-cyanomethylidene-piperidin-1-yl)-3-fluorophenyl]-2-oxo-oxazolidin-5-ylmethyl}-trichloroacetamide;
34. (S)-N-{3-[4-(4-cyanomethylidene-piperidin-1-yl)-3-fluorophenyl]-2-oxo-oxazolidin-5-ylmethyl}-bromoacetamide;
35. (S)-N-{3-[4-(4-cyanomethylidene-piperidin-1-yl)-3-fluorophenyl]-2-oxo-oxazolidin-5-ylmethyl}-dibromoacetamide;
36. (S)-N-{3-[4-(4-cyanomethylidene-piperidin-1-yl)-3-fluorophenyl]-2-oxo-oxazolidin-5-ylmethyl}-iodoacetamide;
37. (S)-N-{3-[4-(4-cyanomethylidene-piperidin-1-yl)-3-fluorophenyl]-2-oxo-oxazolidin-5-ylmethyl}-4-methylphenylsulphonamide;
38. (S)-N-{3-[4-(4-cyanomethylidene-piperidin-1-yl)-3-fluorophenyl]-2-oxo-oxazolidin-5-ylmethyl}-methylcarbamate;
39. (S)-N-{3-[4-(4-cyanomethylidene-piperidin-1-yl)-3-fluorophenyl]-2-oxo-oxazolidin-5-ylmethyl}-ethylcarbamate;
40. (S)-N-{3-[4-(4-cyanomethylidene-piperidin-1-yl)-3-fluorophenyl]-2-oxo-oxazolidin-5-ylmethyl}-isopropylcarbamate;
41. (2S,5S)-{N-{3-[4-(4-cyanomethylidene-piperidin-1-yl)-3-fluorophenyl]-2-oxo-oxazolidin-5-ylmethyl}-propionamid-2-yl}-amine;
42. (2S,5S)-{N-{3-[4-(4-cyanomethylidene-piperidin-1-yl)-3-fluorophenyl]-2-oxo-oxazolidin-5-ylmethyl}-3-hydroxypropionamid-2-yl}-amine;
43. (2S,5S)-{N-{3-[4-(4-cyanomethylidene-piperidin-1-yl)-3-fluorophenyl]-2-oxo-oxazolidin-5-ylmethyl}-3-(imidazol-4-yl)-propionamid-2-yl}-amine;
44. (S)-N-{3-[4-(4-cyanomethylidene-piperidin-1-yl)-3-fluorophenyl]-2-oxo-oxazolidin-5-ylmethyl}-1-pthalamide;
45. (S)-N-{3-[4-(4-cyanomethylidene-piperidin-1-yl)-3-fluorophenyl]-2-oxo-oxazolidin-5-ylmethyl}-thioacetamide;
46. (S)-N-{3-[4-(4-cyanomethylidene-piperidin-1-yl)-3-fluorophenyl]-2-oxo-oxazolidin-5-ylmethyl}-methylthiocarbamate;
47. (S)-N-{3-[4-(4-cyanomethylidene-piperidin-1-yl)-3-fluorophenyl]-2-oxo-oxazolidin-5-ylmethyl}-2-hydroxythioacetamide;
48. (S)-N-{3-[4-(4-cyanomethylidene-piperidin-1-yl)-3-fluorophenyl]-2-oxo-oxazolidin-5-ylmethyl}-2-hydroxyethylthiocarbamide;
49. (S)-N-{3-[4-(4-cyanomethylidene-piperidin-1-yl)-3-fluorophenyl]-2-oxo-oxazolidin-5-ylmethylamino}-thiocarbonylmethylamine;
50. (S)-N-{3-[4-(4-cyanomethylidene-piperidin-1-yl)-3-fluorophenyl]-2-oxo-oxazolidin-5-ylmethyl}-2-dimethylaminoethylthiocarbamide;

51. (S)-N-{3-[4-(4-cyanomethylidene-piperidin-1-yl)-3-fluorophenyl]-2-oxo-oxazolidin-5-ylmethyl}-thiocarbamide;
52. (S)-N-{3-[4-(4-cyanomethylidene-piperidin-1-yl)-3-fluorophenyl]-2-oxo-oxazolidin-5-ylmethyl}-methylthiocarbamide;
53. (S)-N-{3-[4-(4-cyanomethylidene-piperidin-1-yl)-3-fluorophenyl]-2-oxo-oxazolidin-5-ylmethyl}-methanesulphonamide;
54. (R)-{3-[4-(4-cyanomethylidene-piperidin-1-yl)-3-fluorophenyl]-2-oxo-oxazolidin-5-ylmethyl}-methanesulphonate;
55. (S)-N-{3-[4-(4-cyanomethylidene-3-fluoropiperidin-1-yl)-phenyl]-2-oxo-oxazolidin-5-ylmethyl}-acetamide;
56. (S)-N-{3-[4-(4-cyanomethylidene-3-fluoropiperidin-1-yl)-3-fluorophenyl]-2-oxo-oxazolidin-5-ylmethyl}-acetamide;
57. (S)-N-{3-[4-(4-cyanomethylidene-3-fluoropiperidin-1-yl)-3-fluorophenyl]-2-oxo-oxazolidin-5-ylmethyl}-difluoroacetamide;
58. (S)-N-{3-[4-(4-cyanomethylidene-3-fluoropiperidin-1-yl)-3-fluorophenyl]-2-oxo-oxazolidin-5-ylmethyl}-isobutylcarbamate;
59. (R)-{3-[4-(4-cyanomethylidene-3-fluoropiperidin-1-yl)-3-fluorophenyl]-2-oxo-oxazolidin-5-ylmethyl}-methanesulphonate;
60. (S)-N-{3-[4-(4-cyanomethylidene-3-fluoropiperidin-1-yl)-3-fluorophenyl]-2-oxo-oxazolidin-5-ylmethyl}-thioacetamide;
61. (S)-N-{3-[4-(4-cyanomethylidene-3,3-difluoropiperidin-1-yl)-phenyl]-2-oxo-oxazolidin-5-ylmethyl}-acetamide;
62. (S)-N-{3-[4-(4-cyanomethylidene-3-methylpiperidin-1-yl)-3-fluorophenyl]-2-oxo-oxazolidin-5-ylmethyl}-formamide;
63. (S)-N-{3-[4-(4-cyanomethylidene-3-methylpiperidin-1-yl)-3-fluorophenyl]-2-oxo-oxazolidin-5-ylmethyl}-acetamide;
64. (S)-N-{3-[4-(4-cyanomethylidene-3-methylpiperidin-1-yl)-3-fluorophenyl]-2-oxo-oxazolidin-5-ylmethyl}-trifluoroacetamide;
65. (S)-N-{3-[4-(4-cyanomethylidene-3-methylpiperidin-1-yl)-3-fluorophenyl]-2-oxo-oxazolidin-5-ylmethyl}-2-cyanoacetamide;
66. (S)-2-{3-[4-(4-cyanomethylidene-3-methylpiperidin-1-yl)-3-fluorophenyl]-2-oxo-oxazolidin-5-ylmethylamino}-1,3-thiazole;
67. (S)-N-{3-[4-(4-cyanomethylidene-3-methylpiperidin-1-yl)-3-fluorophenyl]-2-oxo-oxazolidin-5-ylmethyl}-methylthiocarbamate;
68. (S)-N-{3-[4-(4-cyanomethylidene-3-methylpiperidin-1-yl)-3-fluorophenyl]-2-oxo-oxazolidin-5-ylmethyl}-thiocarbamide;
69. (S)-N-{3-[4-(4-cyanomethylidene-3-methylpiperidin-1-yl)-3-fluorophenyl]-2-oxo-oxazolidin-5-ylmethyl}-methylthiocarbamide;
70. (S)-N-{3-[4-(4-cyanomethylidene-3,3-dimethylpiperidin-1-yl)-3-fluorophenyl]-2-oxo-oxazolidin-5-ylmethyl}-acetamide;
71. (R)-{3-[4-(4-cyanomethylidene-3,3-dimethylpiperidin-1-yl)-3-fluorophenyl]-2-oxo-oxazolidin-5-ylmethyl}-methanesulphonate;
72. (S)-N-{3-[4-(4-(1-cyanoethylidene)-piperidin-1-yl)-phenyl]-2-oxo-oxazolidin-5-ylmethyl}-acetamide;
73. (S)-N-{3-[4-(4-(1-cyanoethylidene)-piperidin-1-yl)-3-fluorophenyl]-2-oxo-oxazolidin-5-ylmethyl}-formamide;
74. (S)-N-{3-[4-(4-(1-cyanoethylidene)-piperidin-1-yl)-3-fluorophenyl]-2-oxo-oxazolidin-5-ylmethyl}-acetamide;
75. (S)-N-{3-[4-(4-(1-cyanoethylidene)-piperidin-1-yl)-3-fluorophenyl]-2-oxo-oxazolidin-5-ylmethyl}-2-cyanoacetamide;
76. (S)-N-{3-[4-(4-(1-cyanoethylidene)-piperidin-1-yl)-3-fluorophenyl]-2-oxo-oxazolidin-5-ylmethylamino}-carboxymethylamine;
77. (S)-N-{3-[4-(4-(1-cyanoethylidene)-piperidin-1-yl)-3-fluorophenyl]-2-oxo-oxazolidin-5-ylmethyl}-difluoroacetamide;
78. (S)-N-{3-[4-(4-(1-cyanoethylidene)-piperidin-1-yl)-3-fluorophenyl]-2-oxo-oxazolidin-5-ylmethyl}-chloroacetamide;
79. (S)-N-{3-[4-(4-(1-cyanoethylidene)-piperidin-1-yl)-3-fluorophenyl]-2-oxo-oxazolidin-5-ylmethyl}-dichloroacetamide;
80. (S)-N-{3-[4-(4-(1-cyanoethylidene)-piperidin-1-yl)-3-fluorophenyl]-2-oxo-oxazolidin-5-ylmethyl}-trichloroacetamide;
81. (S)-N-{3-[4-(4-(1-cyanoethylidene)-piperidin-1-yl)-3-fluorophenyl]-2-oxo-oxazolidin-5-ylmethyl}-isobutylcarbamate;
82. (R)-{3-[4-(4-(1-cyanoethylidene)-piperidin-1-yl)-3-fluorophenyl]-2-oxo-oxazolidin-5-ylmethyl}-alcohol;
83. (R)-3-{3-[4-(4-(1-cyanoethylidene)-piperidin-1-yl)-3-fluorophenyl]-2-oxo-oxazolidin-5-ylmethyloxy}-iso-oxazole;
84. (S)-N-{3-[4-(4-(1-cyanoethylidene)-piperidin-1-yl)-3-fluorophenyl]-2-oxo-oxazolidin-5-ylmethyl}-thioacetamide;
85. E/Z mixture of (S)-N-{3-[4-(4-(1-cyanoethylidene)-3-fluoropiperidin-1-yl)-3-fluorophenyl]-2-oxo-oxazolidin-5-ylmethyl}-acetamide;
86. E-(S)-N-{3-[4-(4-(1-cyanoethylidene)-3-fluoropiperidin-1-yl)-3-fluorophenyl]-2-oxo-oxazolidin-5-ylmethyl}-acetamide;
87. Z-(S)-N-{3-[4-(4-(1-cyanoethylidene)-3-fluoropiperidin-1-yl)-3-fluorophenyl]-2-oxo-oxazolidin-5-ylmethyl}-acetamide;
88. (S)-N-{3-[4-(4-(1-cyanopropylidene)-piperidin-1-yl)-phenyl]-2-oxo-oxazolidin-5-ylmethyl}-acetamide;
89. (S)-N-{3-[4-(4-(1-cyanopropylidene)-piperidin-1-yl)-3-fluorophenyl]-2-oxo-oxazolidin-5-ylmethyl}-acetamide;
90. (S)-N-{3-[4-(4-(1-cyanopropylidene)-piperidin-1-yl)-3-fluorophenyl]-2-oxo-oxazolidin-5-ylmethyl}-dichloroacetamide;
91. (S)-N-{3-[4-(4-(1-cyanopropylidene)-piperidin-1-yl)-3-fluorophenyl]-2-oxo-oxazolidin-5-ylmethyl}-trichloroacetamide;
92. (S)-N-{3-[4-(4-(1-cyanopropylidene)-piperidin-1-yl)-3-fluorophenyl]-2-oxo-oxazolidin-5-ylmethyl}-bromoacetamide;
93. (S)-N-{3-[4-(4-(1-cyanopropylidene)-piperidin-1-yl)-3-fluorophenyl]-2-oxo-oxazolidin-5-ylmethyl}-thioacetamide;
94. (S)-N-{3-[4-(4-(1-cyano-cyclopropylmethylidene)-piperidin-1-yl)-3-fluorophenyl]-2-oxo-oxazolidin-5-ylmethyl}-acetamide;
95. (S)-N-{3-[4-(4-(1-cyano-3-ene-butylidene)-piperidin-1-yl)-3-fluorophenyl]-2-oxo-oxazolidin-5-ylmethyl}-acetamide;
96. (S)-N-{3-[4-(4-(1-cyano-3-yne-butylidene)-piperidin-1-yl)-3-fluorophenyl]-2-oxo-oxazolidin-5-ylmethyl}-acetamide;

97. (S)-N-{3-[4-(4-(1-cyano-2-phenyl-ethylidene)-piperidin-1-yl)-3-fluorophenyl]-2-oxo-oxazolidin-5-ylmethyl}-acetamide;
98. (S)-N-{3-[4-(4-(1-cyano-1-phenyl-methylidene)-piperidin-1-yl)-3-fluorophenyl]-2-oxo-oxazolidin-5-ylmethyl}-acetamide;
99. (S)-N-{3-[4-(4-(1-cyano-1-(3,4-difluorophenyl))-methylidene)-piperidin-1-yl)-3-fluorophenyl]-2-oxo-oxazolidin-5-ylmethyl}-acetamide;
100. (S)-N-{3-[4-(4-(1-cyano-1-(pyridin-2-yl)-methylidene)-piperidin-1-yl)-3-fluorophenyl]-2-oxo-oxazolidin-5-ylmethyl}-acetamide;
101. (S)-N-{3-[4-(4-(1-cyano-2-(morpholin-1-yl)-ethylidene)-piperidin-1-yl)-3-fluorophenyl]-2-oxo-oxazolidin-5-ylmethyl}-acetamide;
102. (S)-N-{3-[4-(4-(1-cyano-1-(imidazol-1-yl)-methylidene)-piperidin-1-yl)-3-fluorophenyl]-2-oxo-oxazolidin-5-ylmethyl}-acetamide;
103. (S)-N-{3-[4-(4-(1-cyano-1-(2-methyl-imidazol-1-yl))-methylidene)-piperidin-1-yl)-3-fluorophenyl]-2-oxo-oxazolidin-5-ylmethyl}-acetamide;
104. (S)-N-{3-[4-(4-(1-cyano-1-(1,2,4-triazol-1-yl)-methylidene)-piperidin-1-yl)-3-fluorophenyl]-2-oxo-oxazolidin-5-ylmethyl}-acetamide;
105. (S)-N-{3-[4-(4-(1-cyano-1-(thiophen-2-yl)-methylidene)-piperidin-1-yl)-3-fluorophenyl]-2-oxo-oxazolidin-5-ylmethyl}-acetamide;
106. (S)-N-{3-[4-(4-(1,1-dicyano-methylidene)-piperidin-1-yl)-3-fluorophenyl]-2-oxo-oxazolidin-5-ylmethyl}-acetamide;
107. (S)-N-{3-[4-(4-(1-cyano-1-carboxamido-methylidene)-piperidin-1-yl)-3-fluorophenyl]-2-oxo-oxazolidin-5-ylmethyl}-acetamide;
108. (S)-N-{3-[4-(4-(1-cyano-1-(N-prop-2-ene-carboxamido)-methylidene)-piperidin-1-yl)-3-fluorophenyl]-2-oxo-oxazolidin-5-ylmethyl}-acetamide;
109. (S)-N-{3-[4-(4-(1-cyano-1-(N-cyclopropyl-carboxamido)-methylidene)-piperidin-1-yl)-3-fluorophenyl]-2-oxo-oxazolidin-5-ylmethyl}-acetamide;
110. (S)-N-{3-[4-(4-(1-cyano-1-(N-cyclohexyl-carboxamido)-methylidene)-piperidin-1-yl)-3-fluorophenyl]-2-oxo-oxazolidin-5-ylmethyl}-acetamide;
111. (S)-N-{3-[4-(4-(1-cyano-1-(pyrrolidin-1-yl-carbonyl)-methylidene)-piperidin-1-yl)-3-fluorophenyl]-2-oxo-oxazolidin-5-ylmethyl}-acetamide;
112. (S)-N-{3-[4-(4-(1-cyano-1-(morpholin-1-yl-carbonyl)-methylidene)-piperidin-1-yl)-3-fluorophenyl]-2-oxo-oxazolidin-5-ylmethyl}-acetamide;
113. (S)-N-{3-[4-(4-(1-cyano-3-hydroxy-propylidene)-piperidin-1-yl)-3-fluorophenyl]-2-oxo-oxazolidin-5-ylmethyl}-acetamide;
114. (S)-N-{3-[4-(4-(1-cyano-1-ethoxycarbonyl-methylidene)-piperidin-1-yl)-3-fluorophenyl]-2-oxo-oxazolidin-5-ylmethyl}-acetamide;
115. (S)-N-{3-[4-(4-(1-cyano-1-methylmercapto-methylidene)-piperidin-1-yl)-3-fluorophenyl]-2-oxo-oxazolidin-5-ylmethyl}-acetamide;
116. (S)-N-{3-[4-(4-(1-cyano-1-phenylmercapto-methylidene)-piperidin-1-yl)-3-fluorophenyl]-2-oxo-oxazolidin-5-ylmethyl}-acetamide;
117. (S)-N-{3-[4-(4-(1-cyano-1-bromo-methylidene)-piperidin-1-yl)-3-fluorophenyl]-2-oxo-oxazolidin-5-ylmethyl}-acetamide;
118. (S)-N-{3-[4-(4-(1-cyano-1-(pyridin-2-yl)-methylidene)-piperidin-1-yl)-3-fluorophenyl]-2-oxo-oxazolidin-5-ylmethyl}-thioacetamide;
119. (S)-N-{3-[4-(4-(1,1-dicyano-methylidene)-piperidin-1-yl)-3-fluorophenyl]-2-oxo-oxazolidin-5-ylmethyl}-thioacetamide;
120. (S)-N-{3-[4-(4-(1-cyano-1-ethoxycarbonyl-methylidene)-piperidin-1-yl)-3-fluorophenyl]-2-oxo-oxazolidin-5-ylmethyl}-thioacetamide;
121. (S)-N-{3-[4-(4-(1-cyano-1-(morpholin-1-yl-thiocarbonyl)-methylidene)-piperidin-1-yl)-3-fluorophenyl]-2-oxo-oxazolidin-5-ylmethyl}-thioacetamide;

Some preferred examples of the oxazolidinone derivatives represented by the general Formula I and belonging to the subclass Formula III are as follows:

Formula III 122. (S)-{3-[4-(4-cyanomethyl-piperidin-1-yl)-phenyl]-2-oxo-oxazolidin-5-ylmethyl}-azide;
123. (S)-1-{3-[4-(4-cyanomethyl-piperidin-1-yl)-phenyl]-2-oxo-oxazolidin-5-ylmethyl}-4-carboethoxy-1,2,3-triazole;
124. (R)-{3-[4-(4-cyanomethyl-piperidin-1-yl)-phenyl]-2-oxo-oxazolidin-5-ylmethyl}-alcohol;
125. (R)-{3-[4-(4-cyanomethyl-piperidin-1-yl)-phenyl]-2-oxo-oxazolidin-5-ylmethyl}-methanesulphonate;
126. (S)-N-{3-[4-(4-cyanomethyl-piperidin-1-yl)-phenyl]-2-oxo-oxazolidin-5-ylmethyl}-thioacetamide;
127. (S)-1-{3-[4-(4-cyanomethyl-piperidin-1-yl)-3-fluorophenyl]-2-oxo-oxazolidin-5-ylmethyl}-4-carboxamido-1,2,3-triazole;
128. (S)-1-{3-[4-(4-cyanomethyl-piperidin-1-yl)-3-fluorophenyl]-2-oxo-oxazolidin-5-ylmethyl}-4-cyano-1,2,3-triazole;
129. (S)-N-{3-[4-(4-cyanomethyl-piperidin-1-yl)-3-fluorophenyl]-2-oxo-oxazolidin-5-ylmethyl}-thioacetamide;
130. (S)-N-{3-[4-(4-cyanomethyl-3-fluoropiperidin-1-yl)-phenyl]-2-oxo-oxazolidin-5-ylmethyl}-thioacetamide;
131. (R)-{3-[4-(4-cyanomethyl-3-fluoropiperidin-1-yl)-phenyl]-2-oxo-oxazolidin-5-ylmethyl}-alcohol;
132. (R)-{3-[4-(4-cyanomethyl-3-fluoropiperidin-1-yl)-phenyl]-2-oxo-oxazolidin-5-ylmethyl}-methanesulphonate;
133. (S)-N-{3-[4-(4-(1-cyano-1-benzyl)-methylpiperidin-1-yl)-3-fluorophenyl]-2-oxo-oxazolidin-5-ylmethyl}-acetamide;
134. (S)-N-{3-[4-(4-(1-cyano-2-methanesulphonyloxy)-ethylpiperidin-1-yl)-3-fluorophenyl]-2-oxo-oxazolidin-5-ylmethyl}-acetamide;
135. (S)-N-{3-[4-(4-(1-cyano-1-(3,4-difluorophenyl))-methylpiperidin-1-yl)-3-fluorophenyl]-2-oxo-oxazolidin-5-ylmethyl}-acetamide;
136. (S)-N-{3-[4-(4-(1-cyano-1-(imidazol-1-yl))-methylpiperidin-1-yl)-3-fluorophenyl]-2-oxo-oxazolidin-5-ylmethyl}-acetamide;
137. (S)-N-{3-[4-(4-(1-cyano-1-(thiophen-2-yl))-methylpiperidin-1-yl)-3-fluorophenyl]-2-oxo-oxazolidin-5-ylmethyl}-acetamide;
138. (S)-N-{3-[4-(4-(1-cyano-1-(pyridin-2-yl))-methylpiperidin-1-yl)-3-fluorophenyl]-2-oxo-oxazolidin-5-ylmethyl}-acetamide;

139. (S)-N-{3-[4-(4-(1-cyano-1-carboxamido)-methylpiperidin-1-yl)-3-fluorophenyl]-2-oxo-oxazolidin-5-ylmethyl}-acetamide;
140. (S)-N-{3-[4-(4-(1-cyano-1-cyclohexylaminocarbonyl)-methylpiperidin-1-yl)-3-fluorophenyl]-2-oxo-oxazolidin-5-ylmethyl}-acetamide;
141. (S)-N-{3-[4-(4-(1-cyano-1-(pyrrolidin-1-yl-carbonyl))-methylpiperidin-1-yl)-3-fluorophenyl]-2-oxo-oxazolidin-5-ylmethyl}-acetamide;
142. (S)-N-{3-[4-(4-(1-cyano-1-(morpholin-1-yl-carbonyl))-methylpiperidin-1-yl)-3-fluorophenyl]-2-oxo-oxazolidin-5-ylmethyl}-acetamide;
143. (S)-N-{3-[4-(4-(1-cyano-1-ethoxycarbonyl)-methylpiperidin-1-yl)-3-fluorophenyl]-2-oxo-oxazolidin-5-ylmethyl}-acetamide;
144. (S)-N-{3-[4-(4-(1-cyano-1-(phenylmercapto))-methylpiperidin-1-yl)-3-fluorophenyl]-2-oxo-oxazolidin-5-ylmethyl}-acetamide;
145. (S)-N-{3-[4-(4-(1-cyano-1-(pyridin-2-yl))-methylpiperidin-1-yl)-3-fluorophenyl]-2-oxo-oxazolidin-5-ylmethyl}-thioacetamide;
146. (S)-N-{3-[4-(4-(1-cyano-1-(morpholin-1-yl-carbonyl))-methylpiperidin-1-yl)-3-fluorophenyl]-2-oxo-oxazolidin-5-ylmethyl}-thioacetamide;
147. (S)-N-{3-[4-(4-(1-cyano-1-ethoxycarbonyl)-methylpiperidin-1-yl)-3-fluorophenyl]-2-oxo-oxazolidin-5-ylmethyl}-thioacetamide;
148. (S)-N-{3-[4-(4-(1-cyano-1-carboxamido)-methylpiperidin-1-yl)-3-fluorophenyl]-2-oxo-oxazolidin-5-ylmethyl}-thioacetamide;
149. (S)-N-{3-[4-(4-(1-cyano-1-thiocarboxamido)-methylpiperidin-1-yl)-3-fluorophenyl]-2-oxo-oxazolidin-5-ylmethyl}-thioacetamide;
150. (S)-1-{3-[4-(4-(1-cyano-2-hydroxy)-ethylpiperidin-1-yl)-3-fluorpheny]-2-oxo-oxazolidin-5-ylmethyl}-4-methoxycarbonyl-1,2,3-triazole;
151. (S)-1-{3-[4-(4-(1-cyano-2-hydroxy)-ethylpiperidin-1-yl)-3-fluorophenyl]-2-oxo-oxazolidin-5-ylmethyl}-4-ethoxycarbonyl-1,2,3-triazole;
152. (S)-1-{3-[4-(4-(1-cyano-2-hydroxy)-ethylpiperidin-1-yl)-3-fluorophenyl]-2-oxo-oxazolidin-5-ylmethyl}-5-ethoxycarbonyl-1,2,3-triazole;
153. (R)-3-{3-[4-(4-(1-cyano-2-hydroxy)-ethylpiperidin-1-yl)-3-fluorophenyl]-2-oxo-oxazolidin-5-ylmethyloxy}-iso-oxazole;
154. (R)-{3-[4-(4-(1-cyano-2-hydroxy)-ethylpiperidin-1-yl)-3-fluorophenyl]-2-oxo-oxazolidin-5-ylmethyl}-methanesulphonate;
155. (R)-{3-[4-(4-(1-cyano-1-hydroxycarbonyl)-methylpiperidin-1-yl)-3-fluorophenyl]-2-oxo-oxazolidin-5-ylmethyl}-methanesulphonate;
156. (R)-{3-[4-(4-(1-cyano-1-ethoxycarbonyl)-methylpiperidin-1-yl)-3-fluorophenyl]-2-oxo-oxazolidin-5-ylmethyl}-methanesulphonate;
157. (R)-{3-[4-(4-(1-cyano-1-(1,3-thiazol-2-yl))-methylpiperidin-1-yl)-3-fluorophenyl]-2-oxo-oxazolidin-5-ylmethyl}-methanesulphonate;
158. (R)-{3-[4-(4-(1-cyano-1-carboxamido)-methylpiperidin-1-yl)-3-fluorophenyl]-2-oxo-oxazolidin-5-ylmethyl}-methanesulphonate;

Some preferred examples of the oxazolidinone derivatives represented by the general Formula I and belonging to the subclass Formula IV are as follows:

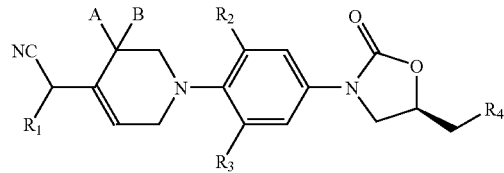

Formula IV 159. (S)-N-{3-[4-(4-cyanomethyl-3,4-dehydropiperidin-1-yl)-3-fluorophenyl]-2-oxo-oxazolidin-5-ylmethyl}-acetamide;
160. (S)-N-{3-[4-(4-cyanomethyl-3,4-dehydropiperidin-1-yl)-3-fluorophenyl]-2-oxo-oxazolidin-5-ylmethyl}-thioacetamide;
161. (S)-N-{3-[4-(4-cyanomethyl-3-methyl-4,5-dehydropiperidin-1-yl)-3-fluorophenyl]-2-oxo-oxazolidin-5-ylmethyl}-acetamide;
162. (S)-N-{3-[4-(4-cyanomethyl-3-fluoro-4,5-dehydropiperidin-1-yl)-3-fluorophenyl]-2-oxo-oxazolidin-5-ylmethyl}-acetamide;
163. (S)-N-{3-[4-(4-cyanomethyl-3-fluoro-4,5-dehydropiperidin-1-yl)-3-fluorophenyl]-2-oxo-oxazolidin-5-ylmethyl}-isobutylcarbamate;

More particularly preferred compounds of the invention of the Formula 1 are:

(S)-N-{3-[4-(4-cyanomethylidene-piperidin-1-yl)-phenyl]-2-oxo-oxazolidin-5-ylmethyl}-acetamide;
(S)-N-{3-[4-(4-cyanomethylidene-piperidin-1-yl)-3-fluorophenyl]-2-oxo-oxazolidin-5-ylmethyl}-acetamide;
(S)-N-{3-[4-(4-cyanomethylidene-piperidin-1-yl)-3-fluorophenyl]-2-oxo-oxazolidin-5-ylmethyl}-2-cyanoacetamide;
(S)-N-{3-[4-(4-cyanomethylidene-piperidin-1-yl)-3-fluorophenyl]-2-oxo-oxazolidin-5-ylmethyl}-trifluoroacetamide;
(S)-N-{3-[4-(4-cyanomethylidene-piperidin-1-yl)-3-fluorophenyl]-2-oxo-oxazolidin-5-ylmethyl}-chloroacetamide;
(S)-N-{3-[4-(4-cyanomethylidene-piperidin-1-yl)-3-fluorophenyl]-2-oxo-oxazolidin-5-ylmethyl}-dichloroacetamide;
(S)-N-{3-[4-(4-cyanomethylidene-piperidin-1-yl)-3-fluorophenyl]-2-oxo-oxazolidin-5-ylmethyl}-thioacetamide;
(S)-N-{3-[4-(4-cyanomethylidene-piperidin-1-yl)-3-fluorophenyl]-2-oxo-oxazolidin-5-ylmethyl}-methylthiocarbamate;
(S)-N-{3-[4-(4-cyanomethylidene-piperidin-1-yl)-3-fluorophenyl]-2-oxo-oxazolidin-5-ylmethyl}-2-hydroxythioacetamide;
(S)-N-{3-[4-(4-cyanomethylidene-piperidin-1-yl)-3-fluorophenyl]-2-oxo-oxazolidin-5-ylmethyl}-thiocarbamide;
E-(S)-N-{3-[4-(4-cyanomethylidene-3-fluoropiperidin-1-yl)-3-fluorophenyl]-2-oxo-oxazolidin-5-ylmethyl}-acetamide;
Z-(S)-N-{3-[4-(4-cyanomethylidene-3-fluoropiperidin-1-yl)-3-fluorophenyl]-2-oxo-oxazolidin-5-ylmethyl}-acetamide;
(S)-N-{3-[4-(4-cyanomethylidene-3-fluoropiperidin-1-yl)-3-fluorophenyl]-2-oxo-oxazolidin-5-ylmethyl}-difluoroacetamide;
(S)-N-{3-[4-(4-cyanomethylidene-3-fluoropiperidin-1-yl)-3-fluorophenyl]-2-oxo-oxazolidin-5-ylmethyl}-thioacetamide;

(S)-N-{3-[4-(4-cyanomethylidene-3-methylpiperidin-1-yl)-3-fluorophenyl]-2-oxo-oxazolidin-5-ylmethyl}-thiocarbamide;

(S)-N-{3-[4-(4-cyanomethylidene-3-methylpiperidin-1-yl)-3-fluorophenyl]-2-oxo-oxazolidin-5-ylmethyl}-methylthiocarbamide;

(S)-N-{3-[4-(4-(1-cyanoethylidene)-piperidin-1-yl)-3-fluorophenyl]-2-oxo-oxazolidin-5-ylmethyl}-acetamide;

(S)-N-{3-[4-(4-(1-cyanoethylidene)-piperidin-1-yl)-3-fluorophenyl]-2-oxo-oxazolidin-5-ylmethyl}-difluoroacetamide;

(S)-N-{3-[4-(4-(1-cyanoethylidene)-piperidin-1-yl)-3-fluorophenyl]-2-oxo-oxazolidin-5-ylmethyl}-dichloroacetamide;

(S)-N-{3-[4-(4-(1-cyanoethylidene)-piperidin-1-yl)-3-fluorophenyl]-2-oxo-oxazolidin-5-ylmethyl}-thioacetamide;

(S)-N-{3-[4-(4-(1-cyanopropylidene)-piperidin-1-yl)-3-fluorophenyl]-2-oxo-oxazolidin-5-ylmethyl}-acetamide;

(S)-N-{3-[4-(4-(1-cyanopropylidene)-piperidin-1-yl)-3-fluorophenyl]-2-oxo-oxazolidin-5-ylmethyl}-dichloroacetamide;

(S)-N-{3-[4-(4-(1-cyanopropylidene)-piperidin-1-yl)-3-fluorophenyl]-2-oxo-oxazolidin-5-ylmethyl}-thioacetamide;

(S)-N-{3-[4-(4-(1-cyano-3-yne-butylidene)-piperidin-1-yl)-3-fluorophenyl]-2-oxo-oxazolidin-5-ylmethyl}-acetamide;

(S)-N-{3-[4-(4-(1-cyano-1-(thiophen-2-yl)-methylidene)-piperidin-1-yl)-3-fluorophenyl]-2-oxo-oxazolidin-5-ylmethyl}-acetamide;

(S)-N-{3-[4-(4-(1-cyano-1-methylmercapto-methylidene)-piperidin-1-yl)-3-fluorophenyl]-2-oxo-oxazolidin-5-ylmethyl}-acetamide;

(S)-N-{3-[4-(4-(1-cyano-1-bromo-methylidene)-piperidin-1-yl)-3-fluorophenyl]-2-oxo-oxazolidin-5-ylmethyl}-acetamide;

(S)-N-{3-[4-(4-(1-cyano-1-(pyridin-2-yl)-methylidene)-piperidin-1-yl)-3-fluorophenyl]-2-oxo-oxazolidin-5-ylmethyl}-thioacetamide;

(S)-N-{3-[4-(4-(1,1-dicyano-methylidene)-piperidin-1-yl)-3-fluorophenyl]-2-oxo-oxazolidin-5-ylmethyl}-thioacetamide;

(S)-N-{3-[4-(4-(1-cyano-1-ethoxycarbonyl-methylidene)-piperidin-1-yl)-3-fluorophenyl]-2-oxo-oxazolidin-5-ylmethyl}-thioacetamide;

(S)-N-{3-[4-(4-(1-cyano-1-(morpholin-1-yl-thiocarbonyl)-methylidene)-piperidin-1-yl)-3-fluorophenyl]-2-oxo-oxazolidin-5-ylmethyl}-thioacetamide;

(S)-N-{3-[4-(4-cyanomethyl-3,4-dehydropiperidin-1-yl)-3-fluorophenyl]-2-oxo-oxazolidin-5-ylmethyl}-acetamide;

(S)-N-{3-[4-(4-cyanomethyl-3,4-dehydropiperidin-1-yl)-3-fluorophenyl]-2-oxo-oxazolidin-5-ylmethyl}-thioacetamide;

(S)-N-{3-[4-(4-cyanomethyl-3-fluoro-4,5-dehydropiperidin-1-yl)-3-fluorophenyl]-2-oxo-oxazolidin-5-ylmethyl}-acetamide;

A further embodiment of the invention is to provide methods of preparation of the compound of the invention.

Scheme I describes the preparation of compounds of Formulae II, III and IV of the present invention. All of the starting materials are prepared by procedures described in this scheme or by procedures that would be well known to one of ordinary skill in organic chemistry. The variables used in Scheme 1 are as defined above. Optically pure material could be obtained either by one of a number of asymmetric synthesis or alternatively by resolution from a racemic mixture.

In accordance with the Scheme-I piperidone (i) (for example, the preparation of one such piperidone is described in U.S. Pat. No. 5,668,286) is reacted with cyano substituted active methylene compounds ii ($R_1$ as defined) in the presence of a base such as ammonium acetate, sodium methoxide, pyridine and piperidine acetate, preferably ammonium acetate and pyridine and in a solvent such as toluene, THF and methanol at 30-110° C. for 2-48 hrs. to provide compounds of formula II. Alternatively, i is reacted with a Wittig reagent optionally in the presence of a base such as triethylamine, sodium hydride or n-butyl lithium in a solvent such as ether, tetrahydrofuran or benzene at 10-80° C. to provide compounds of formula II.

The resultant unsaturated cyano derivatives are reduced by hydrogenation in the presence of catalysts such as 5% palladium on carbon, 10% palladium on carbon, palladium hydroxide at atmospheric pressure of hydrogen gas, alternatively by using hydrogen sources such as ammonium formate, cyclohexene in a solvent such as ethyl acetate, methanol, tetrahydrofuran, dichloromethane or chloroform or a mixture thereof at 20-60° C. for 1 to 24 hrs. to provide compounds of formula III.

In accordance with the scheme-I, i is reacted with unsubstituted/substituted cyanoacetic acid in the presence of a base such as pyridine, piperidine and ammonium acetate in a solvent such as benzene, toluene at a temperature of 80 to 120° C. for 3 to 24 hrs. to provide compounds of formula IV.

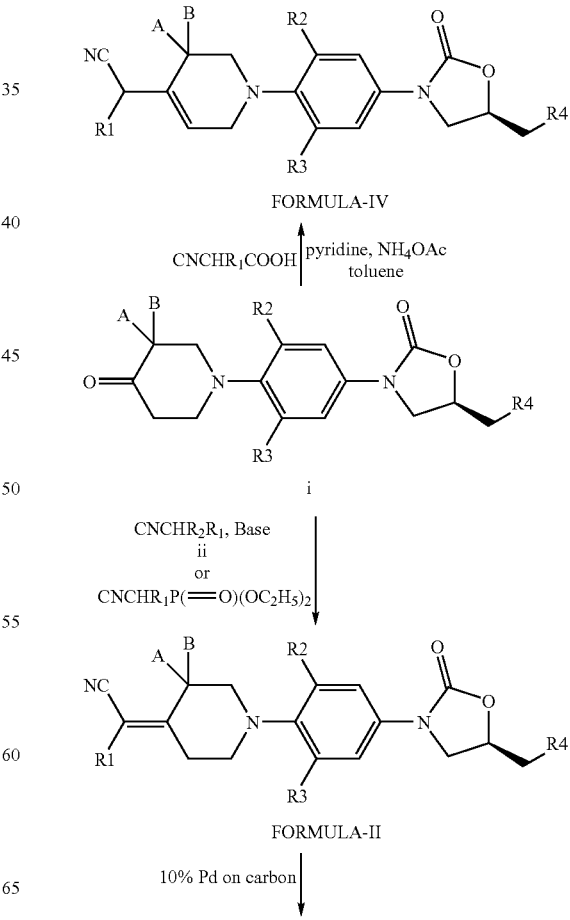

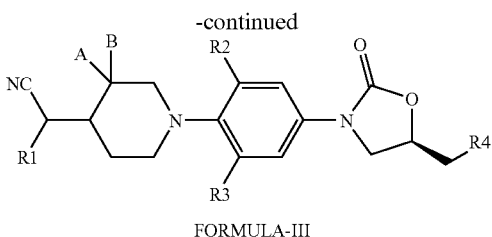

FORMULA-III

Thioacetamides can conveniently be prepared by allowing the acetamide derivatives to react with Lawesson's reagent in 1,4 dioxane, benzene, toluene or tetrahydrofuran at 60 to 110° C.

The oxazolidinone antibacterial agents of this invention have potential for treatment of specially Gram-positive infections including multi-resistant strains. In contrast to compounds of the prior art, they demonstrate bactericidal activity against different resistant microorganisms and in particular different strains of *Enterococcus faecalis*. In addition they display activity against linezolid-resistant *S. aureus* strains, linezolid-resistant *E. faecalis* strains and in particular linezolid-resistant *S. pneumoniae* strains. These compounds are useful for the treatment of Gram-positive or Gram-negative microbial infections in humans and other warm blooded animals by either parenteral, oral or topical administration. The infection in human and other warm blooded animals can be systemic or topical.

The compounds of this invention may be used to prevent infections caused by Gram-positive and Gram-negative bacteria by administering the compound to a subject that is at risk for developing an infection caused by Gram-positive or Gram-negative bacteria. A subject at risk for developing an infection may be a health care worker, surgical patient and the like.

The present invention encompasses certain compounds, dosage forms, and methods of administering the compounds to a human or other animal subject. Specific compounds and compositions to be used in the invention must, accordingly, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio.

The pharmaceutical compositions are prepared according to conventional procedures used by persons skilled in the art to make stable and effective compositions. In the solid, liquid, parenteral and topical dosage forms, an effective amount of the active compound or the active ingredient is any amount, which produces the desired results.

For the purpose of this invention the pharmaceutical compositions may contain the active compounds of the invention, their derivatives, salts and hydrates thereof, in a form to be administered alone, but generally in a form to be administered in admixture with a pharmaceutical carrier selected with regard to the intended route of administration and standard pharmaceutical practice. Suitable carriers which can be used are, for example, diluents or excipients such as fillers, extenders, binders, emollients, wetting agents, disintegrants, surface active agents and lubricants which are usually employed to prepare such drugs depending on the type of dosage form.

Any suitable route of administration may be employed for providing the patient with an effective dosage of the compound of the invention their derivatives, salts and hydrates thereof. For example, oral, rectal, vaginal, parenteral (subcutaneous, intramuscular, intravenous), transdermal, topical and like forms of administration may be employed. Dosage forms include (solutions, suspensions, etc) tablets, pills, powders, troches, dispersions, suspensions, emulsions, solutions, capsules, injectable preparations, patches, ointments, creams, lotions, shampoos and the like.

The prophylactic or therapeutic dose of the compounds of the invention, their derivatives, salts or hydrates thereof, in the acute or chronic management of disease will vary with the severity of condition to be treated, and the route of administration. In addition, the dose, and perhaps the dose frequency, will also vary according to the age, body weight and response of the individual patient. In general, the total daily dose range, for the compounds of the invention, the derivatives, salts or hydrates thereof, for the conditions described herein, is from about 200 mg to about 1500 mg, in single or divided doses. Preferably, a daily dose range should be between about 400 mg to 1200 mg, in single or divided dosage, while most preferably a daily dose range should be between about 500 mg to about 1000 mg in divided dosage. While intramuscular administration may be a single dose or up to 3 divided doses, intravenous administration can include a continuous drip. It may be necessary to use dosages outside these ranges in some cases as will be apparent to those skilled in the art. Further, it is noted that the clinician or treating physician will know how and when to interrupt, adjust, or terminate therapy in conjunction with individual patient's response. The term "an amount sufficient to eradicate such infections but insufficient to cause undue side effects" is encompassed by the above—described dosage amount and dose frequency schedule.

A specific embodiment of the invention is that the pharmacokinetic profile of a compound of the invention is such that it permits administration of a dosage schedule which is a much desired once-a-day dosing, a schedule not so far advocated for the only currently available oxazolidinone drug in the market.

A further specific embodiment of the invention is that a compound of the invention has favourable safety advantages in particular no or lower potential to cause myelosuppression. Myelosuppression is known to be a typical class-specific toxicological feature of the oxazolidinone class of antibacterial agents.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

The compositions of the present invention include compositions such as suspensions, solutions, elixirs, aerosols, and solid dosage forms. Carriers as described in general above are commonly used in the case of oral solid preparations (such as powders, capsules and tablets), with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan), sodium lauryl sulfate, stearic acid monoglyceride, starch, and lactose, disintegration inhibitors such as white sugar, stearic acid glyceryl ester, cacao butter and hydrogenated oils, absorption promoters such as quaternary ammonium bases and sodium lauryl sulfate, humectants such as glycerol and starch, absorbents such as starch, lactose, kaolin, bentonite and colloidal silicic acid, and lubricants such as purified talc, stearic acid salts, boric acid powder, polyethylene glycol and solid polyethylene glycol.

The tablet, if desired, can be coated, and made into sugar-coated tablets, gelatin-coated tablets, enteric-coated tablets, film-coated tablets, or tablets comprising two or more layers.

If desired, tablets may be coated by standard aqueous or non-aqueous techniques. In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, gelatin, and semi-synthetic glycerides.

A second preferred method is parenterally for intramuscular, intravenous or subcutaneous administration.

A third preferred route of administration is topically, for which creams, ointments, shampoos, lotions, dusting powders and the like are well suited. Generally, an effective amount of the compound according to this invention in a topical form is from about 0.1% w/w to about 10% w/w of the total composition. Preferably, the effective amount of the compound of the invention is 1% w/w of the total composition.

In addition to the common dosage forms set out above, the compounds of the present invention may also be administered by controlled release means and/or delivery devices such as those described in U.S. Pat. Nos. 3,845,770; 3,916,899; 3,536,809; 3,598,123 and 4,008,719; the disclosures of which are hereby incorporated by reference.

Desirably, each tablet contains from about 200 mg to about 1500 mg of the active ingredient. Most preferably, the tablet, cachet or capsule contains either one of three dosages, about 200 mg, about 400 mg, or about 600 mg of the active ingredient.

When the pharmaceutical composition is formulated into an injectable preparation, in formulating the pharmaceutical composition into the form of a solution or suspension, all diluents customarily used in the art can be used. Examples of suitable diluents are water, ethyl alcohol, polypropylene glycol, ethoxylated isostearyl alcohol, polyoxyethylene sorbitol, and sorbitan esters. Sodium chloride, glucose or glycerol may be incorporated into a therapeutic agent.

The antimicrobial pharmaceutical composition may further contain ordinary dissolving aids, buffers, pain-alleviating agents, and preservatives, and optionally coloring agents, perfumes, flavors, sweeteners, and other drugs.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g. preservatives, antioxidants, stabilizers, wetting agents, buffers or salts for influencing osmotic pressure, etc. For topical application, also suitable are sprayable aerosol preparations wherein the active ingredient preferably in combination with a solid or liquid inert carrier material.

A specific embodiment of the invention is the preparation of storage stable compositions of the compounds of the invention of formula I. Such stable compositions can be advantageously made through the use of selective stabilizers. Different stabilizers are known to those skilled in the art of making pharmaceutical compositions. Of special utility for making storage stable compositions of the compound of the invention of formula I, stabilizers such as disodium ethylenediaminetetraacetic acid (EDTA), tromethamine, cyclodextrins such as gamma-cyclodextrin, hydroxy-propyl-gamma-cyclodextrin have been found to be useful.

In a specific embodiment of the invention, the pharmaceutical compositions contain an effective amount of the active compounds of the invention, its derivatives, salts or hydrates thereof described in this specification as hereinbefore described in admixture with a pharmaceutically acceptable carrier, diluent or excipients, and optionally other therapeutic ingredients.

The invention is further defined by reference to the following examples describing in detail the preparation of the composition of the present invention as well as their utility. It will be apparent to those skilled in the art that many modifications, both to materials and methods may be practiced without departing from the purpose and scope of this invention.

The compounds of this invention are useful antimicrobial agents effective against various humans and veterinary pathogens specially including Linezolid-resistant strains.

Further embodiments of the invention are the linezolid-resistant strains of the invention and methods for producing them. Linezolid-resistant mutants *S. pneumoniae* ATCC 6303 LR, *S. aureus* Smith LR & MRSA 032 LR were selected from corresponding sensitive strains *S. pneumoniae* ATCC 6303, *S. aureus* Smith & MRSA 032 respectively under in-vivo conditions from mice infected with respective parent strains and treated with various dosages of linezolid. Selected mutants and parent strains were analyzed for the presence of mutation in 23S rRNA by sequencing. The methodology involved amplication of genes coding 23S rRNA from linezolid-resistant mutants employing a PCR based DNA amplification method. The mutations in 23S rRNA gene were identified by sequencing of amplified DNA following electrophoretic separation.

PREPARATIONS

Preparation-1

Preparation of 4-[4-oxo-piperidin-1-yl]-nitrobenzene

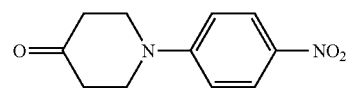

The mixture of 4-piperidone hydrochloride (0.851 mol), triethylamine (1.70 mol), 4-fluoronitrobenzene (0.851 mol) in 800 ml chloroform was heated under reflux for 16 hours. The solvent was removed under vacuum and to the residue water (1 liter) was added and the precipitate was filtered to afford 4-[4-oxo-piperidin-1-yl]-nitrobenzene in 80% yield.

MS (M+1)=221 (MH+, 100%), M.F.=$C_{11}H_{12}N_2O_3$.

Preparation-2

Preparation of 4-[4-(1,4-dioxa-8-aza-spiro[4.5]-dec-8-yl)]-nitrobenzene

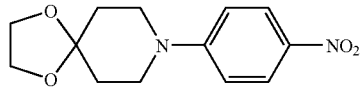

The mixture of 4-[4-oxo-piperidin-1-yl]-nitrobenzene from step-1 (0.596 mol), ethylene glycol (1.09 mol) and p-toluenesulphonic acid monohydrate (0.147 mol) in toluene was heated to reflux for 5 hours. The reaction mixture was washed with water. The organic layer was evaporated to afford 4-[4-(1,4-dioxa-8-aza-spiro[4.5]-dec-8-yl)]-nitrobenzene as a solid in 98% yield.

MS (M+1)=266 (MH+, 100%), M.F.=$C_{13}H_{16}N_2O_4$.

Preparation-3

Preparation of [4-(1,4-dioxa-8-aza-spiro[4.5]-dec-8-yl)]-phenyl-4-yl]-aminocarbonyloxymethyl]-benzene

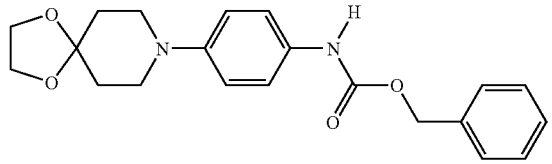

The suspension of 4-[4-(1,4-dioxa-8-aza-spiro[4.5]-dec-8-yl)]-nitrobenzene (0.377 mol), 10% palladium on carbon (10 g) in tetrahydrofuran (800 ml) was stirred at room temperature under hydrogen atmosphere (400 psi) overnight. The reaction mixture filtered to remove the catalyst. To the filtrate, sodium bicarbonate (0.56 mol) and benzyl chloroformate (0.41 mol) was added at 0-5° C. and stirred at room temperature for 30 minutes. The solvent was evaporated under vacuum and the residue stirred with hexane. The precipitate was filtered to give the title compound in 97% yield.

MS (M+1)=369 (MH+, 100%), M.F.=$C_{21}H_{24}N_2O_4$.

Preparation-4

Preparation of (R)-3-{4-(1,4-dioxa-8-aza-spiro[4.5]-dec-8-yl)]-phenyl)--2-oxo-oxazolidin-5-ylmethyl}-alcohol

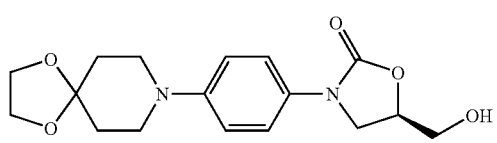

Butyl lithium (1.6 M in hexane, 180 ml) was added to the solution [4-(1,4-dioxa-8-aza-spiro[4.5]-dec-8-yl)]-phenyl-4-yl]-aminocarbonyloxymethyl]-benzene (0.313 mol) in tetrahydrofuran (1000 ml) at −78° C. (R)-(−)-Glycidyl butyrate (0.32 mol) was added to the reaction mixture and it was stirred overnight. The reaction mixture was extracted with the ethyl acetate after quenching with saturated aqueous ammonium chloride solution.

The evaporation of solvent afforded title compound in 80% yield.

MS (M+1)=335 (MH+, 100%), M.F.=$C_{17}H_{22}N_2O_5$.

Preparation-5

Preparation of (R)-{3-[4-(4-oxo-piperidin-1-yl)-phenyl]-2-oxo-oxazolidin-5-ylmethyl}-alcohol

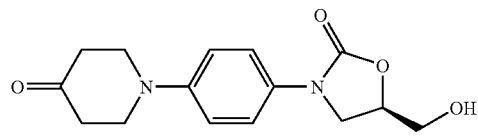

The mixture of (R)-{3-[4-(4-(1,4-dioxa-8-aza-spiro[4.5]-dec-8-yl)-phenyl]-2-oxo-oxazolidin-5-ylmethyl}-alcohol (0.016 mol), p-toluene sulfonic acid (0.032 mol) in acetone water (300 ml, 40:60) mixture was refluxed for 6 hours. The reaction mixture was concentrated under vacuum and treated with saturated aqueous sodiumbicarbonate solution. The precipitate was filtered to afford title compound 78% yield.

MS (M+1)=291 (MH+, 100%), M.F.=$C_{15}H_{18}N_2O_4$.

Preparation-6

Preparation of (R)-{3-[4-(4-oxo-piperidin-1-yl)-phenyl]-2-oxo-oxazolidin-5-ylmethyl}-methanesulphonate

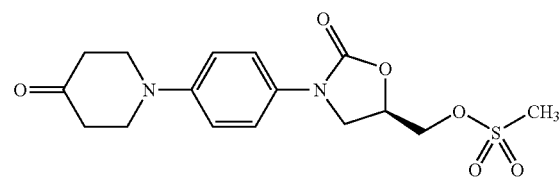

The mixture of (R)-{3-[4-(4-oxo-piperidin-1-yl)-phenyl]-2-oxo-oxazolidin-5-ylmethyl}-alcohol (0.194 mol), triethylamine (0.213 mmol), and methanesulphonyl chloride (0.232 mol) in 700 ml of dichloromethane was stirred for 1 hour. The reaction mixture was washed with 1 liter water. The organic layer was dried and evaporated under vacuum to afford title compound in 87% yield.

MS (M+1)=369 (MH+, 100%), M.F.=$C_{16}H_{20}N_2O_6S$.

Preparation-7

Preparation of (S)-{3-[4-(4-(1,4-dioxa-8-aza-spiro[4.5]-dec-8-yl)-phenyl]-2-oxo-oxazolidin-5-ylmethyl}-azide

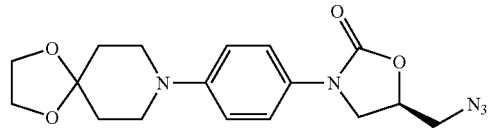

The mixture of (R)-{3-[4-(4-(1,4-dioxa-8-aza-spiro[4.5]-dec-8-yl)-phenyl]-2-oxo-oxazolidin-5-ylmethyl}-methanesulfonate (0.16 mol), sodium azide (0.46 mol) in dimethylformamide (200 ml) was heated at 70° C. for 14 hours. The reaction mixture was cooled and poured in ice cold water. The precipitate was filtered to provide title compound in 85% yield.

MS (M+1)=360 (MH+, 100%), M.F.=$C_{17}H_{21}N_5O_4$.

Preparation-8

Preparation of (S)-{3-[4-(4-oxo-piperidin-1-yl)-phenyl]-2-oxo-oxazolidin-5-ylmethyl}-azide

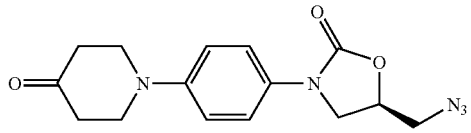

The mixture of (S)-{3-[4-(4-(1,4-dioxa-8-aza-spiro[4.5]-dec-8-yl)-phenyl]-2-oxo-oxazolidin-5-ylmethyl}-azide (0.014 mol),p-toluene sulfonic acid (0.026 mol) in acetone water (150 ml, 40:60) mixture was refluxed for 6 hours. The reaction mixture was concentrated under vacuum and treated with saturated aqueous sodiumbicarbonate solution. The precipitate was filtered to afford keto oxazolidinone azide compound 50% yield.

MS (M+1)=316 (MH+, 100%), M.F.=$C_{15}H_{17}N_5O_3$.

Preparation-9

Preparation of (S)-N-{3-[4-(4-(1,4-dioxa-8-aza-spiro[4.5]-dec-8-yl)-phenyl]-2-oxo-oxazolidin-5-ylmethyl}-acetamide

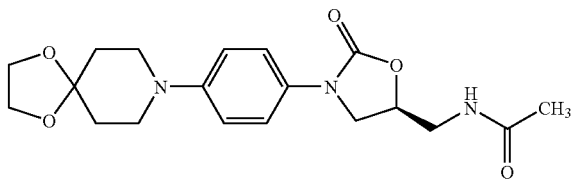

The suspension of (S)-{3-[4-(4-(1,4-dioxa-8-aza-spiro[4.5]-dec-8-yl)-phenyl]-2-oxo-oxazolidin-5-ylmethyl}-azide (0.153 mol), 10% palladium on carbon (7 g), pyridine (0.45 mol), acetic anhydride (0.18 mol) in 700 ml ethyl acetate was stirred at 400 psi hydrogen gas pressure overnight. The suspension was filtered. Filtrate was purified to provide title compound in 70% yield.

MS (M+1)=376 (MH+, 100%), M.F.=$C_{19}H_{25}N_3O_5$.

Preparation-10

Preparation of (S)-N-{3-[4-(4-oxo-iperidin-1-yl)-phenyl]-2-oxo-oxazolidin-5-ylmethyl}-acetamide

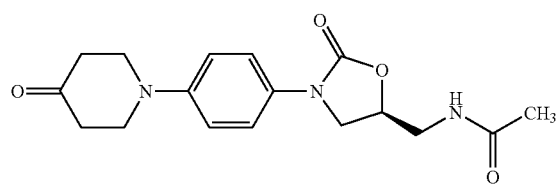

The (S)-N-{3-[4-(4-(1,4-dioxa-8-aza-spiro[4.5]-dec-8-yl)-phenyl]-2-oxo-oxazolidin-5-ylmethyl}-acetamide (0.040 mol),p-toluene sulfonic acid (0.080 mol) in acetone water (350 ml, 40:60) mixture was refluxed for 5 hours. The reaction mixture was concentrated under vacuum and treated with saturated aqueous sodiumbicarbonate solution. The precipitate was filtered to afford keto oxazolidinone acetamide compound 76% yield.

MS (M+1)=332 (MH+, 100%), M.F.=$C_{17}H_{21}N_3O$=.

Preparation-11

Preparation of 4-(4-trimethylsilyloxy-piperidin-1-yl)-nitrobenzene

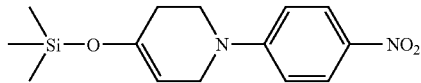

The mixture of 4-(4-oxo-Piperidin-1-yl)-nitrobenzene (126 mmol), triethylamine (630 mmol), trimethylsilylchloride (375.0 mmol) in dimethylformamide was heated at 70° C. for 24 h. The solvent was removed under vacuum and to the residual mass was extracted with the ethyl acetate water mixture. The combined organic layer was dried and after removal of the solvent afforded title compound as a solid in 90% yield.

MS (M+1)=293 (MH+, 100%), M.F.=$C_{14}H_{20}N_2O_3Si$.

Preparation-12

Preparation of 4-(3-fluoro-4-oxo-piperidin-1-yl)-nitrobenzene

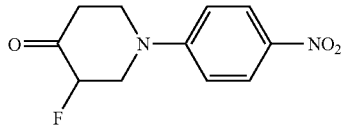

The mixture of 4-(4-trimethylsilyloxy-piperidin-1-yl)-nitrobenzene (101 mmol), selectfluor (101 mmol) in acetonitrile (100 ml) was stirred for 4 hours. The solvent was removed under reduced pressure and to the residual mass was extracted into ethyl acetate water mixture. The combined organic layer was dried and removal of the solvent afforded title compound in 95% yield.

MS (M+1)=239 (MH+, 100%), M.F.=$C_{11}H_{11}FN_2O_3$.

Preparation-13

Preparation of 4-(4,4-dimethoxy-3-fluoropiperidin-1-yl)-nitrobenzene

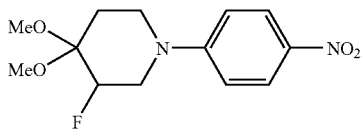

The mixture of 4-(3-fluoro-4-oxo-piperidin-1-yl)-nitrobenzene (51 mmol), trimethylorthoformate (103 mmol), p-toluene-sulphonic acid monohydrate (51 mmol) in methanol (100 ml) was heated at 45° C. for 24 hours. Solvent was removed and residual mass was taken into ethyl acetate and saturated sodium bicarbonate solution mixture. The organic layer was dried and removal of the solvent afforded title compound as a solid in 91% yield.

MS (M+1)=285 (MH+, 100%), M.F.=$C_{13}H_{17}FN_2O_4$.

Preparation-14

Preparation of [4-(4,4-dimethoxy-3-fluoropiperidin-yl)-aminocarbonyloxymethyl]-benzene

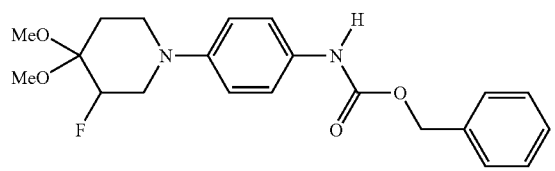

The suspension of 4-(4,4-dimethoxy-3-fluoropiperidin-yl)-nitrobenzene (38 mmol), and 10% palladium on carbon (1 g) in tetrahydrofuran (500 ml) was stirred at room temperature under hydrogen atmosphere (200 psi) for 6 hour. The suspension was filtered. To the filtrate sodium bicarbonate (57 mmol) and benzyl chloroformate (46 mmol) was added and the reaction mixture was stirred at room temperature for 30 min. The solvent was removed and the residue was extracted with ethyl acetate and water mixture. The organic layer was dried and the residue was recrystallized from hexane:ehtyl acetate to give the title compound in 93% yield.

MS (M+1)=389 (MH+, 100%), M.F.=$C_{21}H_{25}FN_2O_4$.

Preparation-15

Preparation of (R)-{3-[4-(4,4-dimethoxy-3-fluoropiperidin-1-yl)-phenyl]-2-oxo-oxazolidin-5-ylmethyl}-alcohol

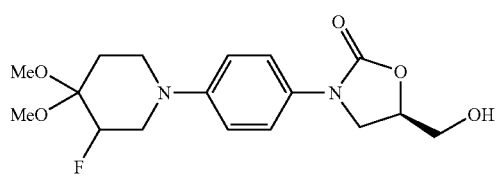

Butyl lithium (1.6 M in hexane, 27 ml) was added to the solution of [4-(4,4-dimethoxy-3-fluoropiperidin-yl)-aminocarbonyloxymethyl]-benzene (35.7 mmol) in tetrahydrofuran (250 ml) at −78° C. under an inert atmosphere. (R)-(−)-Glycidyl butyrate (37.5 mmol) was added to the reaction mixture and was stirred for 15 hours. The reaction mixture was extracted with the ethyl acetate water mixture. The combined organic layer was dried and removal of the solvent afforded a residue which was recrystallized from dichloromethane:hexane mixture to give title product in 89% yield.

MS (M+1)=355 (MH+, 100%), M.F.=$C_{17}H_{23}FN_2O_5$.

Preparation-16

Preparation of (R)-{3-[4-(4-oxo-3-fluoropiperidin-1-yl)-phenyl]-2-oxo-oxazolidin-5-ylmethyl}-alcohol

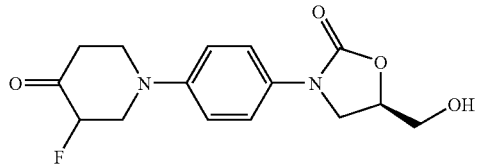

To the mixture of (R)-{3-[4-(4,4-dimethoxy-3-fluoropiperidin-1-yl)-phenyl]-2-oxo-oxazolidin-5-ylmethyl}-alcohol (0.726 mmol), freshly fused zinc chloride (2.17 mmol), dimethyl sulphide (3.2 mmol), acetyl chloride (2.17 mmol) in tetrahydrofuaran (50 ml) was stirred at 40° C. for 4 days. To this reaction mixture extracted with the ethyl acetate water mixture and organic layer was dried over sodium sulfate. The removal of the solvent afforded a residue, which was chromatographed over silica gel afforded title compound in 49% yield.

MS (M+1)=309 (MH+, 100%), M.F.=$C_{15}H_{17}FN_2O_4$.

Preparation-17

Preparration of (R)-{3-[4-(4,4-dimethoxy-3-fluoropiperidin-1-yl)-phenyl]-2-oxo-oxazolidin-5-ylmethyl}-methanesulfonate

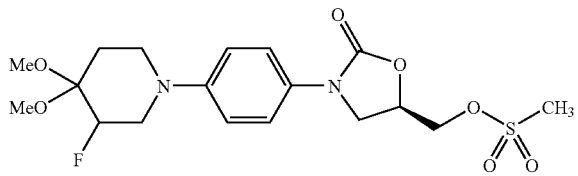

The mixture of (R)-{3-[4-(4,4-dimethoxy-3-fluoropiperidin-1-yl)-phenyl]-2-oxo-oxazolidin-5-ylmethyl}-alcohol (29.6 mmol), triethylamine (65 mmol), methanesulphonyl chloride (41.5 mmol) in dichloromethane (100 ml) was stirred for 1 hour at room temperature. Reaction mixture was extracted with the dichloromethane water mixture. The combined organic layer was dried over sodium sulfate and removal of solvent afforded title compound in 98% yield.

MS (M+1)=433 (MH+, 100%), M.F.=$C_{18}H_{25}FN_2O_7S$.

Preparation-18

Preparation of (R)-{3-[4-(4-oxo-3-Fluoropiperidin-1-yl)-phenyl]-2-oxo-oxazolidin-5-ylmethyl}-methanesulfonate

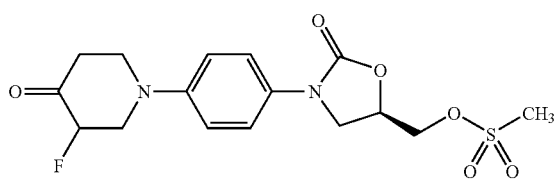

To the mixture of (R)-{3-[4-(4,4-dimethoxy-3-fluoropiperidin-1-yl)-phenyl]-2-oxo-oxazolidin-5-ylmethyl}-methanesulfonate (0.726 mmol), freshly fused zinc chloride (2.17 mmol), dimethyl sulphide (3.2 mmol), acetyl chloride (2.17 mmol) in tetrahydrofuaran (50 ml) was stirred at 40° C. for 4 days. To this reaction mixture extracted with the ethyl acetate water mixture and organic layer was dried over sodium sulfate. The removal of the solvent afforded a residue, which was chromatographed over silica gel afforded title compound in 57% yield.

MS (M+1)=387 (MH+, 100%), M.F.=$C_{16}H_{19}FN_2O_6S$.

Preparation-19

Preparation of (S)-{3-[4-(4,4-dimethoxy-3-fluoropiperidin-1-yl)-phenyl]-2-oxo-oxazolidin-5-ylmethyl}-azide

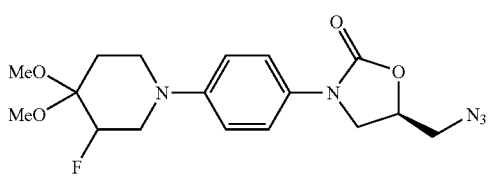

The mixture of sodium azide (88.5 mmol) and (R)-{3-[4-(4,4-dimethoxy-3-fluoropiperidin-1-yl)-phenyl]-2-oxo-oxazolidin-5-ylmethyl}-methanesulfonate (29.6 mmol) in dimethylformamide (75 ml) was heated at 70° C. for 14 hours. The reaction mixture was poured on ice cold water, and the solid was filtered to afford title compound in 78% yield.

MS (M+1)=380 (MH+, 100%), M.F.=$C_{17}H_{22}FN_5O_4$.

Preparation-20

Preparation of (S)-{3-[4-(4-oxo-3-fluoropiperidin-1-yl)-phenyl]-2-oxo-oxazolidin-5-ylmethyl}-azide

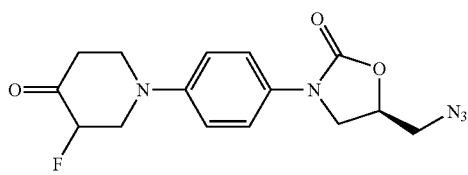

To the mixture of (S)-{3-[4-(4,4-dimethoxy-3-fluoropiperidin-1-yl)-phenyl]-2-oxo-oxazolidin-5-ylmethyl}-azide (0.5 mmol), freshly fused zinc chloride (1.5 mmol), dimethyl sulphide (2.5 mmol), acetyl chloride (1.5 mmol) in tetrahydrofuran (50 ml) was stirred at 40° C. for 4 days. To this reaction mixture extracted with the ethyl acetate water mixture and organic layer was dried over sodium sulfate. The removal of the solvent afforded a residue, which was chromatographed over silica gel afforded title compound in 67% yield.

MS (M+1)=334 (MH+, 100%), M.F.=$C_{15}H_{16}FN_5O_3$.

Preparation-21

Preparation of (S)-{3-[4-(4,4-dimethoxy-3-fluoropiperidin-1-yl)-phenyl]-2-oxo-oxazolidin-5-ylmethyl}-amine

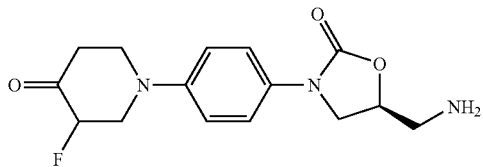

The suspension of (S)-{3-[4-(4,4-dimethoxy-3-fluoropiperidin-1-yl)-phenyl]-2-oxo-oxazolidin-5-ylmethyl}-azide (25.2 mmol) and 10% palladium on carbon (1.0 g) was in ethyl acetate (150 ml) was stirred at a room temperature under hydrogen atmosphere for 10 hours. The reaction mixture was filtered and the filtrate was concentrated to give a residue, which was purified on silica gel column chromatography to provide title compound in 89% yield.

MS (M+1)=308 (MH+, 100%), M.F.=$C_{15}H_{18}FN_3O_3$.

Preparation-22

Preparation of (S)-{3-[4-(4,4-dimethoxy-3-fluoropiperidin-1-yl)-phenyl]-2-oxo-oxazolidin-5-ylmethyl}-acetamide

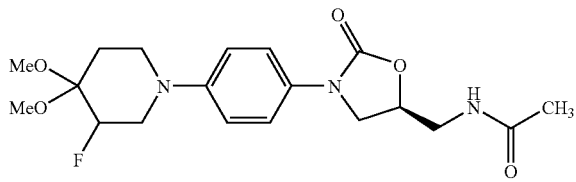

The mixture of (S)-{3-[4-(4,4-dimethoxy-3-fluoropiperidin-1-yl)-phenyl]-2-oxo-oxazolidin-5-ylmethyl}-amine (6.73 mmol), pyridine (26.9 mmol), acetic anhydride (9.43 mmol) in ethyl acetate (25 ml) was stirred for 5 hours at room temperature. The reaction mixture was extracted with the ethyl acetate water mixture and combined organic layer was dried over sodium sulfate. The removal of the solvent afforded a residue, which was chromatographed over silica gel to give title compound in 49% yield.

MS (M+1)=396 (MH+, 100%), M.F.=$C_{19}H_{26}FN_3O_5$.

Preparation-23

Preparation of (S)-{3-[4-(4-oxo-3-fluoropiperidin-1-yl)-phenyl]-2-oxo-oxazolidin-5-ylmethyl}-acetamide

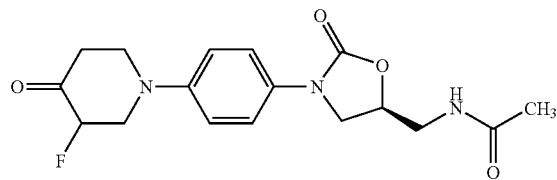

The mixture of (S)-{3-[4-(4,4-dimethoxy-3-fluoropiperidin-1-yl)-phenyl]-2-oxo-oxazolidin-5-ylmethyl}-acetamide (1.0 mmol), freshly fused zinc chloride (3.1 mmol), dimethyl sulphide (5.1 mmol), acetyl chloride (3.1 mmol) in tetrahydrofuaran (50 ml) was stirred at 40° C. for 4 days. The reaction mixture was extracted with ethyl acetate water mixture and the organic layer was dried over sodium sulfate. The removal of the solvent afforded a residue, which was chromatographed over silica gel to give title compound in 61% yield.

MS (M+1)=350 (MH+, 100%), M.F.=$C_{17}H_{20}FN_3O_4$.

Preparation-24

Preparation of 4-(4-trimethylsilyloxy-piperidin-1-yl)-3-fluoronitrobenzene

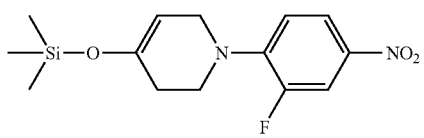

The mixture of 4-(4-oxo-piperidin-1-yl)-3-fluoronitrobenzene (0.250 mol), triethylamine (1.250 mol), trimethylsilylchloride (0.750 mol) in dimethylformamide was heated at 70° C. for 24 h. The solvent was removed under vacuum and to the residual mass was extracted with the ethyl acetate water mixture. The combined organic layer was dried and after removal of the solvent afforded title compound as a solid in 86% yield.

MS (M+1)=311 (MH+, 100%), M.F.=C14H19FN2O3Si.

Preparation-25

Preparation of 4-(3-fluoro-4-oxo-piperidin-1-yl)-3-fluoronitrobenzene

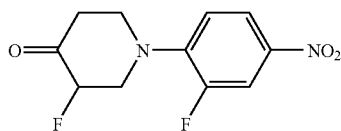

The mixture of 4-(4-trimethylsilyloxy-piperidin-1-yl)-3-fluoronitrobenzene (151 mmol), selectfluor (151 mmol) in acetonitrile was stirred for 4 hours. The solvent was removed under reduced pressure and to the residual mass was extracted into ethyl acetate water mixture. The combined organic layer was dried and removal of the solvent afforded title compound in 88% yield.

MS (M+1)=257 (MH+, 100%), M.F.=$C_{11}H_{10}F_2N_2O_3$.

Preparation-26

Preparation of 4-(4,4-dimethoxy-3-fluoropiperidin-1-yl)-3-fluoronitrobenzene

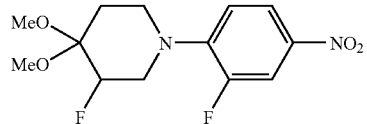

The mixture of 4-(3-fluoro-4-oxo-piperidin-1-yl)-3-fluoronitrobenzene (65 mmol), trimethylorthoformate (130 mmol), p-toluene-sulphonic acid monohydrate (67 mmol) in methanol was heated at 45° C. for 24 hours. Solvent was removed and residual mass was taken into ethyl acetate and saturated sodium bicarbonate solution mixture. The organic layer was dried and removal of the solvent afforded title compound as a solid in 78% yield.

MS (M+1)=303 (MH+, 100%), M.F.=$C_{13}H_{16}F_2N_2O_4$.

Preparation-27

Preparation of [4-(4,4-dimethoxy-3-fluoropiperidin-yl)-aminocarbonyloxymethyl]-3-fluorobenzene

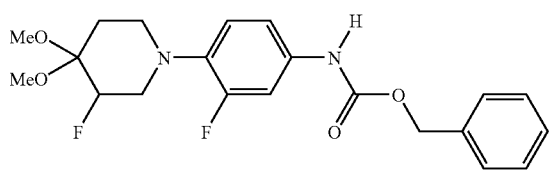

The suspension of 4-(4,4-dimethoxy-3-fluoropiperidin-yl)-3-fluoronitrobenzene (48 mmol), and 10% palladium on carbon (1 g) in tetrahydrofuran was stirred at room temperature under hydrogen atmosphere (200 psi) for 6 hour. The suspension was filtered. To the filtrate sodium bicarbonate (72 mmol) and benzyl chloroformate (58 mmol) was added and the reaction mixture was stirred at room temperature for 30 min. The solvent was removed and the residue was extracted with ethyl acetate and water mixture. The organic layer was dried and the residue was recrystallized from hexane:ehtyl acetate to give the title compound in 80% yield.

MS (M+1)=407 (MH+, 100%), M.F.=$C_{21}H_{24}F_2N_2O_4$.

Preparation-28

Preparation of (R)-{3-[4-(4,4-dimethoxy-3-fluoropiperidin-1-yl)-3-fluorophenyl]-2-oxo-oxazolidin-5-ylmethyl}-alcohol

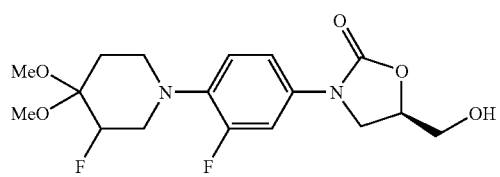

Butyl lithium (1.6 M in hexane, 27 ml) was added to the solution of [4-(4,4-dimethoxy-3-fluoropiperidin-yl)-aminocarbonyloxymethyl]-3-fluorobenzene (35.0 mmol) in tetrahydrofuran (250 ml) at −78° C. under an inert atmosphere. (R)-(−)-Glycidyl butyrate (37.1 mmol) was added to the reaction mixture and was stirred for 15 hours. The reaction mix-

Preparation-29

Preparation of (R)-{3-[4-(4-oxo-3-fluoropiperidin-1-yl)-3-fluorophenyl]-2-oxo-oxazolidin-5-ylmethyl}-alcohol

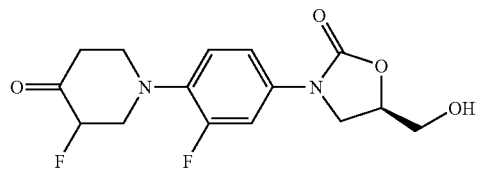

To the mixture of (R)-{3-[4-(4,4-dimethoxy-3-fluoropiperidin-1-yl)-3-fluorophenyl]-2-oxo-oxazolidin-5-ylmethyl}-alcohol (0.726 mmol), freshly fused zinc chloride (2.17 mmol), dimethyl sulphide (3.2 mmol), acetyl chloride (2.17 mmol) in tetrahydrofuaran (50 ml) was stirred at 40° C. for 4 days. To this reaction mixture extracted with the ethyl acetate water mixture and organic layer was dried over sodium sulfate. The removal of the solvent afforded a residue, which was chromatographed over silica gel afforded title compound in 54% yield.

MS (M+1)=327 (MH+, 100%), M.F.=$C_{15}H_{16}F_2N_2O$=.

Preparation-30

Prearration of (R)-{3-[4-(4,4-dimethoxy-3-fluoropiperidin-1-yl)-3-fluorophenyl]-2-oxo-oxazolidin-5-ylmethyl}-methanesulfonate

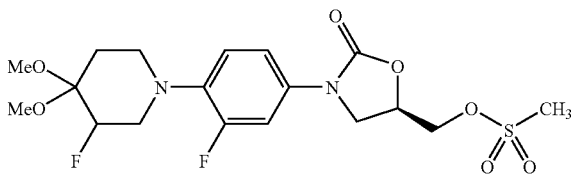

The mixture of (R)-{3-[4-(4,4-dimethoxy-3-fluoropiperidin-1-yl)-3-fluorophenyl]-2-oxo-oxazolidin-5-ylmethyl}-alcohol (29.6 mmol), triethylamine (65 mmol), methanesulphonyl chloride (41.5 mmol) in dichloromethane (100 ml) was stirred for 1 hour at room temperature. Reaction mixture was extracted with the dichloromethane water mixture. The combined organic layer was dried over sodium sulfate and removal of solvent afforded title compound in 86% yield.

MS (M+1)=451 (MH+, 100%), M.F.=$C_{18}H_{24}F_2N_2O_7S$.

Preparation-31

Preparation of (R)-{3-[4-(4-oxo-3-fluoropiperidin-1-yl)-3-fluorophenyl]-2-oxo-oxazolidin-5-ylmethyl}-methanesulfonate

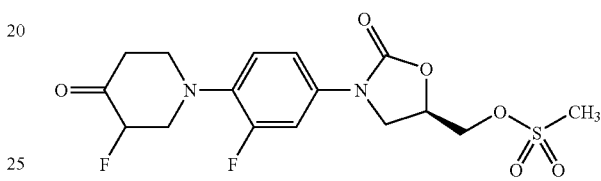

To the mixture of (R)-{3-[4-(4,4-dimethoxy-3-fluoropiperidin-1-yl)-3-fluorophenyl]-2-oxo-oxazolidin-5-ylmethyl}-methanesulfonate (0.5 mmol), freshly fused zinc chloride (1.5 mmol), dimethyl sulphide (2.5 mmol), acetyl chloride (0.5 mmol) in tetrahydrofuaran was stirred at 40° C. for 5 days. To this reaction mixture extracted with the ethyl acetate water mixture and organic layer was dried over sodium sulfate. The removal of the solvent afforded a residue which was chromatographed over silica gel afforded title compound in 55% yield.

MS (M+1)=405 (MH+, 100%), M.F.=$C_{16}H_{18}F_2N_2O_6S$.

Preparation-32

Preparation of (S)-{3-[4-(4,4-dimethoxy-3-fluoropiperidin-1-yl)-3-fluorophenyl]-2-oxo-oxazolidin-5-ylmethyl}-azide

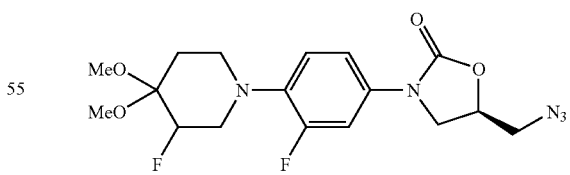

The mixture of sodium azide (67.0 mmol) and (R)-{3-[4-(4,4-dimethoxy-3-fluoropiperidin-1-yl)-3-fluorophenyl]-2-oxo-oxazolidin-5-ylmethyl}-methanesulfonate (27.0 mmol) in dimethylformamide was heated at 70° C. for 14 hours. The reaction mixture was poured on ice cold water, and the solid was filtered to afford title compound in 78% yield.

MS (M+1)=398 (MH+, 100%), M.F.=$C_{17}H_{21}F_2N_5O_4$.

Preparation-33

Preparation of (S)-{3-[4-(4-oxo-3-fluoropiperidin-1-yl)-3-fluorophenyl]-2-oxo-oxazolidin-5-ylmethyl}-azide

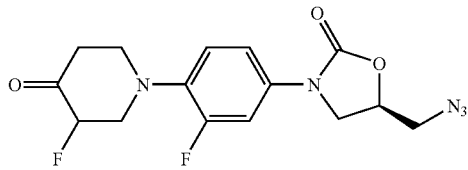

To the mixture of (S)-{3-[4-(4,4-dimethoxy-3-fluoropiperidin-1-yl)-3-fluorophenyl]-2-oxo-oxazolidin-5-ylmethyl}-azide (0.5 mmol), freshly fused zinc chloride (1.5 mmol), dimethyl sulphide (2.5 mmol), acetyl chloride (1.5 mmol) in tetrahydrofuaran (50 ml) was stirred at 40° C. for 4 days. To this reaction mixture extracted with the ethyl acetate water mixture and organic layer was dried over sodium sulfate. The removal of the solvent afforded a residue, which was chromatographed over silica gel afforded title compound in 69% yield.

MS (M+1)=352 (MH+, 100%), M.F.=$C_{15}H_{15}F_2N_5O_3$.

Preparation-34

Preparation of (S)-{3-[4-(4,4-dimethoxy-3-fluoropiperidin-1-yl)-3-fluorophenyl]-2-oxo-oxazolidin-5-ylmethyl}-amine

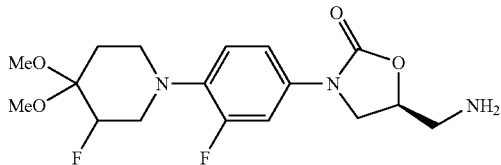

The suspension of (S)-{3-[4-(4,4-dimethoxy-3-fluoropiperidin-1-yl)-3-fluorophenyl]-2-oxo-oxazolidin-5-ylmethyl}-azide (25.2 mmol) and 10% palladium on carbon (1.0 g) was in ethyl acetate (150 ml) was stirred at a room temperature under hydrogen atmosphere for 10 hours. The reaction mixture was filtered and the filtrate was concentrated to give a residue, which was purified on silica gel column chromatography to provide title compound in 76% yield.

MS (M+1)=372 (MH+, 100%), M.F.=$C_{17}H_{23}F_2N_3O_4$.

Preparation-35

Preparation of (S)-{3-[4-(4,4-dimethoxy-3-fluoropiperidin-1-yl)-3-fluorophenyl]-2-oxo-oxazolidin-5-ylmethyl}-acetamide

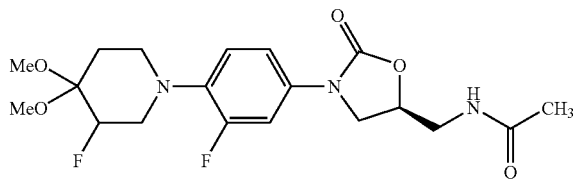

The mixture of (S)-{3-[4-(4,4-dimethoxy-3-fluoropiperidin-1-yl)-3-fluorophenyl]-2-oxo-oxazolidin-5-ylmethyl}-amine (6.73 mmol), pyridine (26.9 mmol), acetic anhydride (9.43 mmol) in ethyl acetate (25 ml) was stirred for 5 hours at room temperature. The reaction mixture was extracted with the ethyl acetate water mixture and combined organic layer was dried over sodium sulfate. The removal of the solvent afforded a residue, which was chromatographed over silica gel to give title compound in 58% yield.

MS (M+1)=414 (MH+, 100%), M.F.=$C_{19}H_{25}F_2N_3O_5$.

Preparation-36

Preparation of (S)-{3-[4-(4-oxo-3-fluoropiperidin-1-yl)-3-fluorophenyl]-2-oxo-oxazolidin-5-ylmethyl}-acetamide

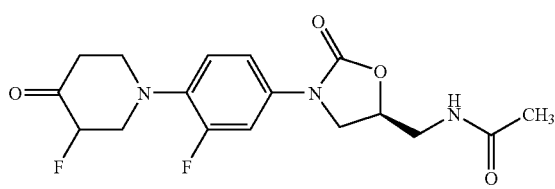

The mixture of (S)-{3-[4-(4,4-dimethoxy-3-fluoropiperidin-1-yl)-3-fluorophenyl]-2-oxo-oxazolidin-5-ylmethyl}-acetamide (1.0 mmol), freshly fused zinc chloride (3.1 mmol), dimethyl sulphide (5.1 mmol), acetyl chloride (3.1 mmol) in tetrahydrofuaran (50 ml) was stirred at 40° C. for 4 days. The reaction mixture was extracted with ethyl acetate water mixture and the organic layer was dried over sodium sulfate. The removal of the solvent afforded a residue, which was chromatographed over silica gel to give title compound in 61% yield.

MS (M+1)=368 (MH+, 100%), M.F.=$C_{17}H_{19}F_2N_3O_4$.

Preparation-37

Preparation of 4-(4,4-dimethoxy-3,3-difluoropiperidin-1-yl)-nitrobenzene

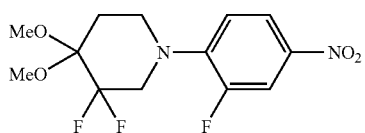

The mixture of 4-(3,3-difluoro-4-oxo-piperidin-1-yl)-nitrobenzene (25 mmol), trimethylorthoformate (51 mmol), p-toluene-sulphonic acid monohydrate (27 mmol) in methanol was heated at 45° C. for 24 hours. Solvent was removed and residual mass was taken into ethyl acetate and saturated sodium bicarbonate solution mixture. The organic layer was dried and removal of the solvent afforded title compound as a solid in 84% yield.

MS (M+1)=321 (MH+, 100%), M.F.=$C_{13}H_{15}F_3N_2O_4$.

Preparation-38

Preparation of [4-(4,4-dimethoxy-3,3-difluoropiperidin-yl)-aminocarbonyloxymethyl]-benzene

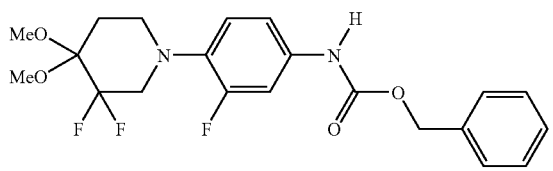

The suspension of 4-(4,4-dimethoxy-3,3-difluoropiperidin-yl)-nitrobenzene (20 mmol), and 10% palladium on carbon (1 g) in tetrahydrofuran was stirred at room temperature under hydrogen atmosphere (200 psi) for 6 hour. The suspension was filtered. To the filtrate sodium bicarbonate (40 mmol) and benzyl chloroformate (25 mmol) was added and the reaction mixture was stirred at room temperature for 30 min. The solvent was removed and the residue was extracted with ethyl acetate and water mixture. The organic layer was dried and the residue was recrystallized from hexane:ehtyl acetate to give the title compound in 75% yield.

MS (M+1)=425 (MH+, 100%), M.F.=$C_{21}H_{23}F_3N_2O_4$.

Preparation-39

Preparation of (R)-{3-[4-(4,4-dimethoxy-3,3-difluoropiperidin-1-yl)-phenyl]-2-oxo-oxazolidin-5-ylmethyl}-alcohol

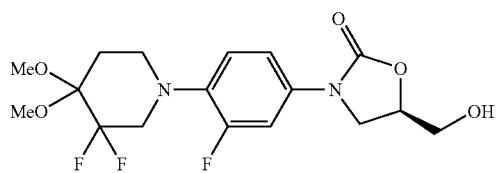

Butyl lithium (1.6 M in hexane, 27 ml) was added to the solution of [4-(4,4-dimethoxy-3,3-difluoropiperidin-yl)-aminocarbonyloxymethyl]-benzene (35.0 mmol) in tetrahydrofuran (250 ml) at −78° C. under an inert atmosphere. (R)-(−)-Glycidyl butyrate (37.1 mmol) was added to the reaction mixture and was stirred for 15 hours. The reaction mixture was extracted with the ethyl acetate water mixture. The combined organic layer was dried and removal of the solvent afforded a residue which was recrystallized from dichloromethane:hexane mixture to give title product in 80% yield.

MS (M+1)=391 (MH+, 100%), M.F.=$C_{17}H_{21}F_3N_2O_5$.

Preparation-40

Preparration of (R)-{3-[4-(4,4-dimethoxy-3,3-difluoropiperidin-1-yl)-phenyl]-2-oxo-oxazolidin-5-ylmethyl}-methanesulfonate

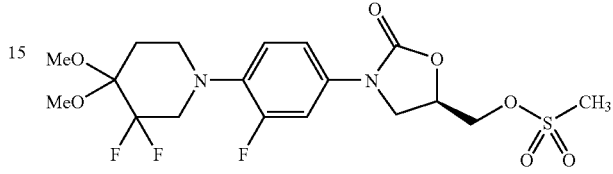

The mixture of (R)-{3-[4-(4,4-dimethoxy-3,3-difluoropiperidin-1-yl)-phenyl]-2-oxo-oxazolidin-5-ylmethyl}-alcohol (15 mmol), triethylamine (32 mmol), methanesulphonyl chloride (21 mmol) in dichloromethane was stirred for 1 hour at room temperature. Reaction mixture was extracted with the dichloromethane water mixture. The combined organic layer was dried over sodium sulfate and removal of solvent afforded title compound in 90% yield.

MS (M+1)=469 (MH+, 100%), M.F.=$C_{18}H_{23}F_3N_2O_7S$.

Preparation-41

Preparation of (S)-{3-[4-(4,4-dimethoxy-3,3-difluoropiperidin-1-yl)-phenyl]-2-oxo-oxazolidin-5-ylmethyl}-azide

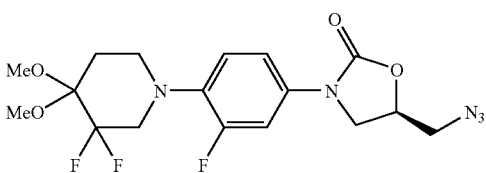

The mixture of sodium azide (26.0 mmol) and (R)-{3-[4-(4,4-dimethoxy-3,3-difluoropiperidin-1-yl)-phenyl]-2-oxo-oxazolidin-5-ylmethyl}-methanesulfonate (12.0 mmol) in dimethylformamide was heated at 70° C. for 14 hours. The reaction mixture was poured on ice cold water, and the solid was filtered to afford title compound in 88% yield.

MS (M+1)=416 (MH+, 100%), M.F.=$C_{17}H_{20}F_3N_5O_4$.

Preparation-42

Preparation of (S)-{3-[4-(4,4-dimethoxy-3,3-difluoropiperidin-1-yl)-phenyl]-2-oxo-oxazolidin-5-ylmethyl}-amine

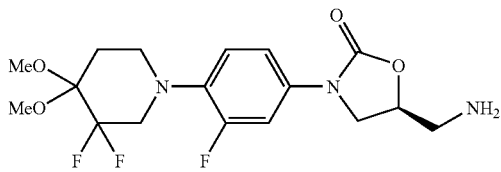

The suspension of (S)-{3-[4-(4,4-dimethoxy-3,3-difluoropiperidin-1-yl)-phenyl]-2-oxo-oxazolidin-5-ylmethyl}-azide (10 mmol) and 10% palladium on carbon (0.15 g) was in ethyl acetate was stirred at a room temperature under hydrogen atmosphere for 10 hours. The reaction mixture was filtered and the filtrate was concentrated to give a residue, which was purified on silica gel column chromatography to provide title compound in 88% yield.

MS (M+1)=390 (MH+, 100%), M.F.=$C_{17}H_{22}F_3N_3O_4$.

Preparation-43

Preparation of (S)-{3-[4-(4,4-dimethoxy-3,3-difluoropiperidin-1-yl)-phenyl]-2-oxo-oxazolidin-5-ylmethyl}-acetamide

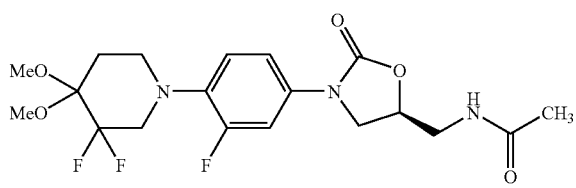

The mixture of (S)-{3-[4-(4,4-dimethoxy-3,3-difluoropiperidin-1-yl)-3-phenyl]-2-oxo-oxazolidin-5-ylmethyl}-amine (8 mmol), pyridine (32 mmol), acetic anhydride (16 mmol) in ethyl acetate was stirred for 5 hours at room temperature. The reaction mixture was extracted with the ethyl acetate water mixture and combined organic layer was dried over sodium sulfate. The removal of the solvent afforded a residue, which was chromatographed over silica gel to give title compound in 80% yield.

MS (M+1)=432 (MH+, 100%), M.F.=$C_{19}H_{24}F_3N_3O_5$.

Preparation-44

Preparation of (S)-{3-[4-(4-oxo-3,3-difluoropiperidin-1-yl)-phenyl]-2-oxo-oxazolidin-5-ylmethyl}-acetamide

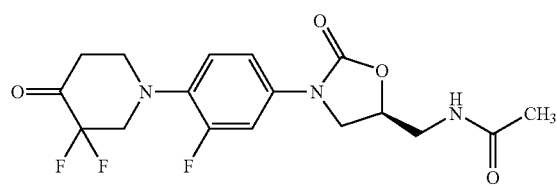

The mixture of (S)-{3-[4-(4,4-dimethoxy-3,3-difluoropiperidin-1-yl)-phenyl]-2-oxo-oxazolidin-5-ylmethyl}-acetamide (1.0 mmol), freshly fused zinc chloride (3.1 mmol), dimethyl sulphide (5.1 mmol), acetyl chloride (3.1 mmol) in tetrahydrofuaran (50 ml) was stirred at 40° C. for 4 days. The reaction mixture was extracted with ethyl acetate water mixture and the organic layer was dried over sodium sulfate. The removal of the solvent afforded a residue, which was chromatographed over silica gel to give title compound in 71% yield.

MS (M+1)=386 (MH+, 100%), M.F.=$C_{17}H18F_3N_3O_4$.

Preparation-45

Preparation of 4-[3-methyl-4-oxo-piperidin-1-yl]-3-fluoronitrobenzene

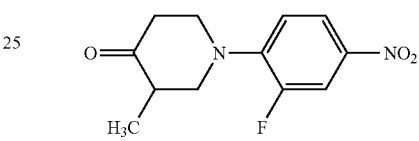

The mixture of 3-methyl-4-piperidone hydrochloride (0.085 mol), triethylamine (0.170 mol), 4-fluoronitrobenzene (0.085 mol) in chloroform was heated under reflux for 16 hours. The solvent was removed under vacuum and to the residue water was added and the precipitate was filtered to afford 4-[3-methyl-4-oxo-piperidin-1-yl]-3-fluoronitrobenzene in 76% yield.

MS (M+1)=253 (MH+, 100%), M.F.=$C_{12}H_{13}FN_2O_3$.

Preparation-46

Preparation of 4-[4-(1,4-dioxa-3-methyl-8-aza-spiro[4.5]-dec-8-yl)]-3-fluoronitrobenzene

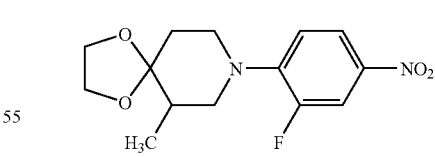

The mixture of 4-[3-methyl-4-oxo-piperidin-1-yl]-3-fluoronitrobenzene from step-1 (0.059 mol), ethylene glycol (1.09 mol) and p-toluenesulphonic acid monohydrate (0.014 mol) in toluene was heated to reflux for 5 hours. The reaction mixture was washed with water. The organic layer was evaporated to afford 4-[4-(1,4-dioxa-3-methyl-8-aza-spiro[4.5]-dec-8-yl)]-3-fluoronitrobenzene as a solid in 78% yield.

MS (M+1)=297 (MH+, 100%), M.F.=$C_{14}H_{17}FN_2O_4$.

Preparation-47

Preparation of [4-(1,4-dioxa-3-methyl-8-aza-spiro[4.5]-dec-8-yl)]-3-fluorophenyl-4-yl]-aminocarbonyloxymethyl]-benzene

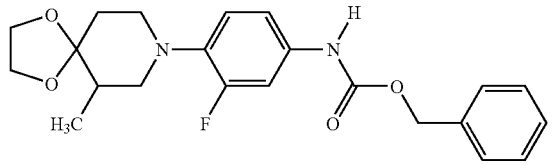

The suspension of 4-[4-(1,4-dioxa-3-methyl-8-aza-spiro[4.5]-dec-8-yl)]-3-fluoronitrobenzene (0.038 mol), 10% palladium on carbon (0.5 g) in tetrahydrofuran was stirred at room temperature under hydrogen atmosphere (400 psi) overnight. The reaction mixture filtered to remove the catalyst. To the filtrate, sodium bicarbonate (0.056 mol) and benzyl chloroformate (0.041 mol) was added at 0-5° C. and stirred at room temperature for 30 minutes. The solvent was evaporated under vacuum and the residue stirred with hexane. The precipitate was filtered to give the title compound in 89% yield.

MS (M+1)=401 (MH+, 100%), M.F.=$C_{22}H_{25}FN_2O_4$.

Preparation-48

Preparation of (R)-3-{4-(1,4-dioxa-3-methyl-8-aza-spiro[4.5]-dec-8-yl)]-3-fluorophenyl)-2-oxo-oxazolidin-5-ylmethyl}-alcohol

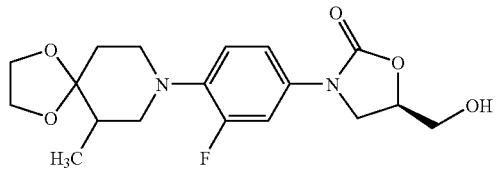

Butyl lithium (1.6 M in hexane, 180 ml) was added to the solution [4-(1,4-dioxa-3-methyl-8-aza-spiro[4.5]-dec-8-yl)]-3-fluorophenyl-4-yl]-aminocarbonyloxymethyl]-benzene (0.031 mol) in tetrahydrofuran at −78° C. (R)-(−)-Glycidyl butyrate (0.032 mol) was added to the reaction mixture and it was stirred overnight. The reaction mixture was extracted with the ethyl acetate after quenching with saturated aqueous ammonium chloride solution. The evaporation of solvent afforded title compound in 88% yield.

MS (M+1)=367 (MH+, 100%), M.F.=$C_{18}H_{23}FN_2O_5$.

Preparation-49

Preparation of R)-{3-[4-(4-(1,4-dioxa-3-methyl-8-aza-spiro[4.5]-dec-8-yl)-3-fluorophenyl]-2-oxo-oxazolidin-5-ylmethyl}-methanesulfonate

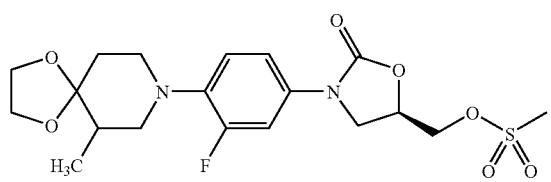

The mixture of (R)-{3-[4-(4-(1,4-dioxa-3-methyl-8-aza-spiro[4.5]-dec-8-yl)-3-phenyl]-2-oxo-oxazolidin-5-ylmethyl}-alcohol (0.194 mol), triethylamine (0.213 mmol), and methanesulphonyl chloride (0.232 mol) in 700 ml of dichloromethane was stirred for 1 hour. The reaction mixture was washed with 1 liter water. The organic layer was dried and evaporated under vacuum to afford title compound in 87% yield.

MS (M+1)=445 (MH+, 100%), M.F.=$C_{19}H_{25}FN_2O_7S$.

Preparation-50

Preparation of (S)-{3-[4-(4-(1,4-dioxa-3-methyl-8-aza-spiro[4.5]-dec-8-yl)-3-fluorophenyl]-2-oxo-oxazolidin-5-ylmethyl}-azide

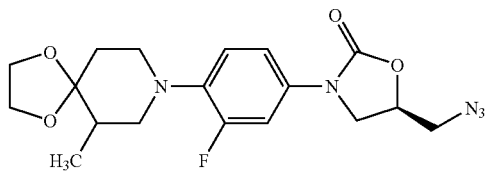

The mixture of (R)-{3-[4-(4-(1,4-dioxa-3-methyl-8-aza-spiro[4.5]-dec-8-yl)-3-fluorophenyl]-2-oxo-oxazolidin-5-ylmethyl}-methanesulfonate (0.16 mol), sodium azide (0.46 mol) in dimethylformamide (200 ml) was heated at 70° C. for 14 hours. The reaction mixture was cooled and poured in ice cold water. The precipitate was filtered to provide title compound in 85% yield.

MS (M+1)=392 (MH+, 100%), M.F.=$C_{18}H_{22}FN_5O_4$.

Preparation-51

Preparation of (S)-{3-[4-(4-(1,4-dioxa-3-methyl-8-aza-spiro[4.5]-dec-8-yl)-3-fluorophenyl]-2-oxo-oxazolidin-5-ylmethyl}-amine

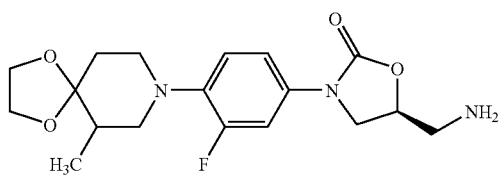

The suspension of (S)-{3-[4-(4,4-dimethoxy-3-fluoropiperidin-1-yl)-phenyl]-2-oxo-oxazolidin-5-ylmethyl}-azide (25.2 mmol) and 10% palladium on carbon (1.0 g) was in ethyl acetate was stirred at a room temperature under hydrogen atmosphere for 10 hours. The reaction mixture was filtered and the filtrate was concentrated to give a residue, which was purified on silica gel column chromatography to provide title compound in 85% yield.

MS (M+1)=366 (MH+, 100%), M.F.=$C_{18}H_{24}FN_3O_4$.

Preparation-52

Preparation of (S)-{3-[4-(4-(3-methyl-4-oxo-8-aza-spiro[4.5]-dec-8-yl)-3-fluorphenyl]-2-oxo-oxazolidin-5-ylmethyl}-amine

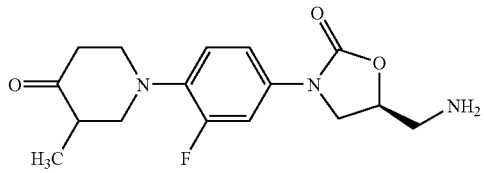

The mixture of (S)-{3-[4-(4-(1,4-dioxa-3-methyl-8-aza-spiro[4.5]-dec-8yl)-3-fluorophenyl]-2-oxo-oxazolidin-5-yl-methyl}-amine (0.016 mol), p-toluene sulfonic acid (0.032 mol) in acetone water (300 ml, 40:60) mixture was refluxed for 6 hours. The reaction mixture was concentrated under vacuum and treated with saturated aqueous sodiumbicarbonate solution. The precipitate was filtered to afford title compound 78% yield.

MS (M+1)=322 (MH+, 100%), M.F.=$C_{16}H_{20}FN_3O_3$.

Preparation-53

Preparation of (S)-N-{3-[4-(4-(1,4-dioxa-3-methyl-8-aza-spiro[4.5]-dec-8-yl)-3-fluorophenyl]-2-oxo-oxazolidin-5-ylmethyl}-acetamide

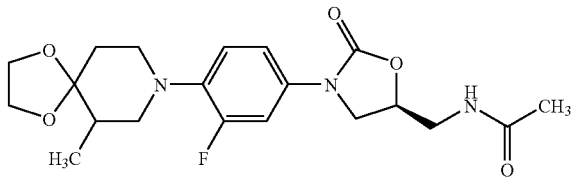

The suspension of (S)-{3-[4-(4-(1,4-dioxa-3-methyl-8-aza-spiro[4.5]-dec-8-yl)-3-fluorophenyl]-2-oxo-oxazolidin-5-ylmethyl}-azide (0.153 mol), 10% palladium on carbon (7 g), pyridine (0.45 mol), acetic anhydride (0.18 mol) in 700 ml ethyl acetate was stirred at 400 psi hydrogen gas pressure overnight. The suspension was filtered. Filtrate was purified to provide title compound in 70% yield.

MS (M+1)=408 (MH+, 100%), M.F.=$C_{20}H_{26}FN_3O_5$.

Preparation-54

Preparation of (S)-N-{3-[4-(3-methyl-4-oxo-piperidin-1-yl)-3-fluorophenyl]-2-oxo-oxazolidin-5-ylmethyl}-acetamide

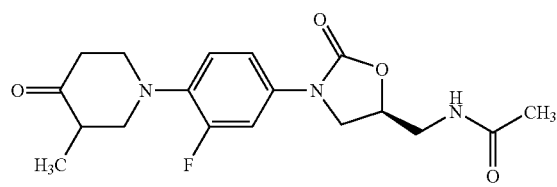

The (S)-N-{3-[4-(4-(1,4-dioxa-3-methyl-8-aza-spiro[4.5]-dec-8-yl)-3-fluorophenyl]-2-oxo-oxazolidin-5-ylmethyl}-acetamide (0.040 mol), p-toluene sulfonic acid (0.080 mol) in acetone water (350 ml, 40:60) mixture was refluxed for 5 hours. The reaction mixture was concentrated under vacuum and treated with saturated aqueous sodiumbicarbonate solution. The precipitate was filtered to afford keto oxazolidinone acetamide compound 76% yield.

MS (M+1)=364 (MH+, 100%), M.F.=$C_{18}H_{22}FN_3O_4$.

Preparation-55

Preparation of 4-[3,3-dimethyl-4-oxo-piperidin-1-yl]-3-fluoronitrobenzene

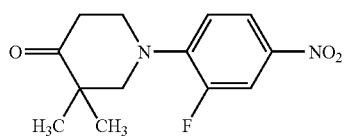

The mixture of 3,3-dimethyl-4-piperidone hydrochloride (0.085 mol), triethylamine (0.170 mol), 4-fluoronitrobenzene (0.085 mol) in chloroform was heated under reflux for 16 hours. The solvent was removed under vacuum and to the residue water was added and the precipitate was filtered to afford 4-[3-methyl-4-oxo-piperidin-1-yl]-3-fluoronitrobenzene in 76% yield.

MS (M+1)=267 (MH+, 100%), M.F.=$C_{13}H_{15}FN_2O_3$.

Preparation-56

Preparation of 4-[4-(1,4-dioxa-3,3-dimethyl-8-aza-spiro[4.5]-dec-8-yl)]-3-fluoronitrobenzene

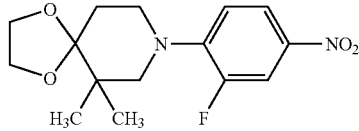

The mixture of 4-[3,3-dimethyl-4-oxo-piperidin-1-yl]-3-fluoronitrobenzene from step-1 (0.059 mol), ethylene glycol (0.109 mol) and p-toluenesulphonic acid monohydrate (0.014 mol) in toluene was heated to reflux for 5 hours. The reaction mixture was washed with water. The organic layer was evaporated to afford 4-[4-(1,4-dioxa-3-methyl-8-aza-spiro[4.5]-dec-8-yl)]-3-fluoronitrobenzene as solid in 78% yield.

MS (M+1)=311 (MH+, 100%), M.F.=$C_{15}H_{19}FN_2O_4$.

Preparation-57

Preparation of [4-(1,4-dioxa-3,3-methyl-8-aza-spiro[4.5]-dec-8-yl)]-3-fluorophenyl-4-yl]-aminocarbonyloxymethyl]-benzene

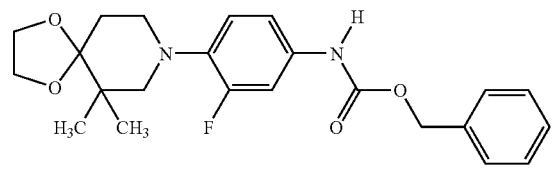

The suspension of 4-[4-(1,4-dioxa-3,3-dimethyl-8-aza-spiro[4.5]-dec-8-yl)]-3-fluoronitrobenzene (0.038 mol), 10% palladium on carbon (0.5 g) in tetrahydrofuran was stirred at room temperature under hydrogen atmosphere (400 psi) overnight.

The reaction mixture filtered to remove the catalyst. To the filtrate, sodium bicarbonate (0.056 mol) and benzyl chloroformate (0.041 mol) was added at 0-5° C. and stirred at room temperature for 30 minutes. The solvent was evaporated under vacuum and the residue stirred with hexane. The precipitate was filtered to give the title compound in 89% yield.

MS (M+1)=415 (MH+, 100%), M.F.=$C_{23}H_{27}FN_2O_4$.

Preparation-58

Preparation of (R)-3-{4-(1,4-dioxa-3,3-dimethyl-8-aza-spiro[4.5]-dec-8-yl)]-3-fluorophenyl)--2-oxo-oxazolidin-5-ylmethyl}-alcohol

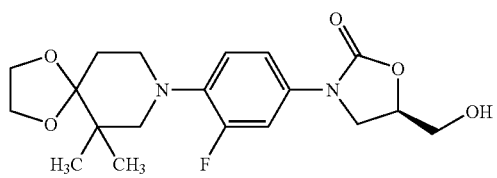

Butyl lithium (1.6 M in hexane, 180 ml) was added to the solution [4-(1,4-dioxa-3,3-dimethyl-8-aza-spiro[4.5]-dec-8-yl)]-3-fluorophenyl-4-yl]-aminocarbonyloxymethyl]-benzene (0.031 mol) in tetrahydrofuran at −78° C. (R)-(−)-Glycidyl butyrate (0.032 mol) was added to the reaction mixture and it was stirred overnight. The reaction mixture was extracted with the ethyl acetate after quenching with saturated aqueous ammonium chloride solution.

The evaporation of solvent afforded title compound in 88% yield.

MS (M+1)=381 (MH+, 100%), M.F.=$C_{19}H_{25}FN_2O_5$.

Preparation-59

Preparation of R)-{3-[4-(4-(1,4-dioxa-3,3-dimethyl-8-aza-spiro[4.5]-dec-8-yl)-3-fluorophenyl]-2-oxo-oxazolidin-5-ylmethyl}-methanesulfonate

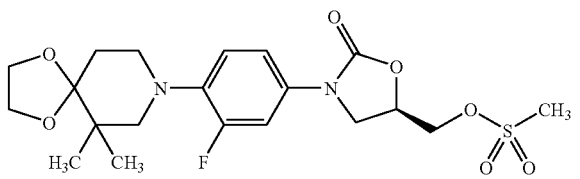

The mixture of (R)-{3-[4-(4-(1,4-dioxa-3,3-dimethyl-8-aza-spiro[4.5]-dec-8-yl)-3-phenyl]-2-oxo-oxazolidin-5-yl-methyl}-alcohol (0.194 mol), triethylamine (0.213 mmol), and methanesulphonyl chloride (0.232 mol) in 700 ml of dichloromethane was stirred for 1 hour. The reaction mixture was washed with 1 liter water. The organic layer was dried and evaporated under vacuum to afford title compound in 87% yield.

MS (M+1)=459 (MH+, 100%), M.F.=$C_{20}H_{27}FN_2O_7S$.

Preparation-60

Preparation of (S)-{3-[4-(4-(1,4-dioxa-3,3-dimethyl-8-aza-spiro[4.5]-dec-8-yl)-3-fluorophenyl]-2-oxo-oxazolidin-5-ylmethyl}-azide

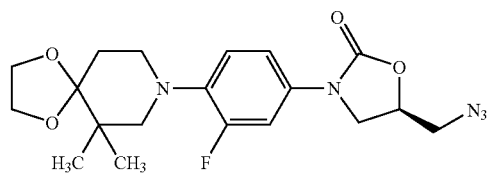

The mixture of (R)-{3-[4-(4-(1,4-dioxa-3,3-dimethyl-8-aza-spiro[4.5]-dec-8-yl)-3-fluorophenyl]-2-oxo-oxazolidin-5-ylmethyl}-methanesulfonate (0.16 mol), sodium azide (0.46 mol) in dimethylformamide (200 ml) was heated at 70° C. for 14 hours. The reaction mixture was cooled and poured in ice cold water. The precipitate was filtered to provide title compound in 85% yield.

MS (M+1)=406 (MH+, 100%), M.F.=$C_{19}H_{24}FN_5O_4$.

Preparation-61

Preparation of (S)-N-{3-[4-(4-(1,4-dioxa-3,3-dimethyl-8-aza-spiro[4.5]-dec-8-yl)-3-fluorophenyl]-2-oxo-oxazolidin-5-ylmethyl}-acetamide

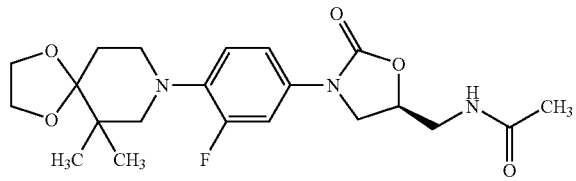

The suspension of (S)-{3-[4-(4-(1,4-dioxa-3,3-dimethyl-8-aza-spiro[4.5]-dec-8-yl)-3-fluorophenyl]-2-oxo-oxazolidin-5-ylmethyl}-azide (0.153 mol), 10% palladium on carbon (7 g), pyridine (0.45 mol), acetic anhydride (0.18 mol) in 700 ml ethyl acetate was stirred at 400 psi hydrogen gas pressure overnight. The suspension was filtered. Filtrate was purified to provide title compound in 70% yield.

MS (M+1)=422 (MH+, 100%), M.F.=$C_{21}H_{28}FN_3O_5$.

Preparation-62

Preparation of (S)-N-{3-[4-(3,3-dimethyl-4-oxo-piperidin-1-yl)-3-fluorophenyl]-2-oxo-oxazolidin-5-ylmethyl}-acetamide

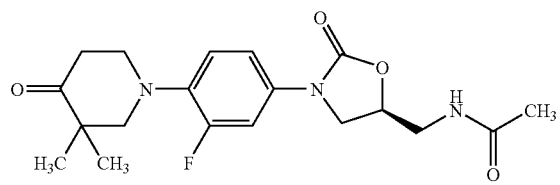

The (S)-N-{3-[4-(4-(1,4-dioxa-3,3-dimethyl-8-aza-spiro[4.5]-dec-8-yl)-3-fluorophenyl]-2-oxo-oxazolidin-5-ylmethyl}-acetamide (0.040 mol), p-toluene sulfonic acid (0.080 mol) in acetone water (350 ml, 40:60) mixture was refluxed for 5 hours. The reaction mixture was concentrated under vacuum and treated with saturated aqueous sodiumbicarbonate solution. The precipitate was filtered to afford keto oxazolidinone acetamide compound 76% yield.

MS (M+1)=378 (MH+, 100%), M.F.=$C_{19}H_{24}FN_3O_4$.

The Table 1 below shows the linezolid MIC values for the sensitive and the corresponding resistant strains as well as the site of mutation in their ribosomal RNA.

TABLE 1

| Strains | Linezolid MIC (µg/ml) | Mutation in 23 S rRNA |
|---|---|---|
| S. pneumoniae ATCC 6303 | 0.8 | — |
| S. pneumoniae ATCC 6303 LR | 25 | A2160G |
| S. aureus Smith | 1.56 | — |
| S. aureus Smith LR | 50 | G2447U |
| MRSA 032 | 1.56 | — |
| MRSA 032 LR | 25 | G2447U |

A further embodiment in support of the invention is the result derived from a CoMFA 3D-QSAR study carried out on the compounds of the invention. The study and the results obtained are briefed described below.

Three-dimensional Quantitative Structure Activity Relationship of (3D-QSAR) of Oxazolidinone Antibacterials Comparative molecular field analysis (CoMFA) a three-dimensional quantitative structure activity relationship technique was applied to series of oxazolidinone antibacterials to understand pharmacophoric factors necessary for optimal activity. CoMFA technique derives the relationship between steric and electrostatic fields of the molecules and their biological activity. Minimum inhibitory concentration against *Staphylococcus aureus* (MRSA 032 strain) was used as biological activity.

Computational Methods

Study was performed using Sybyl 6.6 (Tripos Inc. St. Louis Mo.) molecular modeling software. All the molecules were constructed and assigned Gasteiger-Huckel charges. All the molecules were minimized using Conjugate Gradient method. Molecules were aligned using rigid fit method with oxazolidinone ring as a template. Biological activity is expressed as log (1/MIC) in molar units. CoMFA fields were calculated for all the molecules and CoMFA field values were correlated with biological activity using partial-least squares (PLS) method. PLS was used to determine optimum number of components and these were used to calculate $r^2$ and F-value.

Statistical Results From CoMFA Analysis Of Oxazolidinones.

|  | Series 1 (Literature compounds) | Series 2 (Compounds of the invention) |
|---|---|---|
| Cross-validated $r^2$ ($r^2_{cv}$) | 0.490 | 0.535 |
| Optimum number of components | 7 | 2 |

-continued

Statistical Results From CoMFA Analysis Of Oxazolidinones.

|  | Series 1 (Literature compounds) | Series 2 (Compounds of the invention) |
|---|---|---|
| $r^2$ value | 0.796 | 0.700 |
| F-value | 104.15 | 75.48 |
| Steric contributions | 44.7 | 62.7 |
| Electrostatic contributions | 55.3 | 37.3 |

The results clearly show that in the case of the prior art literature molecules the steric contributions are less than the electrostatic contributions. In contrast, for the compounds of the present invention as opposed to the prior art, and thus non-obvious, the steric contributions are more than one and half times more than the electrostatic contributions.

EXAMPLES

The following examples illustrate the methods of selection of resistant mutant strains and are provided only as examples, but not to limit the scope.

Example A

Selection of Linezolid (LNZ) Resistant Mutants of Methicillin Resistant *Staphylococcus aureus*-32 (MRSA-32) and *Streptococcus pneumoniae* 6303 (SPN 6303) in Murine Infections.

Method

Linezolid resistant mutants of MRSA-32 and SPN 6303 were recovered while studying in vivo efficacy of linezolid in immunocompetent Swiss mice. Infecting doses of organisms given by intraperitoneal route in 5% hog gastric mucin were $10^3$-$10^4$ CFU (colony forming units)/animal for SPN 6303 and $10^8$ CFU/animal for MRSA-32. In case of MRSA-32, Linezolid was administered by oral route, 1 and 4 h post infection, BID (twice a day) for 1 day and for SPN 6303 BID for 2 days. Mice dying at the highest dose of Linezolid were dissected to recover organisms from heart and liver for MRSA-32 and from lung for SPN 6303 by plating on blood agar containing Linezolid at a concentration of 4×MIC (Minimum Inhibitory Concentration). MICs of Methicillin Resistant *Staphylococcus aureus*-32 Linezolid resistant (MRSA-32 LNZR), *S. pneumoniae* 744 Linezolid resistant (SPN 744 LNZR) and parent Linezolid sensitive strains MRSA-32 and SPN 6303 were determined for Linezolid by NCCLS agar dilution method. In vivo expression of Linezolid resistance by mutants was further confirmed by determining Linezolid $ED_{50}$ (Efficacy dose at which 50% of animals show mortality) values for mutants and parent strains in mouse systemic infection model.

Results

MICs of Linezolid for parent Linezolid sensitive strains of MRSA-32 and SPN 6303 and were 1.56 and 0.8 mcg/ml respectively. However, mutant strains MRSA-32 LNZR and SPN 744 LNZR recovered from mice had higher MICs of 50 and 25 mcg/ml respectively. $ED_{50}$ values of Linezolid for MRSA-32 and SPN 6303 were raised from 5 and 75 mg/kg to 100 and >200 mg/kg for the corresponding mutant strains.

Example B

**Method used for Selecting LNZ Resistant Mutant of *Enterococcus faecium* ATCC 19434**

*E. faecium* ATCC 19434 strain at a cell density of $10^6$/ml was inoculated in Mueller Hinton broth medium containing Linezolid at a concentration of 5 and 7.5 mcg/ml. The stationary culture was incubated at 37° C. and inspected at every 24 hours to assess the formation of turbidity due to the onset of bacterial growth. Following an extended incubation for 96-120 hrs turbidity development was noticed in a flask containing medium incorporated with linezolid at 5 & 7.5 mcg/ml. A 50 microliter sample of turbid flask was plated on Mueller Hinton agar medium incorporated with linezolid at 7.5 mcg/ml. The agar plates were incubated for 48 hours at 37° C. for the formation of discrete colonies of linezolid-resistant strain of *E. faecium* (*E. faecium* 367 LNZR). MICs of resistant mutant *E. faecium* 367 LNZR and parent strain *E. faecium* ATCC 19434 were determined for linezolid by NCCLS method.

Results

MIC value of Linezolid sensitive strain *E. facium* ATCC 19434 increased from 1.56 mcg/ml to 25 mcg/ml for *E. faecium* 367 LNZR, on becoming resistant to Linezolid.

Antibacterial Activity

The compounds of the invention have distinctive antibacterial activities over the compounds of the prior art. Examples of such activity are provided below. The methods for subjecting the compounds of the invention to various antimicrobial activity tests, in which they exhibited antimicrobial activity are also described.

Test Examples

Test Example 1

Minimum Inhibitory Concentration (MIC) Determination

Overnight grown cultures of *S. aureus* organisms in Tryptic Soya broth were diluted in Mueller Hinton Broth to give optical density matching with MacFarland tube 0.5 standard. Cultures were further diluted 1:10 in Mueller Hinton broth. Using Denley's mutipoint inoculator, $10^4$ cells were deposited on Mueller Hinton agar (Difco) containing range of 2 fold dilutions of test compounds. These plates were incubated for 24 hrs at 35° C. and MIC results recorded. MIC is defined as minimum drug concentration that inhibits test organisms. For determining MIC of test compounds against *Streptococcus pneumoniae*, Mueller Hinton agar containing 5% sheep blood was employed.

The MIC values for representative compounds of the invention against linezolid resistant (LNZR) strains *S. aureus* MRSA-32 LNZR, SPN 744 LNZR and *E.faecium* 367 LNZR are shown in Table-2.

TABLE 2

MICs against linezolid resistant strains (MIC µg/ml)

| Example No. | MRSA 32 LNZR | SPN744 LNZR | E. faecium 367 LNZR |
| --- | --- | --- | --- |
| 3 | 25.0 | 12.5 | 25.0 |
| 31 | 12.5 | 12.5 | 6.25 |
| 32 | 12.5 | 6.25 | 6.25 |
| 45 | 3.12 | 3.12 | ND |
| 46 | 6.25 | 6.25 | 1.56 |
| 51 | 3.12 | 3.12 | 1.56 |
| 56 (E) | 12.5 | 6.25 | 6.25 |
| 56 (Z) | 25 | 12.5 | 6.25 |
| 57 | 12.5 | 6.25 | 6.25 |
| 60 | 6.25 | 3.12 | 1.56 |
| 67 | 12.5 | 6.25 | 3.12 |
| 68 | 6.25 | 3.12 | 3.12 |
| 74 | 25 | 6.25 | 6.25 |
| 77 | 12.5 | 6.25 | 6.25 |
| 84 | 1.56 | 1.56 | 1.56 |
| 89 | 25 | 12.5 | 6.25 |
| 90 | 12.5 | 6.25 | 3.12 |
| 93 | 6.25 | 3.12 | 1.56 |
| 96 | 12.5 | 6.25 | 3.12 |
| 115 | 12.5 | 6.25 | 3.12 |
| 117 | 12.5 | 6.25 | 3.12 |
| 121 | 6.25 | 1.56 | ND |
| 160 | 6.25 | 3.12 | ND |
| Linezolid | >25 | 25 | >25 |

ND: not done

Test Example 2

The MIC values for representative compounds of the invention against Linezolid sensitive MRSA-32, Linezolid sensitive SPN 49619 are shown in Table-3.

TABLE 3

MICs against linezolid sensitive strains (MIC µg/ml)

| Example No. | MRSA 32 | SPN 49619 |
| --- | --- | --- |
| 3 | 1.56 | 0.8 |
| 31 | 0.8 | 0.8 |
| 32 | 0.8 | 0.8 |
| 45 | 0.2 | 0.2 |
| 46 | 0.2 | 0.2 |
| 47 | 0.8 | 0.4 |
| 51 | 0.4 | 0.2 |
| 56 (Z) | 0.8 | 0.8 |
| 56 (E) | 0.8 | 0.8 |
| 60 | 0.25 | 0.1 |
| 67 | 0.8 | 0.4 |
| 68 | 0.4 | 0.4 |
| 79 | 0.80 | 0.8 |
| 84 | 0.40 | 0.2 |
| 90 | 0.80 | 0.4 |
| 93 | 0.40 | 0.2 |
| 96 | 0.8 | 0.8 |
| 105 | 0.80 | 0.8 |
| 115 | 0.80 | 0.8 |
| 117 | 0.8 | 0.4 |
| 118 | 0.80 | 0.4 |
| 119 | 0.40 | 0.8 |
| 120 | 0.80 | 0.8 |
| 121 | 0.40 | 0.2 |
| 160 | 0.4 | 0.2 |
| Linezolid | 1.56 | 0.8 |

Test Example 3

Bactericidal Activity Vs Bacteriostatic Activity

Killing effect study of linezolid and test compound was carried out against *Enterococcus faecalis* 416 strain. Test organism was appropriately diluted in 20 ml Muller Hinton broth containing 5 mcg/ml of linezolid and test compound in 50 ml conical flasks. The initial inoculum was adjusted to $10^6$ CFU (colony forming units) per ml. The flasks were kept on shaker in close cabinet at 35° C. Aliquots were drawn at 112 hours and cell count was determined to assess the extent of loss in viability.

Results

In case of Linezolid, the initial count of $10^6$ CFU/ml was increased to $10^9$ CFU/ml, indicating that there was no static or cidal action exerted by linezolid. However, flasks containing a representative compound of the invention showed excellent cidal potential by reducing initial count of $10^6$ CFU/ml to $10^3$ CFU/ml. This 3 log kill amounts to 99.9% kill of test organism.

TABLE 4

Bactericidal potential of Compounds of the invention

*E. faecalis* 416 (CFU/ml)

| Example No | Initial Count | Final Count (112 h) |
|---|---|---|
| 3 | $10^6$ | $10^6$ |
| 9 | $10^6$ | $10^3$ |
| 46 | $10^6$ | $<10^2$ |
| 51 | $10^6$ | $<10^2$ |
| 96 | $10^6$ | $<10^2$ |
| 160 | $10^6$ | $<10^2$ |
| Linezolid | $10^6$ | $10^8$ |

Test Example 4

Low Propensity to Resistance Development

Method

*Enterococcus faecalis* 416 strain at $10^8$ CFU density level was spirally plated on Mueller Hinton agar containing 5 mcg/ml each of linezolid and representative compound of the invention. Plates were incubated at 35° C. for 48 hours and number of resistant colonies developed in presence of respective compounds were counted by automated counter.

Results

TABLE 5

Low propensity of compounds of invention towards resistance development

| Example No | No. of colonies/plate Compound concentration—5 mcg/ml *E. faecalis* 416 |
|---|---|
| 3 | 0 |
| 9 | 0 |
| 31 | 0 |
| 32 | 0 |
| 46 | 0 |

TABLE 5-continued

Low propensity of compounds of invention towards resistance development

| Example No | No. of colonies/plate Compound concentration—5 mcg/ml *E. faecalis* 416 |
|---|---|
| 47 | 0 |
| 51 | 0 |
| 56 | 0 |
| 74 | 0 |
| 90 | 0 |
| 96 | 0 |
| 159 | $1.5 \times 10^1$ |
| 160 | 0 |
| Linezolid | $1.2 \times 10^2$ |

Compounds of the invention show absence of or very low frequency of emergence of resistant colonies, in comparison to linezolid. This result is indicative of the superior curing effect of the compounds of the invention compared to linezolid for the treatment of enterococcal infections.

Test Example 5

Mutant Prevention Concentration (MPC) Determination

Method

Clinical isolate *Enterococcus faecalis* 416 was spirally plated on Tryptic Soya agar (TSA) plate containing various 2 fold dilutions each of a representative compound of the invention and Linezolid so as to give $10^9$ CFU/plate. After incubation at 35° C. for 48 hours, the CFU on each plate was determined. MPC is defined as minimum concentration of drug that prevents mutant colonies on respective antibiotic containing plate.

Results

TABLE 6

MPC of compounds of invention for *Enterococcus faecalis* 416 strain

| Example- No | *E. faecalis* 416 |
|---|---|
| 3 | 12.5 |
| 9 | 6.25 |
| 32 | 6.25 |
| 46 | 1.56 |
| 51 | 1.56 |
| 96 | 6.25 |
| Linezolid | 12.5 |

Conclusion

The lower MPC values are indicative of superior curing effect of compounds of the invention compared to linezolid in the treatment of enterococcal infections.

The following examples illustrate the methods of preparation of the compounds of the invention are provided only as examples, but not to limit the scope of the compounds of the invention.

Examples

Example 1

Preparation of (S)-{3-[4-(4-cyanomethylidene-piperidin-1-yl)-phenyl]-2-oxo-oxazolidin-5-ylmethyl}-azide

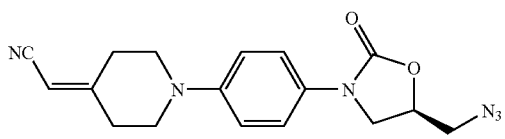

The mixure of triethylamine (13.8 mmol), lithium bromide (8.2 mmol) and diethylcyanomethylphosphonate (7.2 mmol) in 25 ml tetrahydrofuran was stirred for 20 minutes at room temperature. To the suspension, (S)-{3-[4-(4-oxo-piperidin-1-yl)-phenyl]-2-oxo-oxazolodin-5-ylmethyl}-azide (6.9 mmol) was added. The reaction mixture stirred for 5 hours.

The suspension was filtered and the filtrate was treated with water and extracted with ethyl acetate. The combined organic layer was dried and evaporated to give a residue which purified by silica gel column chromatography to provide the titled compound in 91% yield.

M.P. 80-82° C. and MS (M+1)=339 (MH+, 100%), M.F.=$C_{17}H_{18}N_6O_2$.

Example 2

Preparation of (S)-N-{3-[4-(4-cyanomethylidene-piperidin-1-yl)-phenyl]-2-oxo-oxazolidin-5-ylmethyl}-formamide

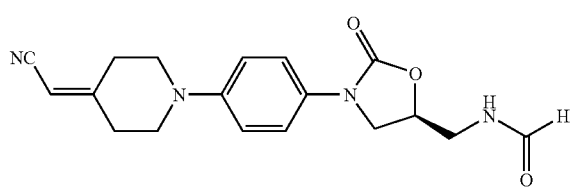

Step-1

To a mixture of (S)-{3-[4-(4-cyanomethylidene-piperidin-1-yl)-phenyl]-2-oxo-oxazolidin-5-ylmethyl}-azide (2.94 mmol), triphenylphosphine (3.81 mmol) was stirred for 3 hours. It was refluxed by adding water overnight. Removal of solvent and purification of the product on silica gel column chromatography provided (S)-{3-[4-(4-cyanomethylidene-piperidin-1-yl)-phenyl]-2-oxo-oxazolidin-5-ylmethyl}-amine in 71% yield.

Step-2

The solution of (S)-{3-[4-(4-cyanomethylidene-piperidin-1-yl)-phenyl]-2-oxo-oxazolidin-5-ylmethyl}-amine (2.3 mmol) in ethyl formate (10 ml) was heated at 80° C. over night. The solvent was evaporated under vacuum and the residue obtained was chromatographed over silica gel to afford the titled compound in 68% yield.

MS (M+1)=341 (MH+, 100%), M.F.=$C_{18}H_{20}N_4O_3$.

Example 3

Preparation of (S)-N-{3-[4-(4-cyanomethylidene-piperidin-1-yl)-phenyl]-2-oxo-oxazolidin-5-ylmethyl}-acetamide;

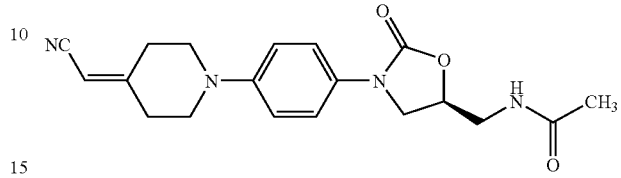

The titled compound was obtained as per Example-1 by using (S)-{3-[4-(4-oxo-piperidin-1-yl)-phenyl]-2-oxo-oxazolidin-5-ylmethyl}-acetamide in 80% yield.

M.P. 168-170° C. and MS (M+1)=355 (MH+, 100%), M.F.=$C_{19}H_{22}N_4O_3$.

Example 4

Preparation of (S)-1-{3-[4-(4-cyanomethylidene-piperidin-1-yl)-phenyl]-2-oxo-oxazolidin-5-ylmethyl}-4-carboxyethyl-1,2,3-triazole

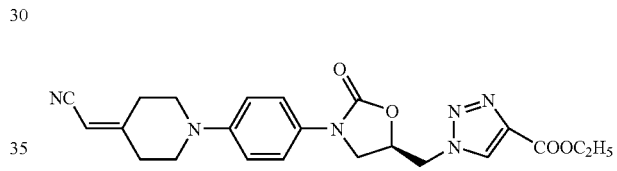

The mixture of compound of Example 1 (2.05 mmol), ethyl propiolate (4.21 mmol), in toluene (10 ml) was heated under reflux for 4 hours. The solvent was removed under vacuum. The residue was triturated with the hexane and filtered to provide a isomeric mixture of two compounds. The column chromatographic purification on silica gel afforded the titled compound in 70% yield.

M.P. 120-122° C. and MS (M+1)=437 (MH+, 100%), M.F.=$C_{22}H_{24}N_6O_4$.

Example 5

Preparation of (S)-1-{3-[4-(4-cyanomethylidene-piperidin-1-yl)-phenyl]-2-oxo-oxazolidin-5-ylmethyl}-4-cyano-1,2,3-triazole

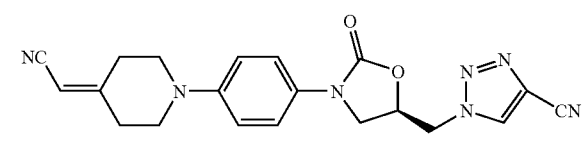

Step-1

The mixture of (S)-1-{3-[4-(4-cyanomethylidene-piperidin-1-yl)-phenyl]-2-oxo-oxazolidin-5-ylmethy}4-carboxyethyl-1,2,3-triazole (1.14 mmol), ammonium hydroxide (60 ml) in acetonitrile (10 ml) was heated at 50° C. for 3 hours. The solvent was removed under reduced pressure. The solid compound obtained was dried under vacuum to afford 4-carboxamide 1,2,3-triazole compound in 58% yield.

Step-2

To a suspension of the 4-carboxamide 1,2,3-triazole compound (0.82 mmol), pyridine (2.06 mmol), trifluoroacetic anhydride (0.23 ml, 1.65 mmol) in dichloromethane (10 ml) was stirred at room temperature for 15 hours. The reaction mixture treated with saturated aqueous solution of sodium bicarbonate. Organic layer was dried and removal of solvent and purification of residue over a silica gel column chromatography furnished the titled compound in 51% yield.

M.P. 186-188° C. and MS (M+1)=390 (MH$^+$, 100%), M.F.=$C_{20}H_{19}N_7O_2$.

Example 6

Preparation of (R)-{3-[4-(4-cyanomethylidene-piperidin-1-yl)-phenyl]-2-oxo-oxazolidin-5-ylmethyl}-methanesulphonate;

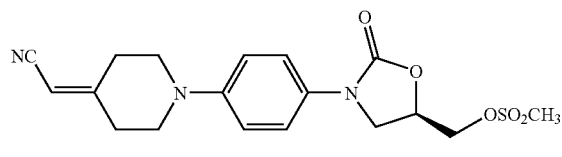

The (R)-{3-[4-(4-oxo-piperidin-1-yl)-phenyl]-2-oxo-oxazolidin-5-ylmethyl}-methanesulphonate was treated with diethylcyanomethyl phosphonate as per Example 1 to provide titled compound in 42% yield.

M.P. 120-122° C. and MS (M+1)=392 (MH$^+$, 100%), M.F.=$C_{18}H_{21}N_3O_5S$.

Example 7

Preparation (S)-N-{3-[4-(4-cyanomethylidene-piperidin1-yl)-3-fluorophenyl]-2-oxo-oxazolidin-5-ylmethyl}-isocyanate

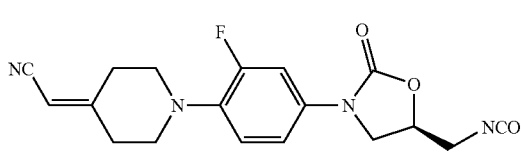

Step-1

The (S)-{3-[4-(4-oxo-piperidin-1-yl)-3-fluorophenyl]-2-oxo-oxazolidin-5-ylmethyl}-amine was was treated with diethylphosphonate as per Example-1 to provide (S)-N-{3-[4-(4-cyanomethylidene-piperidin-1-yl)-3-fluorophenyl]-2-oxo-oxazolidin-5-ylmethyl}-amine in 88% yield.

Step-2

Triphosgene (0.580, 1.81 mmol) was added to a solution of compound of step-1 (0.50 g, 1.5 mmol) in 25 ml dichloromethane followed by triethyl amine (3.5 ml) at 0-5° C. under nitrogen.

The reaction mixture was stirred at room temperature for 1 hour. The solvent was evaporated and the residue obtained was chromatographed on the silica gel to afford the titled compound.

M.P. 172-174° C. and MS (M+1)=357 (MH$^+$, 100%), M.F.=$C_{18}H_{17}FN_4O_3$.

Example 8

Preparation of (S)-N-{3-[4-(4-cyanomethylidene-piperidin-1-yl)-3-fluorophenyl]-2-oxo-oxazolidin-5-ylmethyl}-formamide

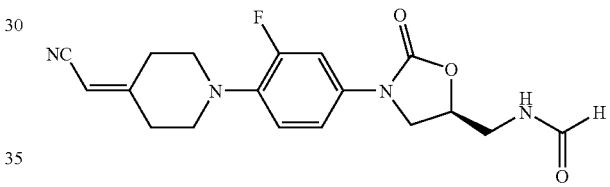

The (S)-N-{3-[4-(4-cyanomethylidene-piperidin-1-yl)-3-fluorophenyl]-2-oxo-oxazolidin-5-ylmethyl}-amine of Example-7, step-1 was subjected to the procedure described in Example-2 step-2, the title compound was isolated in 48% yield.

M.P. 183-184° C. and MS (M+1)=359 (MH$^+$, 100%), M.F.=$C_{18}H_{19}FN_4O_3$.

Example 9

Preparation of (S)-N-{3-[4-(4-cyanomethylidene-piperidin-1-yl)-3-fluorophenyl]-2-oxo-oxazolidin-5-ylmethyl}-acetamide

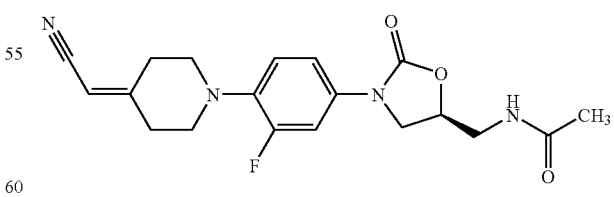

The intermediate i was treated with diethylcyanomethyl phosphonate as per Example 1 to provide titled compound in 91% yield.

Mp. 159-160° C.

$^1$H-NMR (CDCl$_3$, 200 MHz): δ 2.02 (3H, s), 2.50-2.61 (2H, m), 2.71-2.82 (2H, m), 3.05-3.29 (4H, m), 3.52-3.81

(3H, m), 3.95-4.11 (1H, m), 4.69-4.85 (1H, m), (5.21 (1H, s), 6.19 (1H, t, J=5.9 mHz), 6.95 (1H, dd, J=9.2, 9.2 Hz), 7.10 (1H, dd, J=2.2, 2.2 Hz), 7.45 (1H, dd, J=2.2, 14.0 Hz).

ESMS m/z 373 (MH+, 100%).

Example 10

Preparation of (S)-N-{3-[4-(4-cyanomethylidene-piperidin-1-yl)-3-fluorophenyl]-2-oxo-oxazolidin-5-ylmethyl}-propionamide

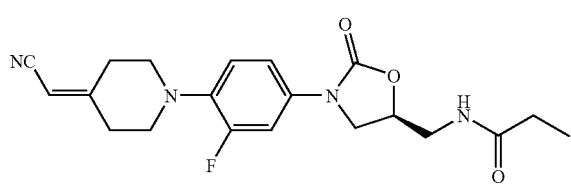

The mixture of (S)-N-{3-[4-(4-cyanomethylidene-piperidin-1-yl)-3-fluorophenyl]-2-oxo-oxazolidin-5-ylmethyl}-amine (1.5 mmol), propionyl chloride (1.79 mmol) in 10 ml pyridine was stirred at room temperature for 3 hours. Evaporation of the solvent under vacuum and silica gel column chromatography afforded the titled compound in 52% yield.

Mp. 200-202° C.

$^1$H-NMR (CDCl$_3$, 200 MHz): δ 1.10 (3H, t, J=7.2 Hz), 2.23 (2H, q, J=4.8 Hz), 2.50-2.60 (2H, m), 2.70-2.85 (2H, m), 310-3.21 (4H, m), 3.59-3.82 (3H, m), 3.95-4.10 (1H, m), 4.70-4.85 (1H, m), 5.20 (1H, s), 6.09 (1H, t, J=5.9 Hz), 6.90 (1H, dd, J=9.2, 9.2 Hz), 7.10 (1H, dd, J=2.2, 2.2 Hz), 7.44 (1H, dd, J=2.2, 14.0 Hz).

ESMS m/z 387 (MH+, 100%).

Example 11

Preparation of (S)-N-{3-[4-(4-cyanomethylidene-piperidin-1-yl)-3-fluorophenyl]-2-oxo-oxazolidin-5-ylmethyl}-2-dimethylpropionamide

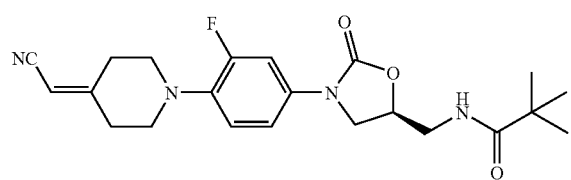

Following the procedure described in Example 10 and using pivaloyl chloride in the place of propionyl chloride the title compound was isolated in 65% yield.

Mp. 198-200° C.

$^1$H-NMR (CDCl$_3$, 200 MHz): δ 1.18 (9H, s), 2.45-2.61 (2H, m), 2.70-2.85 (2H, m), 3.10-3.25 (4H, m), 3.60-3.85 (3H, m), 3.90-4.10 (1H, m), 4.70-4.85 (1H, m), 5.20 (1H, s), 6.10 (1H, t, J=5.9 Hz), 6.90 (1H, dd, J=9.2, 9.2 Hz), 7.05 (1H, dd, J=2.2, 2.2 Hz), 7.45 (1H, dd, J=2.2, 14.0 Hz).

ESMS m/z 415 (MH+, 100%).

Example 12

Preparation of (S)-N-{3-[4-(4-cyanomethylidene-piperidin-1-yl)-3-fluorophenyl]-2-oxo-oxazolidin-5-ylmethyl}-3,3-dimethylbutanamide

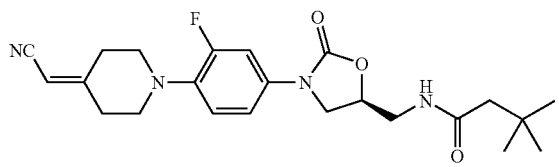

Following the procedure described in Example 10 and using 3,3-dimethyl butyryl chloride in the place of propionyl chloride the title compound was isolated in 54% yield.

M.P. 210-212° C. and MS (M+1)=431 (MH+, 100%), M.F.=C$_{22}$H$_{27}$FN$_4$O$_4$.

Example 13

Preparation of (S)-N-{3-[4-(4-cyanomethylidene-piperidin-1-yl)-3-fluorophenyl]-2-oxo-oxazolidin-5-ylmethyl}-2-hydroxyacetamide

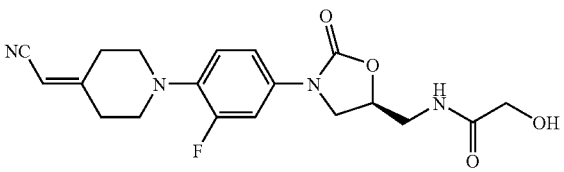

The mixture of (S)-N-{3-[4-(4-cyanomethylidene-piperidin-1-yl)-3-fluorophenyl]-2-oxo-oxazolidin-5-ylmethyl}-amine (2.87 mmol), glycolic acid (5.74 mmol), dicyclohexylcarbodiimide (7.17 mmol), 4-dimethylaminopyridine (100 mg) in dichloromethane (50 ml) was stirred for 3 hours. The reaction mixture was filtered. The filtrate was evaporated and the residue was purified by column chromatography over a silica gel to give title compound in 70% yield.

M.P. 68-70° C. and MS (M+1)=389 (MH+, 100%), M.F.=C$_{19}$H$_{21}$FN$_4$O$_4$.

Example 14

Preparation of (S)-N-{3-[4-(4-cyanomethylidene-piperidin-1-yl)-3-fluorophenyl]-2-oxo-oxazolidin-5-ylmethyl}-2-pivolyloxyacetamide

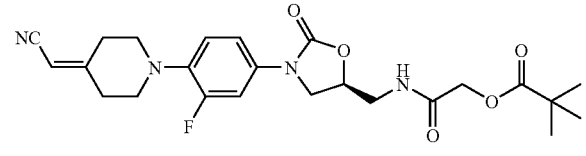

Following the procedure described in Example 10 and using t-butylcarbonyloxy-methyl chloroformate in the place of propionyl chloride the title compound was isolated in 54% yield.

M.P. 91-93° C. and MS (M+1)=473 (MH+, 100%), M.F.=C$_{24}$H$_{29}$FN$_4$O$_5$.

Example 15

Preparation of (S)-N-{3-[4-(4-cyanomethylidene-piperidin-1-yl)-3-fluorophenyl]-2-oxo-oxazolidin-5-ylmethyl}-N-methylacetamide

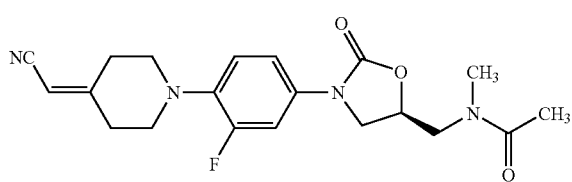

The compound obtained in Example 9 (1 mmol) was treated with n-butyl lithium (1.6 M in hexane, 1.6 mmol), methyl iodide (2 mmol) in 10 ml tetrahydrofuran at −78° C. temperature. The reaction mixture was with ethyl acetate water mixture. The organic layer was evaporated to give a crude compound, which was chromatographed on a silica gel to give the titled compound in 44% yield.

Mp. 128-132° C.

$^1$H-NMR (CDCl$_3$, 200 MHz): δ 2.15 (3H, s), 2.45-2.65 (2H, m), 2.70-2.90 (2H, m), 3.10-3.30 (7H, m), 3.41-3.60 (1H, m), 3.61-3.80 (1H, m), 3.82-4.10 (2H, m), 4.80-5.00 (1H, m), 5.20 (1H, s), 6.90-7.19 (2H, m), 7.40-7.60 (1H, m).

ESMS m/z 387 (MH$^+$, 100%).

Example 16

Preparation of (S)-{3-[4-(4-cyanomethylidene-piperidin-1-yl)-3-fluorophenyl]-2-oxo-oxazolidin-5-ylmethyl}-azide

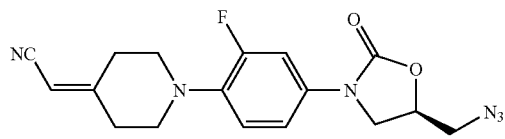

The (S)-{3-[4-(4-oxo-piperidin-1-yl)-3-fluorophenyl]-2-oxo-oxazolidin-5-ylmethyl}-azide was converted to the title compound by using the procedure described in Example-1 in 40% yield.

M.P. 112-114° C. and MS (M+1)=357 (MH$^+$, 100%), M.F.=C$_{17}$H$_{17}$FN$_4$O$_2$.

Example 17

Preparation of (S)-{3-[4-(4-cyanomethylidene-piperidin-1-yl)-3-fluorophenyl]-2-oxo-oxazolidin-5-ylmethyl}-amine

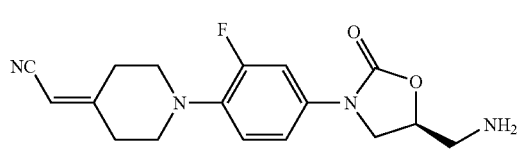

The procedure to prepare title compound is described in Example 7.

P. 162-164° C. and MS (M+1)=331 (MH$^+$, 100%), M.F.=C$_{17}$H$_{19}$FN$_4$O$_2$.

Example 18

Preparation of (S)-{3-[4-(4-cyanomethylidene-piperidin-1-yl)-3-fluorophenyl]-2-oxo-oxazolidin-5-ylmethylamino}-prop-2-ene

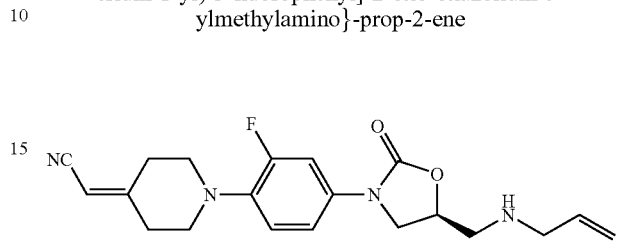

The mixture of (S)-N-{3-[4-(4-cyanomethylidene-piperidin-1-yl)-3-fluorophenyl]-2-oxo-oxazolidin-5-ylmethyl}-amine (0.12 mmol), allyl bromide (0.18 mmol), and potassium carbonate (0.25 mmol) in tetrahydrofuran was heated at reflux temperature for 12 hours. Solvent evaporation and purification to provided the title compound in 35% yield.

P. 102-104° C. and MS (M+1)=371 (MH$^+$, 100%), M.F.=C$_{20}$H$_{23}$FN$_4$O$_2$.

Example 19

Preparation of (S)-{3-[4-(4-cyanomethylidene-piperidin-1-yl)-3-fluorophenyl]-2-oxo-oxazolidin-5-ylmethylamino}-nitrile

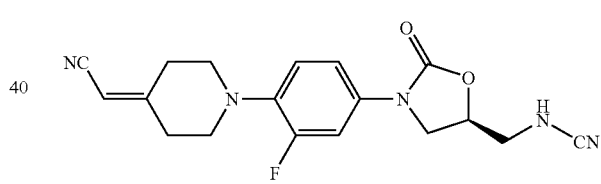

Following the procedure described in Example 10 and using cyanogen bromide in the place of propionyl chloride the title compound was isolated in 66% yield.

P. 121-122° C. and MS (M+1)=356 (MH$^+$, 100%), M.F.=C$_{18}$H$_{18}$FN$_5$O$_2$.

Example 20

(S)-{3-[4-(4-Cyanomethylidene-piperidin-1-yl)-3-fluorophenyl]-2-oxo-oxazolidin-5-ylmethylamino}-acetonitrile

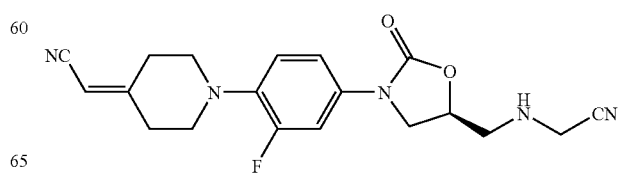

Following the procedure described in Example 10 and using bromoacetotrile in the place of propionyl chloride the title compound was isolated in 55% yield.

P. 129-131° C. and MS (M+1)=370 (MH+, 100%), M.F.=$C_{19}H_{20}FN_5O_2$.

Example 21

(S)-{3-[4-(4-cyanomethylidene-piperidin-1-yl)-3-fluorophenyl]-2-oxo-oxazolidin-5-ylmethylamino}-methylamine

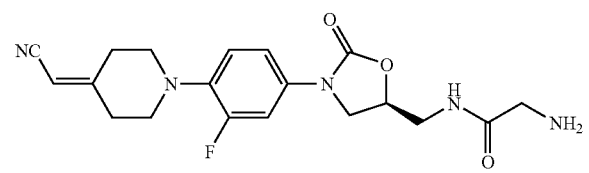

The mixture of triethylamine (2.65 mmol), Fmoc L-glycine (2.54 mmol), isobutylchloroformate (2.54 mmol), (S)-N-{3-[4-(4-cyanomethylidene-piperidin-1-yl)-3-fluorophenyl]-2-oxo-oxazolidin-5-ylmethyl}-amine (2.12 mmol) in dichloromethane (10 ml) was stirred for 3-5 h at room temperature. The reaction mixture was extracted with dichloromethane and water mixture. The combined organic layer was dried and evaporation of the solvent afforded a crude compound. It was further purified by column chromatography over a silica gel to give a solid.

The solid was stirred with 40% piperidine in tetrahydrofurane for 2-3 hours. The solvent was removed under reduced pressure and the residue was crystallized to give the title compound in 70% yield.

P. 171-172° C. and MS (M+1)=388 (MH+, 100%), M.F.=$C_{19}H_{22}FN_5O_3$.

Example 22

(S)-{N-{3-[4-(4-cyanomethylidene-piperidin-1-yl)-3-fluorophenyl]-2-oxo-oxazolidin-5-ylmethylamino}N-cyano}-prop-2-ene

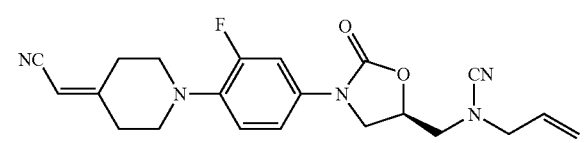

The compound of Example 18 was treated with cyanogen bromide as per procedure in Example 10 to give titled compound in 32% yield.

M.P. 111-113° C. and MS (M+1)=396 (MH+, 100%), M.F.=$C_{21}H_{22}FN_5O_2$.

Example 23

(S)-N-{3-[4-(4-cyanomethylidene-piperidin-1-yl)-3-fluorophenyl]-2-oxo-oxazolidin-5-ylmethyl}-2-cyanoacetamide

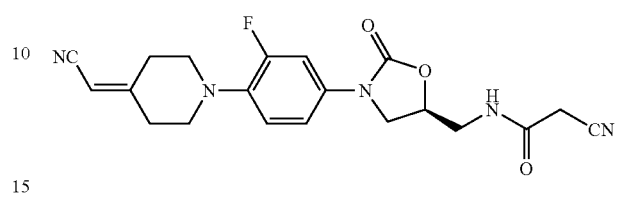

By following the procedure as per Example 13, and by using 2-cyanoacetic acid in the place of glycolic acid, the title compound was isolated in 42% yield.

M.P. 150-152° C. and MS (M+1)=398 (MH+, 100%), M.F.=$C_{20}H_{20}FN_5O_3$.

Example 24

(S)-N-{3-[4-(4-cyanomethylidene-piperidin-1-yl)-3-fluorophenyl]-2-oxo-oxazolidin-5-ylmethyl}-2-oxo-oxazolidin-4-yl-carboxamide

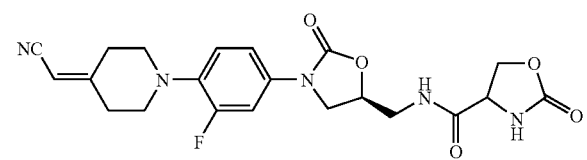

Step-1

By following the procedure as per Example 21, and by using L-serine in the place of L-glycine the 2-amino-3-hydroxypropionamide compound was isolated in 42% yield.

Step-2

The solution of above compound (0.25 mmol), carbonyldiimidazole (0.095 g, 0.58 mmol) in dry tetrahydrofuran (10 ml) was stirred for 18 hours. Evaporation of the solvent gave crude solid, which was purified by column chromatography over a silica gel to give the title compound in 84% yield.

M.P. 145° C. and MS (M+1)=444 (MH+, 100%), M.F.=$C_{21}H_{22}FN_5O_5$.

Example 25

(S)-N-{3-[4-(4-cyanomethylidene-piperidin-1-yl)-3-fluorophenyl]-2-oxo-oxazolidin-5-ylmethyl}-pyrrolidin-2-carboxamide

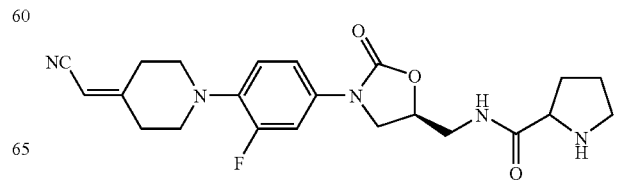

By following the procedure of Example 21, and by using L-proline in the place of L-glycine the title compound was isolated in 42% yield.

M.P. 155° C. and MS (M+1)=428 (MH⁺, 100%), M.F.=$C_{22}H_{26}FN_5O_3$.

Example 26

(S)-1-{3-[4-(4-cyanomethylidene-piperidin-1-yl)-3-fluorophenyl]-2-oxo-oxazolidin-5-ylmethyl}-4-carboethoxy-1,2,3-triazole

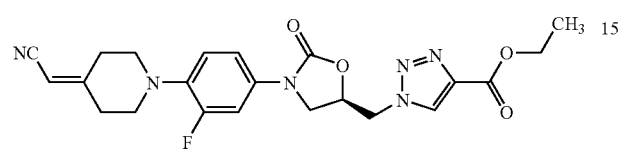

The title compound was prepared by using compound of Example 16 and following the procedure of Example-4 in 64% yield.

M.P. 164-166° C. and MS (M+1)=455 (MH⁺, 100%), M.F.=$C_{22}H_{23}FN_6O_4$.

Example 27

(S)-1-{3-[4-(4-cyanomethylidene-piperidin-1-yl)-3-fluorophenyl]-2-oxo-oxazolidin-5-ylmethyl}-5-carboethoxy-1,2,3-triazole

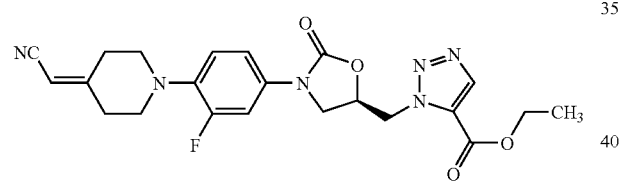

The title compound was prepared by using the compound of Example 16 and following the procedure of Example-4 in 26% yield.

M.P. 70-72° C. and MS (M+1)=455 (MH⁺, 100%), M.F.=$C_{22}H_{23}FN_6O_4$.

Example 28

(S)-1-{3-[4-(4-cyanomethylidene-piperidin-1-yl)-3-fluorophenyl]-2-oxo-oxazolidin-5-ylmethyl}-4-cyano-1,2,3-triazole

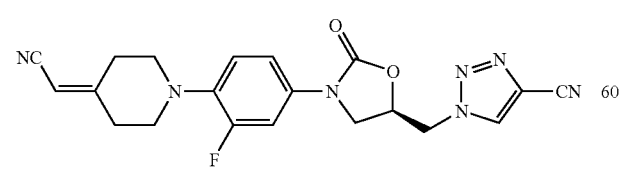

The title compound was prepared by using compound of Example 26 and following the procedure of Example-5 in 45% yield.

M.P. 78-80° C. and MS (M+1)=408 (MH⁺, 100%), M.F.=$C_{20}H_{18}FN_7O_2$.

Example 29

(S)-N-{3-[4-(4-cyanomethylidene-piperidin-1-yl)-3-fluorophenyl]-2-oxo-oxazolidin-5-ylmethyl}-difluoroacetamide

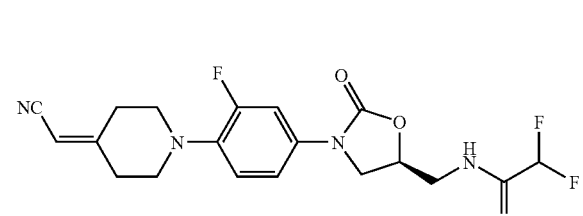

The mixture of (S)-N-{3-[4-(4-cyanomethylidene-piperidin-1-yl)-3-fluorophenyl]-2-oxo-oxazolidin-5-ylmethyl}-amine (0.5 g, 1.45 mmol), oxalyl chloride (0.150 ml, 1.74 mmol), difluoroacetic acid (0.1 ml, 1.74 mmol) and triethylamine (0.242 ml, 1.74 mmol) in dichloromethane (20 ml) was stirred for 1 hour at room temperature. The reaction mixture was extracted with the dichloromethane water mixture. The combined organic layer was dried and removal of the solvent afforded a residue which was chromatographed over silica gel to give title compound in 48% yield.

M.P. 162-164° C. and MS (M+1)=409 (MH⁺, 100%), M.F.=$C_{19}H_{19}F_3N_4O_3$.

Example 30

(S)-N-{3-[4-(4-cyanomethylidene-piperidin-1-yl)-3-fluorophenyl]-2-oxo-oxazolidin-5-ylmethyl}-trifluoroacetamide;

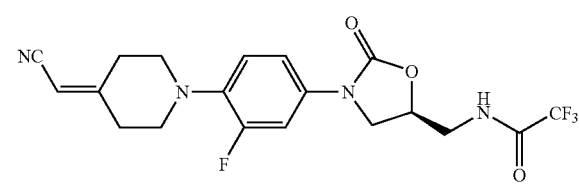

The title compound was prepared by following the procedure of Example 29 and by using trifluoroacetic acid in the place of difluoroacetic acid in 45% yield.

Mp. 181-183° C.

¹H-NMR (CDCl₃, 200 MHz): δ 2.50-2.60 (2H, m), 2.70-2.85 (2H, m), 310-3.21 (4H, m), 3.59-3.80 (2H, m) 3.82-4.00 (1H, m), 4.10-4.20 (1H, m), 4.75-4.95 (1H, m), 5.20 (1H, s), 6.92 (1H, dd, J=9.2, 9.2 Hz), 7.05 (1H, dd, J=2.2, 2.2 Hz), 7.20-7.30 (1H, m), 7.42 (1H, dd, J=2.2, 14.0 Hz).

ESMS m/z 427 (MH⁺, 100%).

Example 31

(S)-N-{3-[4-(4-cyanomethylidene-piperidin-1-yl)-3-fluorophenyl]-2-oxo-oxazolidin-5-ylmethyl}-chloroacetamide

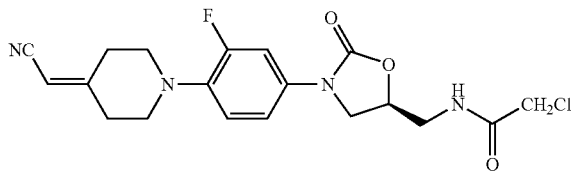

The title compound was prepared by following the procedure of Example 29 and by using chloroacetic acid in the place of difluoroacetic acid in 77% yield.

MS (M+1)=407 (MH+, 100%), M.F.=$C_{19}H_{20}FN_4O_3Cl$.

Example 32

(S)-N-{3-[4-(4-cyanomethylidene-piperidin-1-yl)-3-fluorophenyl]-2-oxo-oxazolidin-5-ylmethyl}-dichloroacetamide

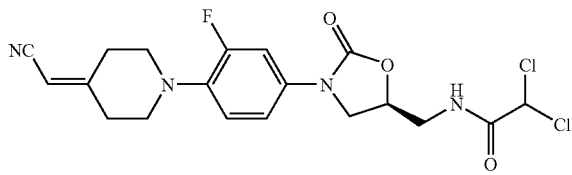

The title compound was prepared by following the procedure of Example 29 and by using dichloroacetic acid in the place of difluoroacetic acid in 39% yield.

M.P. 159-161° C. and MS (M+1)=442 (MH+, 100%), M.F.=$C_{19}H_{19}FN_4O_3Cl_2$.

Example 33

(S)-N-{3-[4-(4-cyanomethylidene-piperidin-1-yl)-3-fluorophenyl]-2-oxo-oxazolidin-5-ylmethyl}-trichloroacetamide

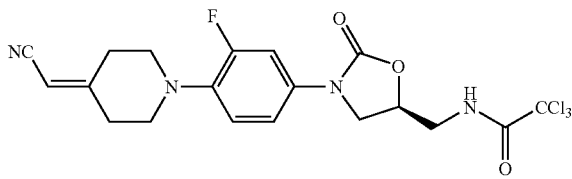

The title compound was prepared by following the procedure of Example 29 and by using trichloroacetic acid in the place of difluoroacetic acid in 42% yield.

M.P. 142-144° C. and MS (M+1)=476 (MH+, 100%), M.F.=$C_{19}H_{18}FN_4O_3Cl_3$.

Example 34

(S)-N-{3-[4-(4-cyanomethylidene-piperidin-1-yl)-3-fluorophenyl]-2-oxo-oxazolidin-5-ylmethyl}-bromoacetamide

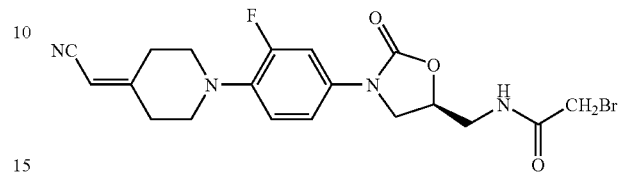

The title compound was prepared by following the procedure of Example 10 and by using bromoacetylbromide in the place of propionyl chloride in 77% yield.

M.P. 160-162° C. and MS (M+1)=452 (MH+, 100%), M.F.=$C_{19}H_{20}FN_4O_3Br$.

Example 35

(S)-N-{3-[4-(4-cyanomethylidene-piperidin-1-yl)-3-fluorophenyl]-2-oxo-oxazolidin-5-ylmethyl}-dibromoacetamide

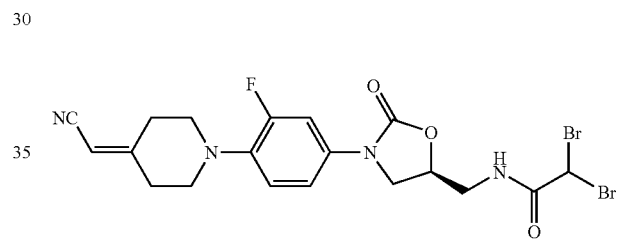

The title compound was prepared by following the procedure of Example 29 and by using dibromoacetic acid in the place of difluoroacetic acid in 57% yield.

MS (M+1)=531 (MH+, 100%), M.F.=$C_{19}H_{19}FN_4O_3Br_2$.

Example 36

(S)-N-{3-[4-(4-cyanomethylidene-piperidin-1-yl)-3-fluorophenyl]-2-oxo-oxazolidin-5-ylmethyl}-iodoacetamide

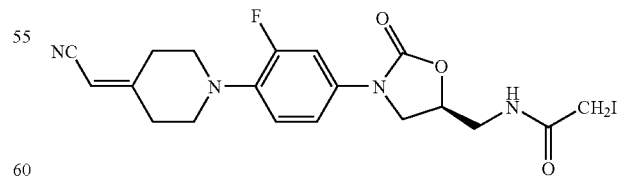

The title compound was prepared by following the procedure of Example 10 and by using iodoacetyliodide in the place of propionyl chloride in 29% yield.

M.P. 178-180° C. and MS (M+1)=499 (M+, 100%), M.F.=$C_{19}H_{20}FN_4O_3I$.

Example 37

(S)-N-{3-[4-(4-cyanomethylidene-piperidin-1-yl)-3-fluorophenyl]-2-oxo-oxazolidin-5-ylmethyl}-4-methylphenylsulphonamide

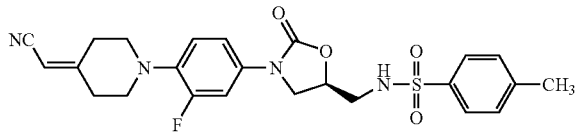

The title compound was prepared by following the procedure of Example 10 and by using p-toluene sulfonylchloride in the place of propionyl chloride in 69% yield.

Mp. 180-182° C.

$^1$H-NMR (CDCl$_3$, 200 MHz): δ 2.45 (3H, s), 2.50-2.60 (2H, m), 2.70-2.85 (2H, m), 3.09-3.40 (64, m), 3.85-4.10 (2H, m), 4.65-4.80 (1H, m), 5.20 (1H, s), 6.90 (1H, dd, J=9.2, 9.2 Hz), 7.05 (1H, dd, J=2.2, 2.2 Hz), 7.25-7.39 (4H, m), 7.40 (1H, d, J=2.2, 9.2Hz).

ESMS m/z 485 (MH$^+$, 100%).

Example 38

(S)-N-{3-[4-(4-cyanomethylidene-piperidin-1-yl)-3-fluorophenyl]-2-oxo-oxazolidin-5-ylmethyl}-methylcarbamate

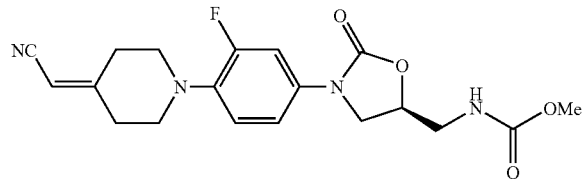

The mixture of (S)-N-{3-[4-(4-cyanomethylidene-piperidin-1-yl)-3-fluorophenyl]-2-oxo-oxazolidin-5-ylmethyl}-isocyanate (1.0 mmol), sodium methoxide (1.2 mmol) in methanol (10 ml) was stirred for 2 hours at room temperature. The reaction mixture was extracted with the ethyl acetate water mixture. The organic extract was dried and removal of solvent afforded title compound in 75% yield.

MS (M+1)=389 (MH$^{30}$, 100%), M.F.=C$_{19}$H$_{21}$FN$_4$O$_4$.

Example 39

(S)-N-{3-[4-(4-cyanomethylidene-piperidin-1-yl)-3-fluorophenyl]-2-oxo-oxazolidin-5-ylmethyl}-ethylcarbamate

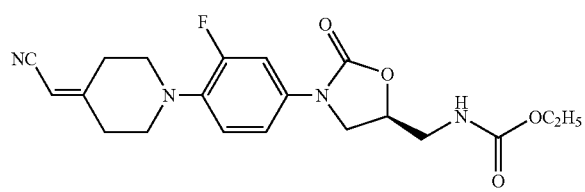

The title compound was prepared by following the procedure of Example 38 and by using sodium ethoxide in the place of sodium methoxide in 54% yield.

MS (M+1)=403 (MH$^+$, 100%), M.F.=C$_{20}$H$_{23}$FN$_4$O$_4$.

Example 40

(S)-N-{3-[4-(4-cyanomethylidene-piperidin-1-yl)-3-fluorophenyl]-2-oxo-oxazolidin-5-ylmethyl}-isopropylcarbamate

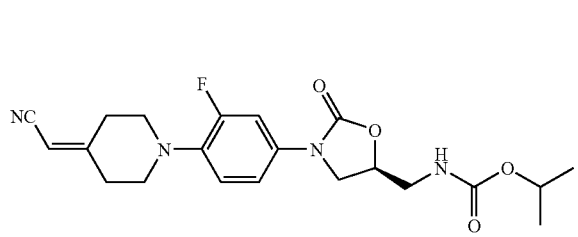

The title compound was prepared by following the procedure of Example 10 and by using isopropylchloroformate in the place of propionyl chloride in 48% yield.

202-204° C. and MS (M+1)=431 (MH$^+$, 100%), M.F.=C$_{22}$H$_{27}$FN$_4$O$_4$.

Example 41

(2S, 5S)-{N-{3-[4-(4-cyanomethylidene-piperidin-1-yl)-3-fluorophenyl]-2-oxo-oxazolidin-5-ylmethyl}-propionamid-2-yl}-amine

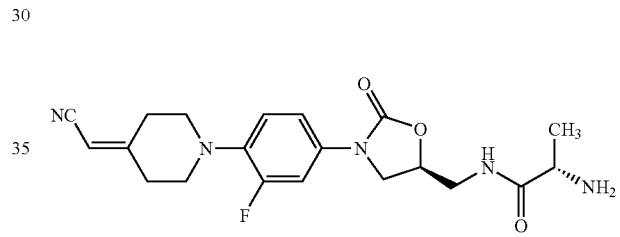

The title compound was prepared by following the procedure of Example 21 and by using L-alanine in the place of L-glycine in 67% yield.

M.P. 103-105° C. and MS (M+1)=402 (MH$^+$, 100%), M.F.=C$_{20}$H$_{24}$FN$_5$O$_3$.

Example 42

(2S, 5S)-{N-{3-[4-(4-cyanomethylidene-piperidin-1-yl)-3-fluorophenyl]-2-oxo-oxazolidin-5-ylmethyl}-3-hydroxypropionamid-2-yl}-amine

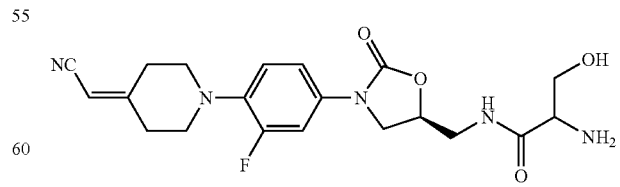

The procedure to prepare the title compound is described in Example 24.

M.P. 88-90° C. and MS (M+1)=418 (MH$^+$, 100%), M.F.=C$_{20}$H$_{24}$FN$_5$O$_4$.

Example 43

(2S, 5S){N-{3-[4-(4-cyanomethylidene-piperidin-1-yl)-3-fluorophenyl]-2-oxo-oxazolidin-5-ylmethyl}-3-(imidazol-4-yl)-propionamid-2-yl}-amine

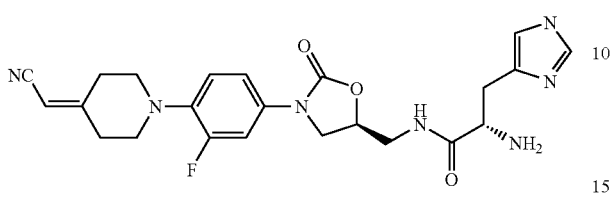

The title compound was prepared by following the procedure of Example 21 and by using L-histidine in the place of L-glycine in 63% yield.

M.P. 93-96° C. and MS (M+1)=468 (MH$^+$, 100%), M.F.=C$_{23}$H$_{26}$FN$_7$O$_3$.

Example 44

(S)-N-{3-[4-(4-cyanomethylidene-piperidin-1-yl)-3-fluorophenyl]-2-oxo-oxazolidin-5-ylmethyl}-1-pthalamide

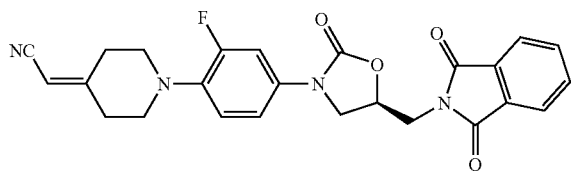

The title compound was prepared by following the procedure of Example 1 and by using (S)-{3-[4-(4-oxo-piperidin-1-yl)-3-fluorophenyl]-2-oxo-oxazolidin-5-ylmethyl}-pthalamide in 67% yield.

M.P. 183-185° C. and MS (M+1)=461 (MH$^+$, 100%), M.F.=C$_{25}$H$_{21}$FN$_4$O$_4$.

Example 45

(S)-N-{3-[4-(4-cyanomethylidene-piperidin-1-yl)-3-fluorophenyl]-2-oxo-oxazolidin-5-ylmethyl}-thioacetamide

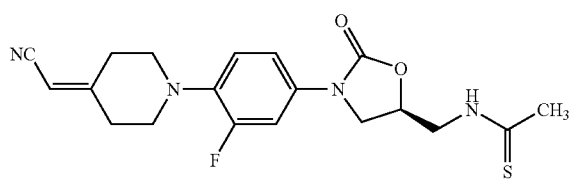

A mixture of the compound of Example-9 (0.26 mmol), Lawesson's reagent (0.40 mmol) in dioxane (10 ml) was stirred at 100° C. for one hour. The reaction mixture was concentrated in vacuo to give a residue. The residue was purified by silica gel column chromatography to afford title compound in 82% yield.

Mp. 190-192° C.

$^1$H-NMR (CDCl$_3$, 200 MHz): δ 2.50-2.70 (5H, m), 2.76-2.90 (2H, m), 3.10-3.30 (4H, m), 3.75-3.90 (1H, m), 4.00-4.20 (2H, m), 4.25-4.40 (1H, m), 4.90-5.10 (1H, m), 5.21 (1H, s), 6.90-7.10 (2H, m), 7.45 (1H, dd, J=2.2, 14.0 Hz)., 8.10-8.30 (1H, s).

ESMS m/z 389 (MH$^+$, 100%).

Example 46

(S)-N-{3-[4-(4-cyanomethylidene-piperidin-1-yl)-3-fluorophenyl]-2-oxo-oxazolidin-5-ylmethyl}-methylthiocarbamate

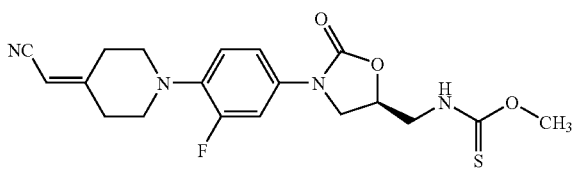

Step 1

The mixture of (S)-N-{3-[4-(4-cyanomethylidene-piperidin-1-yl)-3-fluorophenyl]-2-oxo-oxazolidin-5-ylmethyl}-amine (10 mmol), triethylamine (10 mmol) and carbon disulphide (20 mmol) in tetrahydrofuran (50 ml) was stirred for 4 hours at 0° C.

To the solution ethyl chloroformate (5.8 mmol) was added and stirred for 1 hour. The reaction mixture washed with water followed by brine and dried over sodium sulfate. The evaporation of solvent gave (S)-N-{3-[4-(4-cyanomethylidene-piperidin-1-yl)-3-fluorophenyl]-2-oxo-oxazolidin-5-ylmethyl}-thioisocyanate in 69% yield.

Step-2

Thioisocyanate compound was treated with sodium methoxide as per procedure described in Example-38 to afford the title compound in 77% yield.

M.P. 147-148° C. and MS (M+1)=405 (MH$^+$, 100%), M.F.=C$_{19}$H$_{21}$FN$_4$O$_3$S.

Example 47

(S)-N-{3-[4-(4-cyanomethylidene-piperidin-1-yl)-3-fluorophenyl]-2-oxo-oxazolidin-5-ylmethyl}-2-hydroxythioacetamide

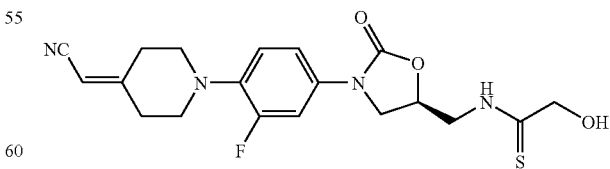

The title compound was prepared by following the procedure of Example 45 and by using compound of Example-13 in 42% yield.

M.P. 102-105° C. and MS (M+1)=405 (MH$^+$, 100%), M.F.=C$_{19}$H$_{21}$FN$_4$O$_3$S.

Example 48

(S)-N-{3-[4-(4-cyanomethylidene-piperidin-1-yl)-3-fluorophenyl]-2-oxo-oxazolidin-5-ylmethyl}-2-hydroxyethylthiocarbamide

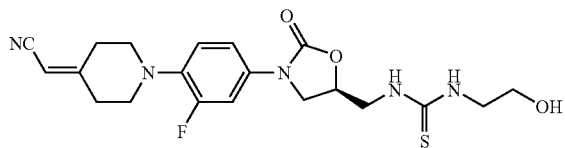

The title compound was prepared by following the procedure of Example 46, step-2 by using aminoethanol in place of sodium methoxide in 36% yield.

M.P. 168-170° C. and MS (M+1)=434 (MH$^+$, 100%), M.F.=$C_{20}H_{24}FN_5O_3S$.

Example 49

(S)-N-{3-[4-(4-cyanomethylidene-piperidin-1-yl)-3-fluorophenyl]-2-oxo-oxazolidin-5-ylmethylamino}-thiocarbonylmethylamine

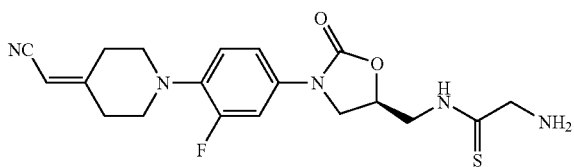

The title compound was prepared by following the procedure of Example-45 and by using S)-N-{3-[4-(4-cyanomethylidene-piperidin-1-yl)-3-fluorophenyl]-2-oxo-oxazolidin-5-ylmethylamino}-carbonylmethylamine in 38% yield.

M.P. 157-158° C. and MS (M+1)=404 (MH$^+$, 100%), M.F.=$C_{19}H_{22}FN_5O_2S$.

Example 50

(S)-N-{3-[4-(4-cyanomethylidene-piperidin-1-yl)-3-fluorophenyl]-2-oxo-oxazolidin-5-ylmethyl}-2-dimethylaminoethylthiocarbamide

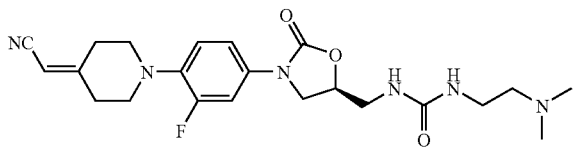

The title compound was prepared by following the procedure of Example 46, step-2 by using dimethylaminoethylamine in place of sodium methoxide in 40% yield.

M.P. 153-155° C. and MS (M+1)=461 (MH$^+$, 100%), M.F.=$C_{22}H_{29}FN_6O_3$.

Example 51

(S)-N-{3-[4-(4-cyanomethylidene-piperidin-1-yl)-3-fluorophenyl]-2-oxo-oxazolidin-5-ylmethyl}-thiocarbamide

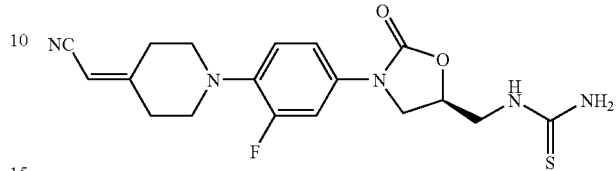

The title compound was prepared by following the procedure of Example 46, step-2 by using sodamide in place of sodium methoxide in 80% yield.

M.P. 190-191° C. and MS (M+1)=390 (MH$^+$, 100%), M.F.=$C_{18}H_{20}FN_5O_2S$.

Example 52

(S)-N-{3-[4-(4-cyanomethylidene-piperidin-1-yl)-3-fluorophenyl]-2-oxo-oxazolidin-5-ylmethyl}-methylthiocarbamide

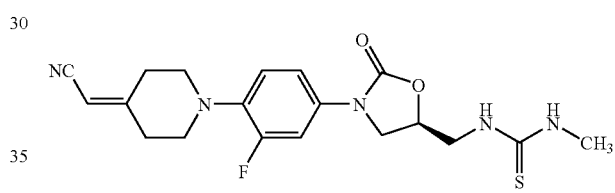

The title compound was prepared by following the procedure of Example 46, step-2 by using methylamine in place of sodium methoxide in 65% yield.

M.P. 191-192° C. and MS (M+1)=404 (MH$^+$, 100%), M.F.=$C_{19}H_{22}FN_5O_2S$.

Example 53

(S)-N-{3-[4-(4-cyanomethylidene-piperidin-1-yl)-3-fluorophenyl]-2-oxo-oxazolidin-5-ylmethyl}-methanesulphonamide

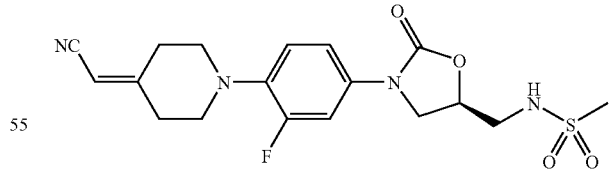

The title compound was prepared by following the procedure of Example 10 and by using methanesulfonylchloride in the place of propionyl chloride in 88% yield.

Mp. 235-237° C.

$^1$H-NMR (CDCl$_3$, 200 MHz): δ 2.45-2.60 (2H, m), 2.70-2.85 (2H, m), 3.09 (3H, s), 3.10-3.30 (4H, m), 3.35-3.65 (2H, m), 3.85-4.15 (2H, m), 4.70-5.00 (1H, m), 5.20 (1H, s), 6.90 (1H, dd, J=9.2, 9.2 Hz), 7.10 (1H, dd, J=2.2, 2.2 Hz), 7.42 (1H, dd, J=2.2, 14.0 Hz).

ESMS m/z 409 (MH$^+$, 100%).

Example 54

(R)-{3-[4-(4-cyanomethylidene-piperidin-1-yl)-3-fluorophenyl]-2-oxo-oxazolidin-5-ylmethyl}-methanesulphonate

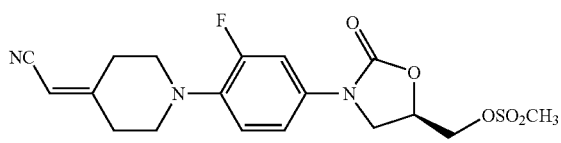

The title compound was prepared by following the procedure of Example-1 and by using (R)-{3-[4-(4-oxo-piperidin-1-yl)-3-fluorophenyl]-2-oxo-oxazolidin-5-ylmethyl}-methanesulphonate in 88% yield.

M.P. 126-128° C. and MS (M+1)=410 (MH$^+$, 100%), M.F.=$C_{18}H_{20}FN_3O_5S$.

Example 55

(S)-N-{3-[4-(4-cyanomethylidene-3-fluoropiperidin-1-yl)-phenyl]-2-oxo-oxazolidin-5-ylmethyl}-acetamide

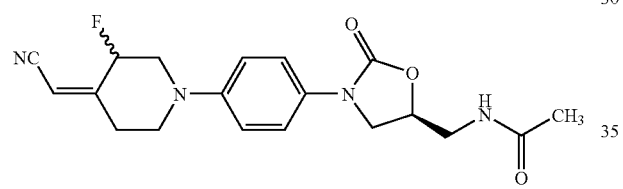

The title compound was prepared by following the procedure of Example 1 and by using (S)-{3-[4-(3-fluoro-4-oxo-piperidin-1-yl)-phenyl]-2-oxo-oxazolidin-5-ylmethyl}-acetamide in 76% yield.

MS (M+1)=373 (MH$^+$, 100%), M.F.=$C_{19}H_{21}FN_4O_3$.

Example 56

E/Z mixture/E and Z isomer of (S)-N-{3-[4-(4-cyanomethylidene-3-fluoropiperidin-1-yl)-3-fluorophenyl]-2-oxo-oxazolidin-5-ylmethyl}-acetamide

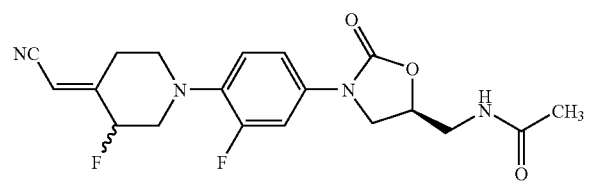

The title compound was prepared by following the procedure of Example 1 and by using S)-{3-[4-(3-fluoro-4-oxo-piperidin-1-yl)-3-fluorophenyl]-2-oxo-oxazolidin-5-ylmethyl}-acetamide in 71% yield as a mixture of isomers.

M.P. 100-102° C. and MS (M+1)=391 (MH$^+$, 100%), M.F.=$C_{19}H_{20}F_2N_4O_3$.

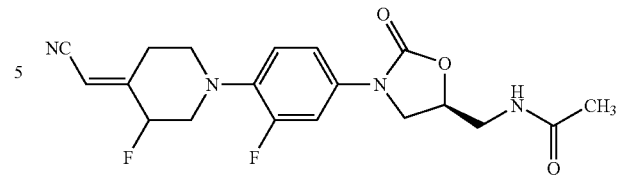

The mixture of compound was separated on preparative HPLC to provide E isomer in 56% yield as a white solid.

M.P. 138-140° C. and MS (M+1)=391 (MH$^+$, 100%), M.F.=$C_{19}H_{20}F_2N_4O_3$.

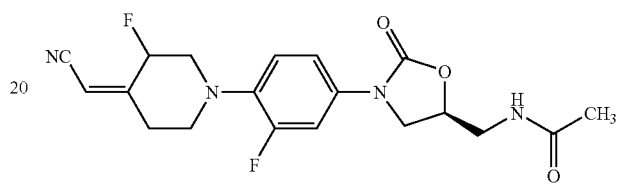

The mixture of compound was separated on preparative HPLC to provide Z isomer in 18% yield as a white solid.

M.P. 170-172° C. and MS (M+1)=391 (MH$^+$, 100%), M.F.=$C_{19}H_{20}F_2N_4O_3$.

Example 57

(S)-N-{3-[4-(4-cyanomethylidene-3-fluoropiperidin-1-yl)-3-fluorophenyl]-2-oxo-oxazolidin-5-ylmethyl}-difluoroacetamide

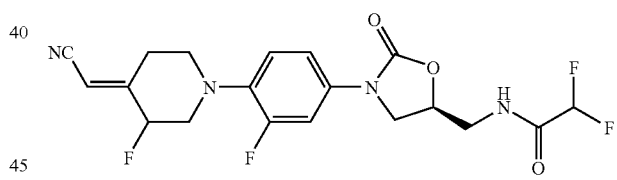

Step-1

Preparation of (S)-N-{3-[4-(4-cyanomethylidene-3-fluoropiperidin-1-yl)-3-fluorophenyl]-2-oxo-oxazolidin-5-ylmethyl}-amine.

The compound was prepared by following the procedure of Example-1 and by using (S)-{3-[4-(3,3-difluoro-4-oxo-piperidin-1-yl)-3-fluorophenyl]-2-oxo-oxazolidin-5-ylmethyl}-amine in 77% yield.

Step-2

The title compound was prepared by following the procedure of Example 29 and by using (S)-N-{3-[4-(4-cyanomethylidene-3-fluoropiperidin-1-yl)-3-fluorophenyl]-2-oxo-oxazolidin-5-ylmethyl}-amine in 80% yield.

M.P. 136-138° C. and MS (M+1)=427 (MH$^+$, 100%), M.F.=$C_{19}H_{18}F_4N_4O_3$.

Example 58

(S)-N-{3-[4-(4-cyanomethylidene-3-fluoropiperidin-1-yl)-3-fluorophenyl]-2-oxo-oxazolidin-5-ylmethyl}-isobutylcarbamate

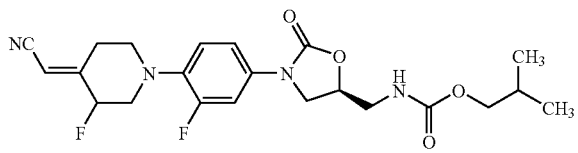

The title compound was prepared by following the procedure of Example 10 and by using (S)-N-{3-[4-(4-cyanomethylidene-3-fluoropiperidin-1-yl)-3-fluorophenyl]-2-oxo-oxazolidin-5-ylmethyl}-amine and isobutylchloroformate in 69% yield.

M.P. 162-164° C. and MS (M+1)=448 (MH$^+$, 100%), M.F.=$C_{22}H_{26}F_2N_4O_4$.

Example 59

(R)-{3-[4-(4-cyanomethylidene-3-fluoropiperidin-1-yl)-3-fluorophenyl]-2-oxo-oxazolidin-5-ylmethyl}-methanesulphonate

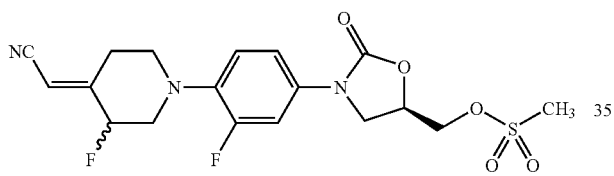

The title compound was prepared by following the procedure of Example 1 and by using (R)-{3-[4-(3-fluoro-4-oxo-piperidin-1-yl)-3-fluorophenyl]-2-oxo-oxazolidin-5-ylmethyl}-methanesulphonate in 59% yield.

M.P. 116-118° C. and MS (M+1)=428 (MH$^+$, 100%), M.F.=$C_{18}H_{19}F_2N_3O_5S$.

Example 60

(S)-N-{3-[4-(4-cyanomethylidene-3-fluoropiperidin-1-yl)-3-fluorophenyl]-2-oxo-oxazolidin-5-ylmethyl}-thioacetamide

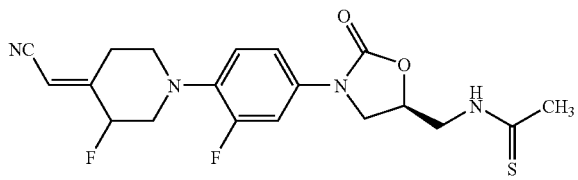

The title compound was prepared by following the procedure of Example 45 and by using (S)-N-{3-[4-(4-cyanomethylidene-3-fluoropiperidin-1-yl)-3-fluorophenyl]-2-oxo-oxazolidin-5-ylmethyl}-acetamide in 56% yield.

M.P. 137-138° C. and MS (M+1)=405 (MH$^+$, 100%), M.F.=$C_{19}H_{20}F_2N_4O_2S$.

Example 61

(S)-N-{3-[4-(4-cyanomethylidene-3,3-difluoropiperidin-1-yl)-phenyl]-2-oxo-oxazolidin-5-ylmethyl}-acetamide

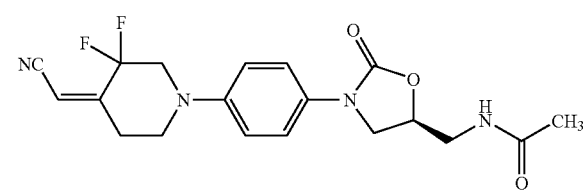

The title compound was prepared by following the procedure of Example 1 and by using (S)-{3-[4-(3,3-difluoro-4-oxo-piperidin-1-yl)-3-fluorophenyl]-2-oxo-oxazolidin-5-ylmethyl}-acetamide in 88% yield.

MS (M+1)=409 (MH$^+$, 100%), M.F.=$C_{19}H_{19}F_3N_4O_3$.

Example 62

(S)-N-{3-[4-(4-cyanomethylidene-3-methylpiperidin-1-yl)-3-fluorophenyl]-2-oxo-oxazolidin-5-ylmethyl}-formamide

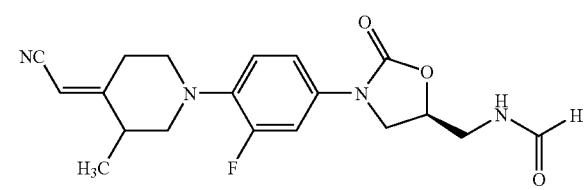

Step-1

Preparation of (S)-N-{3-[4-(4-cyanomethylidene-3-methylpiperidin-1-yl)-3-fluorophenyl]-2-oxo-oxazolidin-5-ylmethyl}-amine:

The compound was prepared by following the procedure of Example-1 and by using (S)-{3-[4-(3,3-difluoro-4-oxo-piperidin-1-yl)-3-fluorophenyl]-2-oxo-oxazolidin-5-ylmethyl}-amine in 80% yield.

Step-2

The title compound was prepared by following the procedure of Example-2 and by using (S)-N-{3-[4-(4-cyanomethylidene-3-methylpiperidin-1-yl)-3-fluorophenyl]-2-oxo-oxazolidin-5-ylmethyl}-amine in 59% yield.

M.P. 98-100° C. and MS (M+1)=373 (MH$^+$, 100%), M.F.=$C_{19}H_{21}FN_4O_3$.

Example 63

(S)-N-{3-[4-(4-cyanomethylidene-3-methylpiperidin-1-yl)-3-fluorophenyl]-2-oxo-oxazolidin-5-ylmethyl}-acetamide

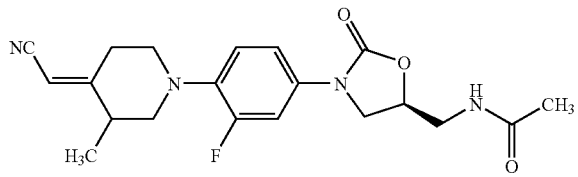

The title compound was prepared by following the procedure of Example-1 and by using (S)-{3-[4-(3,3-difluoro-4-oxo-piperidin-1-yl)-3-fluorophenyl]-2-oxo-oxazolidin-5-ylmethyl}-acetamide in 62% yield.

M.P. 152-153° C. and MS (M+1)=387 (MH$^+$, 100%), M.F.=C$_{20}$H$_{23}$FN$_4$O$_3$.

Example 64

(S)-N-{3-[4-(4-cyanomethylidene-3-methylpiperidin-1-yl)-3-fluorophenyl]-2-oxo-oxazolidin-5-ylmethyl}-trifluoroacetamide

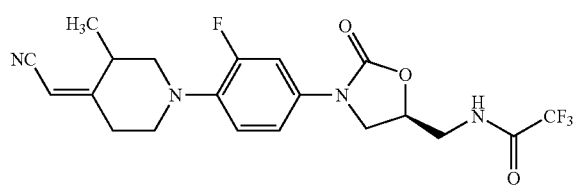

The title compound was prepared as per Example-29 by using (S)-N-{3-[4-(4-cyanomethylidene-3-methylpiperidin-1-yl)-3-fluorophenyl]-2-oxo-oxazolidin-5-ylmethyl}-amine and trifluoroacetic acid in 51% yield.

MS (M+1)=441 (MH$^+$, 100%), M.F.=C$_{20}$H$_{20}$F$_4$N$_4$O$_3$.

Example 65

(S)-N-{3-[4-(4-cyanomethylidene-3-methylpiperidin-1-yl)-3-fluorophenyl]-2-oxo-oxazolidin-5-ylmethyl}-2-cyanoacetamide

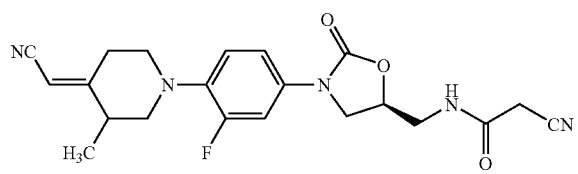

The title compound was prepared as per Example-29 by using (S)-N-{3-[4-(4-cyanomethylidene-3-methylpiperidin-1-yl)-3-fluorophenyl]-2-oxo-oxazolidin-5-ylmethyl}-amine and cyanoacetic acid in 81% yield.

M.P. 102-104° C. and MS (M+1)=412 (MH$^+$, 100%), M.F.=C$_{21}$H$_{22}$FN$_5$O$_3$.

Example 66

(S)-2-{3-[4-(4-cyanomethylidene-3-methylpiperidin-1-yl)-3-fluorophenyl]-2-oxo-oxazolidin-5-ylmethylamino}-1,3-thiazole

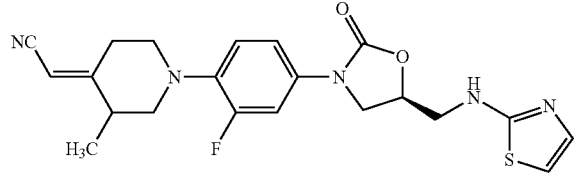

The mixture of (S)-N-{3-[4-(4-cyanomethylidene-3-methylpiperidin-1-yl)-3-fluorophenyl]-2-oxo-oxazolidin-5-ylmethyl}-thiocarbamide (0.5 mmol), acetaldehyde diethylacetal (0.6 mmol) and p-toluene-sulphonic acid (0.05 mmol) in acetic acid (5 ml) was heated at 70° C. for 1 hour. The reaction mixture extracted with ethyl acetate water mixture. The organic layer treated with sodium bicarbonate dried. The evaporation of the solvent silica gel column chromatographic purification afforded title compound in 60% yield.

M.P. 75-77° C. and MS (M+1)=428 (MH$^+$, 100%), M.F.=C$_{21}$H$_{22}$FN$_5$O$_2$S.

Example 67

(S)-N-{3-[4-(4-cyanomethylidene-3-methylpiperidin-1-yl)-3-fluorophenyl]-2-oxo-oxazolidin-5-ylmethyl}-methylthiocarbamate

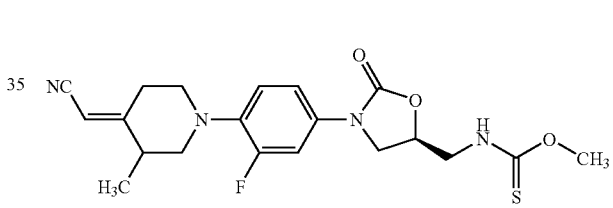

The title compound was prepared as per procedure described in Example-46 in by using (S)-N-{3-[4-(4-cyanomethylidene-3-methylpiperidin-1-yl)-3-fluorophenyl]-2-oxo-oxazolidin-5-ylmethyl}-methylthiocarbamate in 46% yield.

M.P. 78-80° C. and MS (M+1)=419 (MH$^+$, 100%), M.F.=C$_{20}$H$_{23}$FN$_4$O$_3$S.

Example 68

(S)-N-{3-[4-(4-cyanomethylidene-3-methylpiperidin-1-yl)-3-fluorophenyl]-2-oxo-oxazolidin-5-ylmethyl}-thiocarbamide

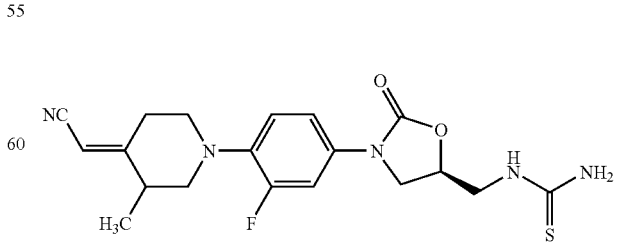

The title compound was prepared as per procedure described in Example-51 in by using (S)-N-{3-[4-(4-cyanomethylidene-3-methylpiperidin-1-yl)-3-fluorophenyl]-2-oxo-oxazolidin-5-ylmethyl}-thioisocyanate in 79% yield.

P. 142-144° C. and MS (M+1)=404 (MH+, 100%), M.F.=$C_{19}H_{22}FN_5O_2S$.

Example 69

(S)-N-{3-[4-(4-cyanomethylidene-3-methylpiperidin-1-yl)-3-fluorophenyl]-2-oxo-oxazolidin-5-ylmethyl}-methylthiocarbamide

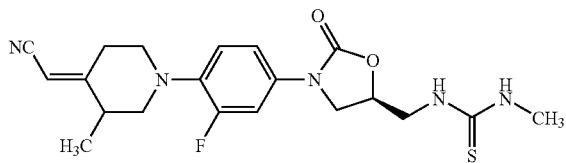

The title compound was prepared as per procedure described in Example 52 in by using (S)-N-{3-[4-(4-cyanomethylidene-3-methylpiperidin-1-yl)-3-fluorophenyl]-2-oxo-oxazolidin-5-ylmethyl}-thioisocyanate in 45% yield.

P. 180-182° C. and MS (M+1)=418 (MH+, 100%), M.F.=$C_{20}H_{24}FN_5O_2S$.

Example 70

(S)-N-{3-[4-(4-cyanomethylidene-3,3-dimethylpiperidin-1-yl)-3-fluorophenyl]-2-oxo-oxazolidin-5-ylmethyl}-acetamide

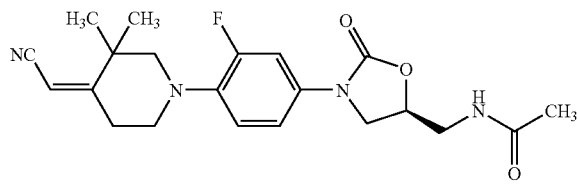

The title compound was prepared by following the procedure of Example 1 and by using (S)-{3-[4-(3,3-dimethyl-4-oxo-piperidin-1-yl)-3-fluorophenyl]-2-oxo-oxazolidin-5-ylmethyl}-acetamide in 78% yield.

M.P. 150-152° C. and MS (M+1)=401 (MH+, 100%), M.F.=$C_{21}H_{25}FN_4O_3$.

Example 71

(R)-{3-[4-(4-cyanomethylidene-3,3-dimethylpiperidin-1-yl)-3-fluorophenyl]-2-oxo-oxazolidin-5-ylmethyl}-methanesulphonate

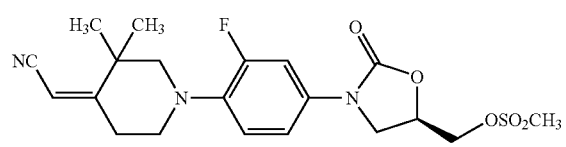

The title compound was prepared by following the procedure of Example-1 and by using (S)-{3-[4-(3,3-dimethyl-4-oxo-piperidin-1-yl)-3-fluorophenyl]-2-oxo-oxazolidin-5-ylmethyl}-methanesulfonate in 69% yield.

MS (M+1)=438 (MH+, 100%), M.F.=$C_{20}H_{24}FN_3O_5S$.

Example 72

(S)-N-{3-[4-(4-(1-cyanoethylidene)-piperidin-1-yl)-phenyl]-2-oxo-oxazolidin-5-ylmethyl}-acetamide

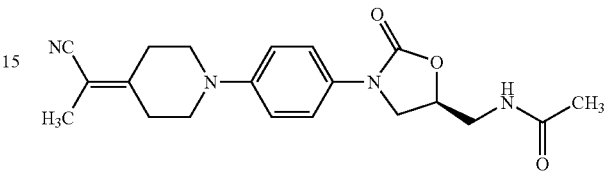

The title compound was prepared by following the procedure of Example 1 and by using (S)-{3-[4-(4-oxo-piperidin-1-yl)-phenyl]-2-oxo-oxazolidin-5-ylmethyl}-acetamide and diethyl-(1-cyanoethyl)-phosphonate in 65% yield.

M.P. 94-96° C. and MS (M+1)=369 (MH+, 100%), M.F.=$C_{20}H_{24}N_4O_3$.

Example 73

(S)-N-{3-[4-(4-(1-cyanoethylidene)-piperidin-1-yl)-3-fluorophenyl]-2-oxo-oxazolidin-5-ylmethyl}-formamide

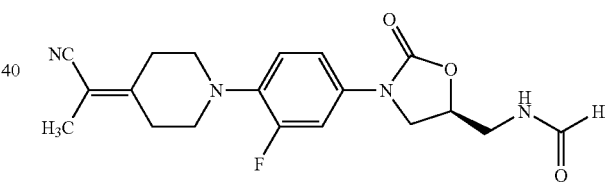

Step-1

Preparation of (S)-N-{3-[4-(4-(1-cyanoethylidene)-piperidin-1-yl)-3-fluorophenyl]-2-oxo-oxazolidin-5-ylmethyl}-amine.

The compound was prepared by following the procedure of Example-1 and by using (S)-{3-[4-(4-oxo-piperidin-1-yl)-3-fluorophenyl]-2-oxo-oxazolidin-5-ylmethyl}-amine and diethyl-(1-cyanoethyl)-phosphonate in 74% yield.

Step-2

The title compound was prepared by following the procedure of Example 2 and by using (S)-N-{3-[4-(4-(1-cyanoethylidene)-piperidin-1-yl)-3-fluorophenyl]-2-oxo-oxazolidin-5-ylmethyl}-amine in 66% yield.

M.P. 188-190° C. and MS (M+1)=373 (MH+, 100%), M.F.=$C_{19}H_{21}FN_4O_3$.

Example 74

(S)-N-{3-[4-(4-(1-cyanoethylidene)-piperidin-1-yl)-3-fluorophenyl]-2-oxo-oxazolidin-5-ylmethyl}-acetamide

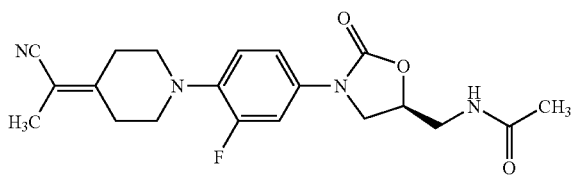

The title compound was prepared by following the procedure of Example-1 and by using (S)-{3-[4-(4-oxo-piperidin-1-yl)-3-fluorophenyl]-2-oxo-oxazolidin-5-ylmethyl}-acetamide and diethyl-(1-cyanoethyl)-phosphonate in 80% yield.
M.P. 181-182° C. and MS (M+1)=387 (MH$^+$, 100%) M.F.=$C_{20}H_{23}FN_4O_3$.

Example 75

(S)-N-{3-[4-(4-(1-cyanoethylidene)-piperidin-1-yl)-3-fluorophenyl]-2-oxo-oxazolidin-5-ylmethyl}-2-cyanoacetamide

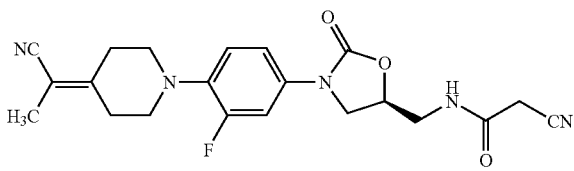

The title compound was prepared by following the procedure of Example 23 and by using (S)-N-{3-[4-(4-(1-cyanoethylidene)-piperidin-1-yl)-3-fluorophenyl]-2-oxo-oxazolidin-5-ylmethyl}-amine in 80% yield.
M.P. 194-196° C. and MS (M+1)=412 (MH$^+$, 100%), M.F.=$C_{21}H_{22}FN_5O_3$.

Example 76

(S)-N-{3-[4-(4-(1-cyanoethylidene)-piperidin-1-yl)-3-fluorophenyl]-2-oxo-oxazolidin-5-ylmethylamino}-carboxymethylamine

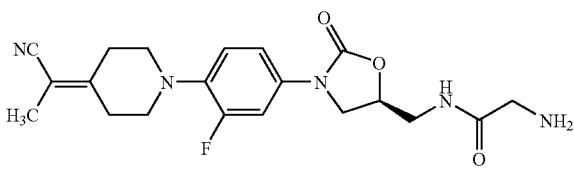

The title compound was prepared by following the procedure of Example-21 and by using (S)-N-{3-[4-(4-(1-cyanoethylidene)-piperidin-1-yl)-3-fluorophenyl]-2-oxo-oxazolidin-5-ylmethyl}-amine in 63% yield.
M.P. 141-142° C. and MS (M+1)=402 (MH$^+$, 100%), M.F.=$C_{20}H_{24}FN_5O_3$.

Example 77

(S)-N-{3-[4-(4-(1-cyanoethylidene)-piperidin-1-yl)-3-fluorophenyl]-2-oxo-oxazolidin-5-ylmethyl}-difluoroacetamide

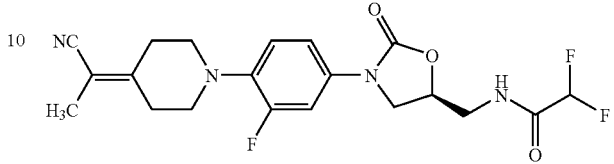

The title compound was prepared by following the procedure of Example 29 and by using (S)-N-{3-[4-(4-(1-cyanoethylidene)-piperidin-1-yl)-3-fluorophenyl]-2-oxo-oxazolidin-5-ylmethyl}-amine in 75% yield.
M.P. 172-174° C. and MS (M+1)=423 (MH$^+$, 100%), M.F.=$C_{20}H_{21}F_3N_4O_3$.

Example 78

(S)-N-{3-[4-(4-(1-cyanoethylidene)-piperidin-1-yl)-3-fluorophenyl]-2-oxo-oxazolidin-5-ylmethyl}-chloroacetamide

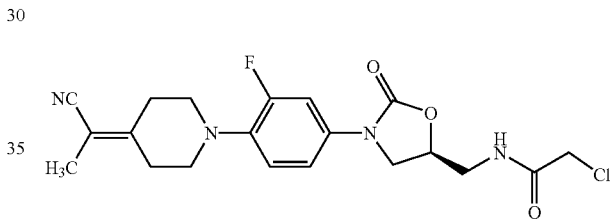

The title compound was prepared by following the procedure of Example 31 and by using (S)-N-{3-[4-(4-(1-cyanoethylidene)-piperidin-1-yl)-3-fluorophenyl]-2-oxo-oxazolidin-5-ylmethyl}-amine in 57% yield.
MS (M+1)=421 (MH$^+$, 100%), M.F.=$C_{20}H_{22}FN_4O_3Cl$.

Example 79

(S)-N-{3-[4-(4-(1-cyanoethylidene)-piperidin-1-yl)-3-fluorophenyl]-2-oxo-oxazolidin-5-ylmethyl}-dichloroacetamide

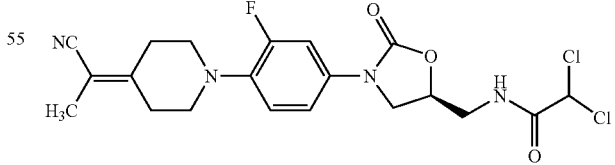

The title compound was prepared by following the procedure of Example 29 and by using (S)-N-{3-[4-(4-(1-cyanoethylidene)-piperidin-1-yl)-3-fluorophenyl]-2-oxo-oxazolidin-5-ylmethyl}-amine and dichloroacetic acid in 63% yield.
M.P. 202-204° C. and MS (M+1)=455 (MH$^+$, 100%), M.F.=$C_{20}H_{21}FN_4O_3Cl_2$.

Example 80

(S)-N-{3-[4-(4-(1-cyanoethylidene)-piperidin-1-yl)-3-fluorophenyl]-2-oxo-oxazolidin-5-ylmethyl}-trichloroacetamide

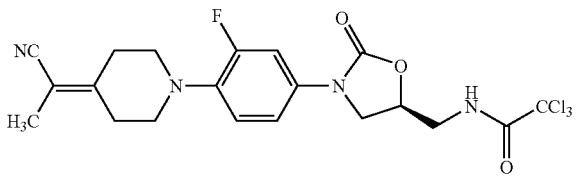

The title compound was prepared by following the procedure of Example 29 and by using (S)-N-{3-[4-(4-(1-cyanoethylidene)-piperidin-1-yl)-3-fluorophenyl]-2-oxo-oxazolidin-5-ylmethyl}-amine and trichloroacetic acid in 45% yield.

M.P. 166-168° C. and MS (M+1)=489 (MH$^+$, 100%), M.F.=$C_{20}H_{20}FN_4O_3Cl_3$.

Example 81

(S)-N-{3-[4-(4-(1-cyanoethylidene)-piperidin-1-yl)-3-fluorophenyl]-2-oxo-oxazolidin-5-ylmethyl}-isobutylcarbamate

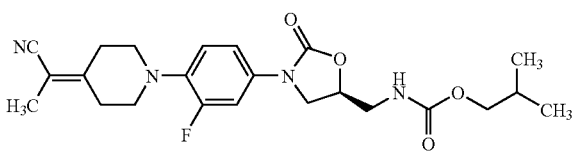

The title compound was prepared by following the procedure of Example-58 and by using (S)-N-{3-[4-(4-(1-cyanoethylidene)-piperidin-1-yl)-3-fluorophenyl]-2-oxo-oxazolidin-5-ylmethyl}-amine in 63% yield.

M.P. 158-160° C. and MS (M+1)=445 (MH$^+$, 100%), M.F.=$C_{23}H_{29}FN_4O_4$.

Example 82

(R)-{3-[4-(4-(1-cyanoethylidene)-piperidin-1-yl)-3-fluorophenyl]-2-oxo-oxazolidin-5-ylmethyl}-alcohol

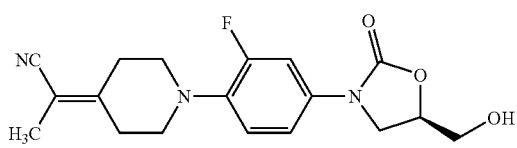

The title compound was prepared by following the procedure of Example 1 and by using (R)-{3-[4-(4-oxo-piperidin-1-yl)-3-fluorophenyl]-2-oxo-oxazolidin-5-ylmethyl}-alcohol and diethyl(1-cyanoethyl)-phosphonate in 63% yield.

M.P. 100-102° C. and MS (M+1)=346 (MH$^+$, 100%), M.F.=$C_{18}H_{20}FN_3O_3$.

Example 83

(R)-3-{3-[4-(4-(1-cyanoethylidene)-piperidin-1-yl)-3-fluorophenyl]-2-oxo-oxazolidin-5-ylmethyloxy}-iso-oxazole

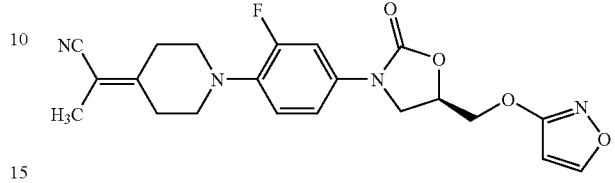

The mixture of diisopropyldiazodicarboxylate (3.75 mmol), (R)-{3-[4-(4-(1-cyanoethylidene)-piperidin-1-yl)-3-fluorophenyl]-2-oxo-oxzzolidin-5-ylmenthyl}-alcohol (3.13 mmol), triphenylphosphine (3.44 mmol) and 3-hydroxy-isoxazole (3.44 mmol) in tetrahydrofuran (20 ml) was stirred for 2 hours. The reaction mixture was extracted with the ethyl acetate water mixture and the combine organic layer was dried. Evaporation of the solvent afforded a sticky solid, which was upon silica gel colmn chromatography afforded the title compound in 70% yield.

M.P. 137-138° C. and MS (M+1)=413 (MH$^+$, 100%), M.F.=$C_{21}H_{21}FN_4O_4$.

Example 84

(S)-N-{3-[4-(4-(1-cyanoethylidene)-piperidin-1-yl)-3-fluorophenyl]-2-oxo-oxazolidin-5-ylmethyl}-thio-acetamide

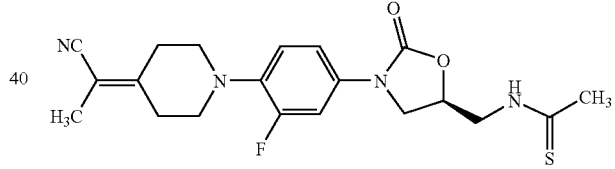

The title compound was prepared as per procedure described in Example 45 by using (S)-N-{3-[4-(4-(1-cyanoethylidene)-piperidin-1-yl)-3-fluorophenyl]-2-oxo-oxazolidin-5-ylmethyl}-acetamide in 56% yield.

M.P. 171-172° C. and MS (M+1)=403 (MH$^+$, 100%). M.F.=$C_{20}H_{23}FN_4O_2S$

Example 85

E/Z Mixture of (S)-N-{3-[4-(4-(1-cyanoethylidene)-3-fluoropiperidin-1-yl)-3-fluorophenyl]-2-oxo-oxazolidin-5-ylmethyl}-acetamide

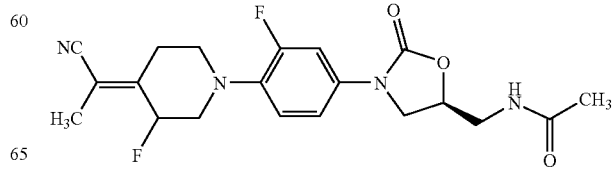

The title compound was prepared as per procedure described in Example 1 by using (S)-{3-[4-(3-fluoro-4-oxo-piperidin-1-yl)-3-fluorophenyl]-2-oxo-oxazolidin-5-ylmethyl}-acetamide and diethyl-(1cyanoethyl)-phosphonate in 75% yield as a isomeric mixture.

M.P. 148-150° C. and MS (M+1)=405 (MH$^+$, 100%), M.F.=$C_{20}H_{22}F_2N_4O_3$.

Example 86

E-(S)-N-{3-[4-(4-(1-cyanoethylidene)-3-fluoropiperidin-1-yl)-3-fluorophenyl]-2-oxo-oxazolidin-5-ylmethyl}-acetamide

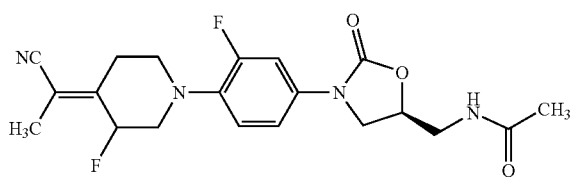

Isomeric mixture obtained as per Example 85 was separated on preparative HPLC to provide title compound in 42% yield.

M.P. 148-150° C. and MS (M+1)=405 (MH$^+$, 100%), M.F.=$C_{20}H_{22}F_2N_4O_3$.

Example 87

Z-(S)-N-{3-[4-(4-(1-cyanoethylidene)-3-fluoropiperidin-1-yl)-3-fluorophenyl]-2-oxo-oxazolidin-5-ylmethyl}-acetamide

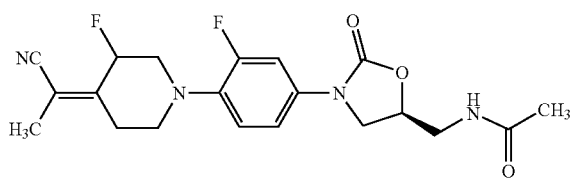

Isomeric mixture obtained as per Example 85 was separated on preparative HPLC to provide title compound in 22% yield.

M.P. 148-150° C. and MS (M+1)=405 (MH$^+$, 100%), M.F.=$C_{20}H_{22}F_2N_4O_3$.

Example 88

(S)-N-{3-[4-(4-(1-cyanopropylidene)-piperidin-1-yl)-phenyl]-2-oxo-oxazolidin-5-ylmethyl}-acetamide

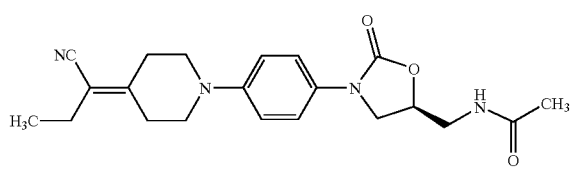

The title compound was prepared as per procedure described in Example 1 by using (S)-{3-[4-(4-oxo-piperidin-1-yl)-phenyl]-2-oxo-oxazolidin-5-ylmethyl}-acetamide and diethyl-(1-cyanopropyl)-phosphonate in 78% yield.

MS (M+1)=383 (MH$^+$, 100%), M.F.=$C_{21}H_{26}N_4O_3$.

Example 89

(S)-N-{3-[4-(4-(1-cyanopropylidene)-piperidin-1-yl)-3-fluorophenyl]-2-oxo-oxazolidin-5-ylmethyl}-acetamide

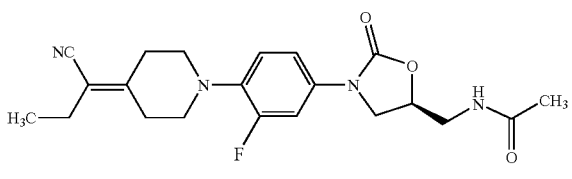

The title compound was prepared as per procedure described in Example 1 by using (S)-{3-[4-(4-oxo-piperidin-1-yl)-3-fluorophenyl]-2-oxo-oxazolidin-5-ylmethyl}-acetamide and diethyl-(1-cyanopropyl)-phosphonate in 61% yield.

Mp. 185-186° C. $^1$H-NMR (CDCl$_3$, 200 MHz): δ 1.20 (3H, t, J=5.00 Hz), 2.05 (3H, s), 2.30 (2H, q, J=6.5 Hz), 2.50-2.65 (2H, m), 2.75-2.85 (2H, m), 3.00-3.25 (3H, m), 3.95-4.15 (1H, m), 4.65-4.85 (1H, m), 6.05-6.10 (1H, m), 6.90 (1H, dd, J=9.2, 9.2 Hz), 7.05 (1H, dd, J=2.2, 2.2 Hz), 7.41 (1H, dd, J=2.2, 14.0 Hz).

ESMS m/z 401 (MH$^+$, 100%).

Example 90

(S)-N-{3-[4-(4-(1-cyanopropylidene)-piperidin-1-yl)-3-fluorophenyl]-2-oxo-oxazolidin-5-ylmethyl}-dichloroacetamide

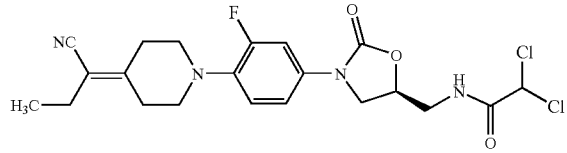

Step-1

Preparation of (S)-N-{3-[4-(4-cyanopropylidene-piperidin-1-yl)-3-fluorophenyl]-2-oxo-oxazolidin-5-ylmethyl}-amine.

The compound was prepared by following the procedure of Example -1 and by using (S)-{3-[4-(4-oxo-piperidin-1-yl)-3-fluorophenyl]-2-oxo-oxazolidin-5-ylmethyl}-amine in 75% yield.

Step-2

The title compound was prepared by following the procedure of Example 29 and by using (S)-N-{3-[4-(4-cyanopropylidene-piperidin-1-yl)-3-fluorophenyl]-2-oxo-oxazolidin-5-ylmethyl}-amine and dichloroacetic acid in 50% yield.

M.P. 214-216° C. and MS (M+1)=469 (MH⁺, 100%), M.F.=C₂₁H₂₃FN₄O₃Cl₂.

Example 91

(S)-N-{3-[4-(4-(1-cyanopropylidene)-piperidin-1-yl)-3-fluorophenyl]-2-oxo-oxazolidin-5-ylmethyl}-trichloroacetamide

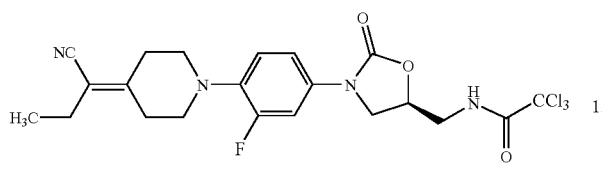

The title compound was prepared by following the procedure of Example 29 and by using (S)-N-{3-[4-(4-cyanopropylidene-piperidin-1-yl)-3-fluorophenyl]-2-oxo-oxazolidin-5-ylmethyl}-amine and trichloroacetic acid in 63% yield.

M.P. 150-152° C. and MS (M+1)=503 (MH⁺, 100%), M.F.=C₂₁H₂₂FN₄O₃Cl₃.

Example 92

(S)-N-{3-[4-(4-(1-cyanopropylidene)-piperidin-1-yl)-3-fluorophenyl]-2-oxo-oxazolidin-5-ylmethyl}-bromoacetamide

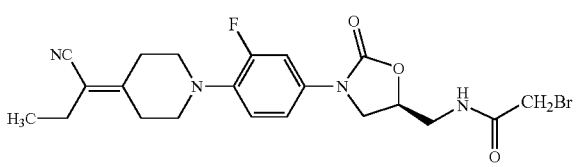

The title compound was prepared by following the procedure of Example 10 and by using (S)-N-{3-[4-(4-cyanopropylidene-piperidin-1-yl)-3-fluorophenyl]-2-oxo-oxazolidin-5-ylmethyl}-amine and bromoacetyl bromide in 65% yield.

M.P. 200-203° C. and MS (M+1)=480 (MH⁺, 100%), M.F.=C₂₁H₂₄FN₄O₃Br.

Example 93

(S)-N-{3-[4-(4-(1-cyanopropylidene)-piperidin-1-yl)-3-fluorophenyl]-2-oxo-oxazolidin-5-ylmethyl}-thioacetamide

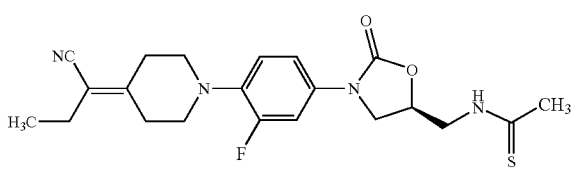

The title compound was prepared by following the procedure of Example 45 and by using (S)-N-{3-[4-(4-(1-cyanopropylidene)-piperidin-1-yl)-3-fluorophenyl]-2-oxo-oxazolidin-5-ylmethyl}-acetamide in 55% yield.

M.P. 174-176° C. and MS (M+1)=417 (MH⁺, 100%), M.F.=C₂₁H₂₅FN₄O₂S

Example 94

(S)-N-{3-[4-(4-(1-cyano-cyclopropylmethylidene)-piperidin-1-yl)-3-fluorophenyl]-2-oxo-oxazolidin-5-ylmethyl}-acetamide

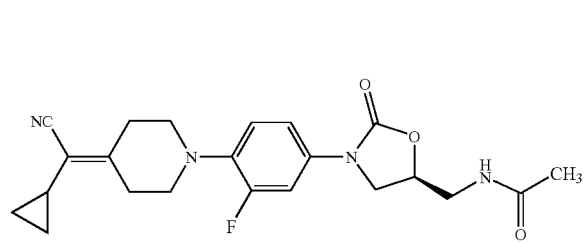

The mixture of (S)-N-{3-[4-(4-oxo-piperidin-1-yl)-3-fluorophenyl]-2-oxo-oxazolidin-5-ylmethyl}-acetamide (2.86 mmol), cyclopropylacetonitrile (5.73 mmol), ammonium acetate (catalytic) in 100 ml of toluene was heated at reflux temperature for 5 to 6 hours. The reaction mixture was cooled to room temperature and extracted with ethyl acetate water mixture, dried and evaporated to give crude product. The crude product was recrystallized from ethyl acetate to furnish title compound in 69% yield.

Mp: 175-79° C.

¹H-NMR (CDCl₃, 200 MHz): δ 0.70-0.80 (2H, m), 0.81-1.00 (2H, m), 1.60-1.70 (1H, m), 2.05 (3H, m), 2.65-2.80 (4H, m), 3.01-3.30 (4H, m), 360-3.81 (1H, m), 3.85-4.15 (3H, m), 4.71-4.85 (1H, m), 6.97 (1H, m), 7.10 (1H, m), 7.45 (1H, m).

ESMS m/z 413 (MH⁺, 100%).

Example 95

(S)-N-{3-[4-(4-(1-cyano-3-ene-butylidene)-piperidin-1-yl)-3-fluorophenyl]-2-oxo-oxazolidin-5-ylmethyl}-acetamide

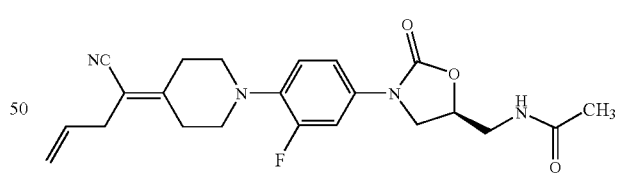

The title compound was prepared as per procedure described in Example 1 by using (S)-{3-[4-(4-oxo-piperidin-1-yl)-3-fluorophenyl]-2-oxo-oxazolidin-5-ylmethyl}-acetamide and diethyl-(1-cyano-3-ene-butyl)-phosphonate in 67% yield.

Mp. 189-191° C.

¹H-NMR (CDCl₃, 200 MHz): δ 2.01 (3H, s), 2.51-2.61 (2H, m), 2.78-2.90 (2H, m), 3.00-3.20 (6H, m), 3.55-3.82 (3H, m), 3.95-4.10 (1H, m), 4.70-44.85 (1H, m) 5.10-5.22 (2H, m), 5.70-5.90 (1H, m), 6.00-6.10 (1H, m), 6.90 (1H, m), 7.05 (1H, m), 7.44 (1H, m).

ESMS m/z 413 (MH⁺, 100%).

Example 96

(S)-N-{3-[4-(4-(1-cyano-3-yne-butylidene)-piperidin-1-yl)-3-fluorophenyl]-2-oxo-oxazolidin-5-ylmethyl}-acetamide

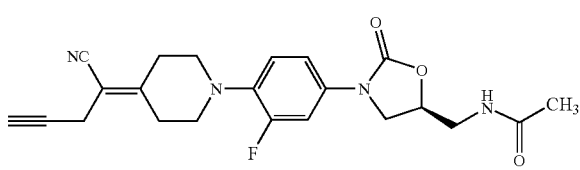

The title compound was prepared as per procedure described in Example 1 by using (S)-{3-[4-(4-oxo-piperidin-1-yl)-3-fluorophenyl]-2-oxo-oxazolidin-5-ylmethyl}-acetamide and diethyl-(1-cyano-3-yne-butyl)-phosphonate in 54% yield.

M.P. 171-172° C. and MS (M+1)=411 (MH+, 100%), M.F.=$C_{22}H_{23}FN_4O_3$.

Example 97

(S)-N-{3-[4-(4-(1-cyano-2-phenyl-ethylidene)-piperidin-1-yl)-3-fluorophenyl]-2-oxo-oxazolidin-5-ylmethyl}-acetamide

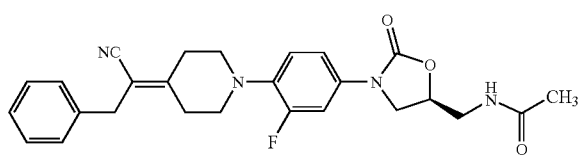

The title compound was prepared as per procedure described in Example 1 by using (S)-{3-[4-(4-oxo-piperidin-1-yl)-3-fluorophenyl]-2-oxo-oxazolidin-5-ylmethyl}-acetamide and diethyl-(1-cyano-1-benzylmethyl)-phosphonate in 40% yield.

Mp. 98-100° C.

$^1$H-NMR (CDCl$_3$, 200 MHz): δ 2.05 (3H, s), 2.60-2.79 (2H, m), 2.80-2.90 (2H, m), 3.05-3.21 (4H, m), 3.50-3.80 (5H, m), 3.95-4.10 (1H, m), 4.70-4.85 (1H, m), 6.00 (1H, t), 6.90 (1H, m), 7.05 (1H, m), 7.20-7.39 (6H, m), 7.41 (1H, m).

Example 98

(S)-N-{3-[4-(4-(1-cyano-1-phenyl-methylidene)-piperidin-1-yl)-3-fluorophenyl]-2-ox-oxazolidin-5-ylmethyl}-acetamide

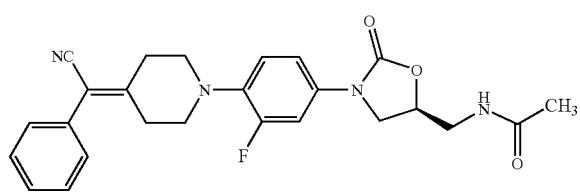

The title compound was prepared as per procedure described in Example 94 by using phenylacetonitrile in the place of cyclopropylacetonitrile in 62% yield.

Mp. 200-205° C.

$^1$H-NMR (CDCl$_3$, 200 MHz): δ 2.01 (3H, s), 2.60-2.70 (2H, m), 2.90-3.10 (4H, m), 3.21-3.35 (2H, m), 3.55-3.85 (3H, m), 3.97-4.10 (1H, m), 4.70-4.90 (1H, m), 6.00 (1H, t), 6.85-7.19 (2H, m), 7.30-7.59 (6H, m).

ESMS m/z 449 (MH+, 100%).

Example 99

(S)-N-{3-[4-(4-(1-cyano-1-(3,4-difluorophenyl)-methylidene)-piperidin-1-yl)-3-fluorophenyl]-2-oxo-oxazolidin-5-ylmethyl}-acetamide

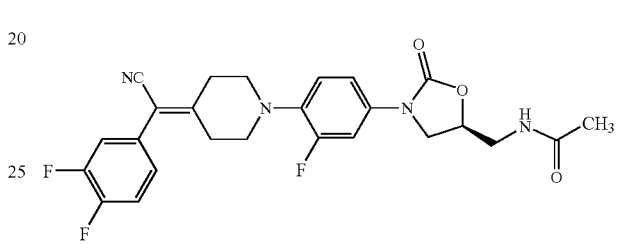

The title compound was prepared as per procedure described in Example 94 by using 3,4-difluorophenylacetonitrile in the place of cyclopropylacetonitrile in 54% yield.

Mp: 180-183° C.

$^1$H-NMR (CDCl$_3$, 200 MHz): δ 2.01 (3H, s), 2.57-2.69 (2H, m), 2.90-3.10 (4H, m), 3.19-3.30 (2H, m), 3.65-3.80 (3H, m), 3.90-4.10 (1H, m), 4.69-4.85 (1H, m), 6.10 (1H, m), 6.95 (1H, m), 7.00-7.30 (4H, m), 7.45 (1H, m).

ESMS m/z 485 (MH+, 100%).

Example 100

(S)-N-{3-[4-(4-(1-cyano-1-(pyridin-2-yl)-methylidene)-piperidin-1-yl)-3-fluorophenyl]-2-oxo-oxazolidin-5-ylmethyl}-acetamide

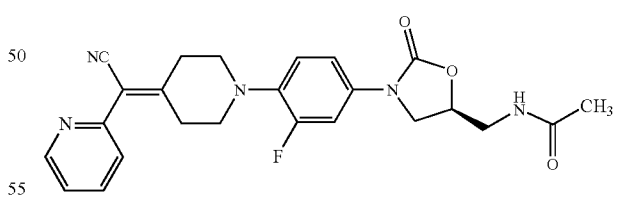

The title compound was prepared as per procedure described in Example-94 by using pyridin-2-ylacetonitrile in the place of cyclopropylacetonitrile in 62% yield.

Mp. 265-267° C.

$^1$H-NMR (CDCl$_3$, 200 MHz): δ 2.00 (3H, s), 2.79-3.02 (4H, m), 3.10-3.20 (2H, m), 3.30-3.40 (2H, m), 3.50-3.85 (3H, m), 3.90-4.10 (1H, m), 4.61-4.90 (1H, m), 6.10-6.30 (1H, m), 6.95-7.10 (2H, m), 7.30 (1H, m), 7.40 (2H, m), 7.70-7.90 (1H, m), 8.69 (1H, m).

ESMS m/z 450 (MH+, 100%).

Example 101

(S)-N-{3-[4-(4-(1-cyano-2-(morpholin-1-yl)-eth-ylidene)-piperidin-1-yl)-3-fluorophenyl]-2-oxo-oxazolidin-5-ylmethyl}-acetamide

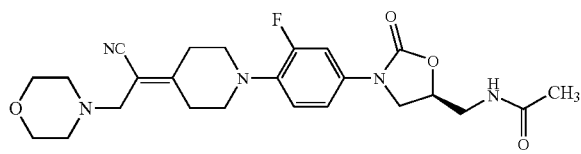

The title compound was prepared as per procedure described in Example 1 by using (S)-{3-[4-(4-oxo-piperidin-1-yl)-3-fluorophenyl]-2-oxo-oxazolidin-5-ylmethyl}-acetamide and diethyl [1-cyano(2-morpholin-1-yl)-ethyl]- in 43% yield.

MS (M+1)=472 (MH$^+$, 100%), M.F.=$C_{24}H_{30}FN_5O_4$.

Example 102

(S)-N-{3-[4-(4-(1-cyano-1-(imidazol-1-yl)-methylidene)-piperidin-1-yl)-3-fluorophenyl]-2-oxo-oxazolidin-5-ylmethyl}-acetamide

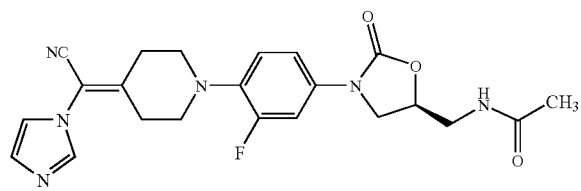

The title compound was prepared as per procedure described in Example 94 by using 1-imidazolylacetonitrile in the place of cyclopropylacetonitrile in 33% yield.

M.P. 196-198° C. and MS (M+1)=439 (MH$^+$, 100%), M.F.=$C_{22}H_{23}FN_6O_3$.

Example 103

(S)-N-{3-[4-(4-(1-cyano-1-(2-methyl-imidazol-1-yl)-methylidene)-piperidin-1-yl)-3-fluorophenyl]-2-oxo-oxazolidin-5-ylmethyl}-acetamide

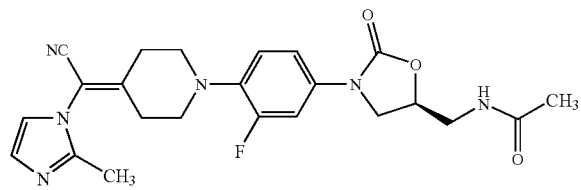

The title compound was prepared as per procedure described in Example 94 by using 1-(2-methyl-imidazoyl)acetonitrile in the place of cyclopropylacetonitrile in 27% yield.

M.P. 204-206° C. and MS (M+1)=453 (MH$^+$, 100%), M.F.=$C_{23}H_{25}FN_6O_3$.

Example 104

(S)-N-{3-[4-(4-(1-cyano-1-(1,2,4-triazol-1-yl)-methylidene)-piperidin-1-yl)-3fluorophenyl]-2-oxo-oxazolidin-5-ylmethyl}-acetamide

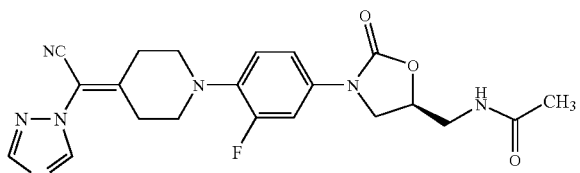

The title compound was prepared as per procedure described in Example 94 by using 1-(1,2,4-triazolyl)acetonitrile in the place of cyclopropylacetonitrile in 39% yield.

M.P. 194-196° C. and MS (M+1)=440 (MH$^+$, 100%), M.F.=$C_{21}H_{22}FN_7O_3$.

Example 105

(S)-N-{3-[4-(4-(1-cyano-1-(thiophen-2-yl)-methylidene)-piperidin-1-yl)-3-fluorophenyl]-2-oxo-oxazolidin-5-ylmethyl}-acetamide

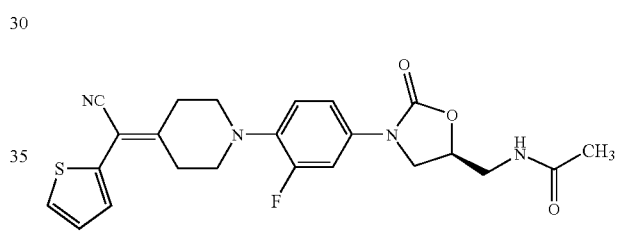

The title compound was prepared as per procedure described in Example 94 by using (thiophen-2-yl)acetonitrile in the place of cyclopropylacetonitrile in 56% yield.

Mp. 260-63° C.

$^1$H-NMR (CDCl$_3$, 200 MHz): δ 2.01 (31H, s), 2.80-2.85 (2H, m), 2.90-3.01 (2H, m), 3.05-3.19 (2H, m), 3.20-3.30 (2H, m), 3.59-3.80 (3H, m), 3.95-4.10 (1H, m), 4.70-4.81 (1H, m), 6.01 (1H,t), 6.90 (1H, m), 7.00-7.19 (4H, m), 7.35-7.50 (1H, m).

ESMS m/z 455 (MH$^+$, 100%).

Example 106

(S)-N-{3-[4-(4-(1,1-dicyano-methylidene)-piperidin-1-yl)-3-fluorophenyl]-2-oxo-oxazolidin-5-ylmethyl}-acetamide

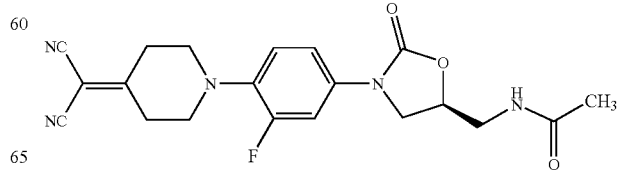

The title compound was prepared as per procedure described in Example 94 by using malanonitrile in the place of cyclopropylacetonitrile in 79% yield.

Mp. 158-160° C.

¹H-NMR (CDCl₃, 200 MHz): δ 2.01 (3H, s), 3.00-3.15 (4H, m), 3.21-3.41 (4H, m), 3.50-3.81 (3H, m), 3.92-4.10 (1H, m), 4.70-4.90 (1H, m), 59.0-6.05 (1H, m), 7.10 (1H, m), 7.20 (1H, m), 7.60 (1H, m)

ESMS m/z 398 (MH⁺, 100%).

Example 107

(S)-N-{3-[4-(4-(1-cyano-1-carboxamido-methylidene)-piperidin-1-yl)-3-fluorophenyl]-2-oxo-oxazolidin-5-ylmethyl}-acetamide

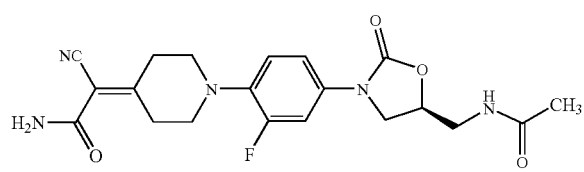

The title compound was prepared as per procedure described in Example 94 by using carboxamidoacetonitrile in the place of cyclopropylacetonitrile in 68% yield.

Mp. 157-159° C.

¹H-NMR (CDCl₃, 200 MHz): δ 2.05 (3H, s), 2.81-3.00 (4H, m), 3.15-3.33 (4H, m), 3.52-3.70 (3H, m), 3.70-3.90 (1H, m), 4.75-5.01 (1H, m), 7.01-7.20 (2H, m), 7.50 (1H, m).

ESMS m/z 416 (MH⁺, 100%).

Example 108

(S)-N-{3-[4-(4-(1-cyano-1-(N-prop-2-ene-carboxamido)-methylidene)-piperidin-1-yl)-3-fluorophenyl]-2-oxo-oxazolidin-5-ylmethyl}-acetamide

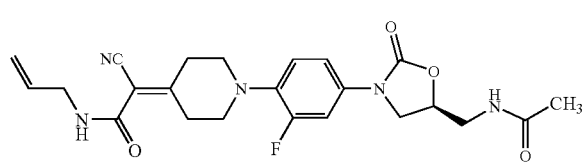

The title compound was prepared as per procedure described in Example 94 by using Nprop-2-ene-aminocarbonylacetonitrile in the place of cyclopropylacetonitrile in 59% yield.

Mp: 168-170° C.

¹H-NMR (CDCl₃, 200 MHz): δ 2.01 (3H, s), 2.81-2.95 (2H, m), 3.15-3.40 (6H, m), 3.60-3.81 (3H, m) 3.92-4.10 (3H, m), 4.70-4.85 (1H, m), 5.18-5.38 (2H, m), 5.75-5.95 (1H, m), 6.05 (1H, t), 6.30-6.40 (1H, m), 6.90 (1H, m), 7.10 (1H, m), 7.50 (1H, m)

ESMS m/z 456 (MH⁺, 100%).

Example 109

(S)-N-{3-[4-(4-(1-cyano-1-(N-cyclopropyl-carboxamido)-methylidene)-piperidin-1-yl)-3-fluorophenyl]-2-oxo-oxazolidin-5-ylmethyl}-acetamide

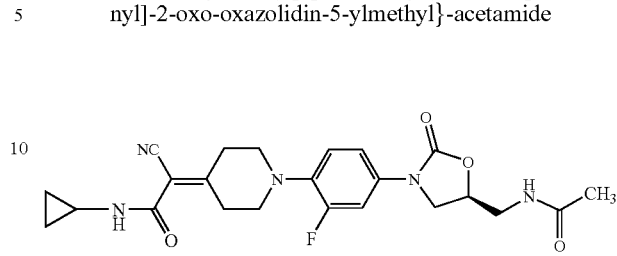

The title compound was prepared as per procedure described in Example 94 by using N-cyclopropylaminocarbonylacetonitrile in the place of cyclopropylacetonitrile in 44% yield.

Mp: 210-212° C.

¹H-NMR (CDCl₃, 200 MHz): δ 0.58-0.65 (2H, m), 0.80-0.92 (2H, m), 2.05 (3H, s), 2.75-2.95 (3H, m), 3.15-3.25 (4H, m), 3.30-3.41 (2H, m), 3.60-3.81 (3H, m), 3.90-3.41 (1H, m), 4.70-4.85 (1H, m), 5.95-6.10 (1H, m), 6.30-6.40 (1H, m), 695 (1H, m), 7.10 (1h, m), 7.45 (1H, m)

ESMS m/z 456 (MH⁺, 100%).

Example 110

(S)-N-{3-[4-(4-(1-cyano-1-(N-cyclohexyl-carboxamido)-methylidene)-piperidin-1-yl)-3-fluorophenyl]-2-oxo-oxazolidin-5-ylmethyl}-acetamide

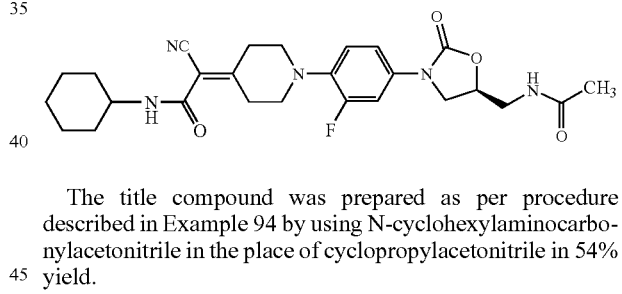

The title compound was prepared as per procedure described in Example 94 by using N-cyclohexylaminocarbonylacetonitrile in the place of cyclopropylacetonitrile in 54% yield.

Mp. 195-198° C.

¹H-NMR (CDCl₃, 200 MHz): δ 1.10-155 (m, 6H), 1.58-1.82 (4H, m), 1.90-2.05 (1H, m) 2.05 (3H, s), 2.80-2.90 (2H, m), 3.10-3.42 (6H, m), 3.52-3.81 (4H, m), 3.97-4.10 (1H, m), 4.70-4.90 (1H, m), 5.99-6.20 (2H, m), 6.95 (1H, m), 7.10 (1H, m), 7.49 (1H, m)

ESMS m/z 498 (MH⁺, 100%).

Example 111

(S)-N-{3-[4-(4-(1-cyano-1-(pyrrolidin-1-yl-carbonyl)-methylidene)-piperidin-1-yl)-3-fluorophenyl]-2-oxo-oxazolidin-5-ylmethyl}-acetamide

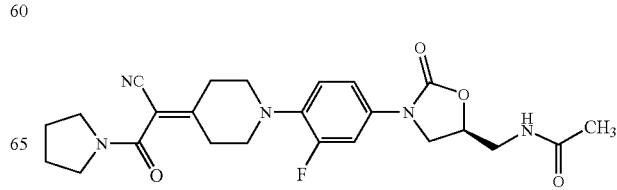

The title compound was prepared as per procedure described in Example 94 by using N-pyrrolidinylcarbonylacetonitrile in the place of cyclopropylacetonitrile in 38% yield.

Mp: 125-128° C.

¹H-NMR (CDCl₃, 200 MHz): δ 1.90-2.10 (4H, m), 2.00 (3H, s), 2.65-2.79 (2H, m), 2.83-2.90 (2H, m), 3.10-3.30 (4H, m), 3.48-3.60 (4H, m), 3.61-3.80 (3H m), 3.95-4.10 (1H, m), 4.70-4.85 (1H, m), 6.05 (1H, t), 6.90 (1H, m), 7.10 (1H, m), 7.45 (1H, m)

ESMS m/z 470 (MH⁺, 100%).

Example 112

(S)-N-{3-[4-(4-(1-cyano-1-(morpholin-1-yl-carbonyl)-methylidene)-piperidin-1-yl)-3-fluorophenyl]-2-oxo-oxazolidin-5-ylmethyl}-acetamide The title compound was prepared as per procedure described in Example 94 by using N-morpholinylcarbonylacetonitrile in the place of cyclopropylacetonitrile in 62% yield.

Mp. 145-146° C.

¹H-NMR (CDCl₃, 200 MHz): δ 2.05 (3H, s), 2.60-2.70 (2H, m), 2.80-2.90 (2H, m), 3.10-3.30 (4H, m), 3.50-3.85 (11H, m), 3.95-4.10 (1H, m), 4.70-4.82 (1H, m), 6.05-6.20 (1H, m), 6.95 (1H, m), 7.10 (1H, m), 7.45 (1H, m)

ESMS m/z 486 (MH⁺, 100%).

Example 113

(S)-N-{3-[4-(4-(1-cyano-3-hydroxy-propylidene)-piperidin-1-yl)-3-fluorophenyl]-2-oxo-oxazolidin-5-ylmethyl}-acetamide The title compound was prepared as per procedure described in Example 1 by using S)-{3-[4-(4-oxo-piperidin-1-yl)-3-fluorophenyl]-2-oxo-oxazolidin-5-ylmethyl}-acetamide and diethyl (1-cyano-3-hydroxypropyl)phosphonate in 45% yield.

M.P. 192-194° C. and MS (M+1)=417 (MH⁺, 100%), M.F.=$C_{21}H_{25}FN_4O_4$.

Example 114

(S)-N-{3-[4-(4-(1-cyano-1-ethoxycarbonyl-methylidene)-piperidin-1-yl)-3-fluorophenyl]-2-oxo-oxazolidin-5-ylmethyl}-acetamide

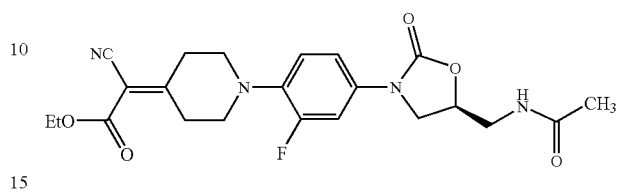

The title compound was prepared as per procedure described in Example 94 by using ethoxycarbonylacetonitrile in the place of cyclopropylacetonitrile in 79% yield.

Mp. 165-169° C.

¹H-NMR (CDCl₃, 200 MHz): δ 1.40 (3H, t), 2.01 (3H, s), 2.90-3.01 (2H, m), 3.18-3.40 (6H, m), 3.50-3.80 (3H, m), 3.95-4.10 (1H, m), 4.21-4.40 (2H, m), 4.70-4.90 (1H, m), 5.95 (1H, t), 6.95 (1H, m), 7.10 (1H, m), 7.45 (1H, m)

ESMS m/z 445 (MH⁺, 100%).

Example 115

(S)-N-{3-[4-(4-(1-cyano-1-methylmercapto-methylidene)-piperidin-1-yl)-3-fluorophenyl]-2-oxo-oxazolidin-5-ylmethyl}-acetamide

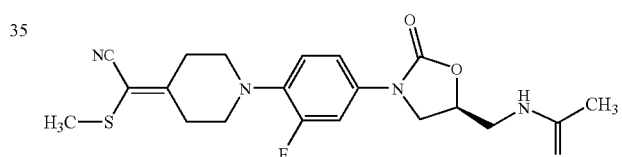

The title compound was prepared as per procedure described in Example 94 by using methylmercaptoacetonitrile in the place of cyclopropylacetonitrile in 56% yield.

Mp: 205-207° C.

¹H-NMR (CDCl₃, 200 MHz): δ 2.01 (31H, s), 2.41 (3H, s), 2.70-2.90 (4H, m), 3.10-3.21 (4H, m), 3.60-3.81 (3H, m), 3.90-4.11 (1H, m), 4.70-4.90 (1H, m), 6.10-6.21 (1H, m), 6.95 (1H, m), 7.10 (1H, m), 7.45 (1H, m).

ESMS m/z 419 (MH⁺, 100%).

Example 116

(S)-N-{13-[4-(4-(1-cyano-1-phenylmercapto-methylidene)-piperidin-1-yl)-3-fluorophenyl]-2-oxo-oxazolidin-5-ylmethyl}-acetamide

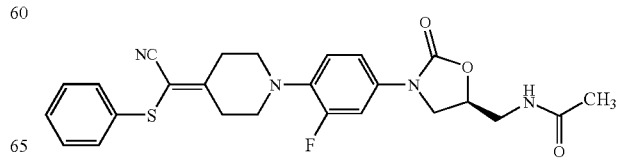

The title compound was prepared as per procedure described in Example 94 by using phenylmercaptoacetonitrile in the place of cyclopropylacetonitrile in 61% yield.

Mp. 148-150° C.

ESMS m/z 481 (MH+, 100%).

Example 117

(S)-N-{3-[4-(4-(1-cyano-1-bromo-methylidene)-piperidin-1-yl)-3-fluorophenyl]-2-oxo-oxazolidin-5-ylmethyl}-acetamide

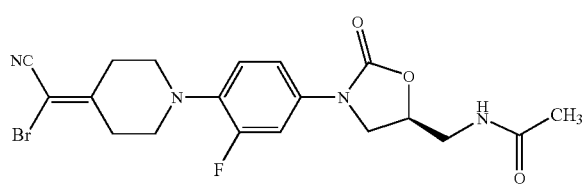

The mixture of S)-{3-[4-(4-cyanomethylidene-piperidin-1-yl)-3-fluorophenyl]-2-oxo-oxazolidin-5-ylmethyl}-acetamide (0.12 mmol) and bromine (0.72 mmol) in 25 ml chloroform was stirred at reflux for 2 hours.

Chloroform was evaporated under vacuum and the residue was chromatographed on the silica gel to afford the title compound in 39% yield.

M.P. 148-150° C. and MS (M+1)=452 (MH+, 100%), M.F.=$C_{19}H_{20}BrFN_4O_3$.

Example 118

(S)-N-{3-[4-(4-(1-cyano-1-(pyridin-2-yl)-methylidene)-piperidin-1-yl)-3-fluorophen]-2-oxo-oxazolidin-5-ylmethyl}-thioacetamide

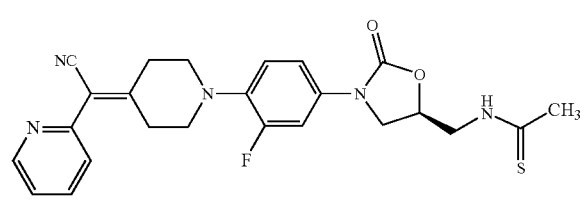

The title compound was prepared as per procedure described in Example 45 by using (S)-N-{3-[4-(4-(1-cyano-1-(pyridin-2-yl)-methylidene)-piperidin-1-yl)-3-fluorophenyl]-2-oxo-oxazolidin-5-ylmethyl}-acetamide in 39% yield.

M.P. 110-115° C. and MS (M+1)=466 (MH+, 100%), M.F.=$C_{24}H_{24}FN_5O_2S$.

Example 119

(S)-N-{3-[4-(4-(1,1-dicyano-methylidene)-piperidin-1-yl)-3-fluorophenyl]-2-oxo-oxazolidin-5-ylmethyl}-thioacetamide

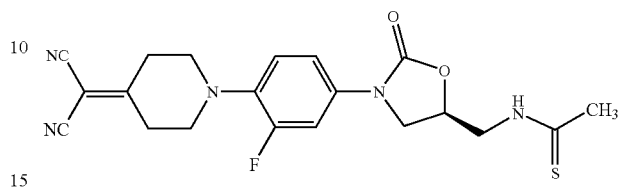

The title compound was prepared as per procedure described in Example 45 by using (S)-N-{3-[4-(4-(1,1-dicyano-methylidene)-piperidin-1-yl)-3-fluorophenyl]-2-oxo-oxazolidin-5-ylmethyl}-acetamide in 87% yield.

Mp. 210-212° C.

$^1$H-NMR (CDCl$_3$, 200 MHz): δ 2.60 (3H, m), 2.90-3.05 (4H, m), 3.20-3.40 (4H, m), 3.70-3.90 (1H, m), 4.00-4.20 (1H, m), 4.21-4.40 (1H, m), 4.9-5.10 (1H, m), 6.91-7.19 (2H, m), 7.50 (1H, m), 8.02-8.12 (1H, m).

ESMS m/z 414 (MH+, 100%).

Example 120

(S)-N-{3-[4-(4-(1-cyano-1-ethoxycarbonyl-methylidene)-piperidin-1-yl)-3-fluorophenyl]-2-oxo-oxazolidin-5-ylmethyl}-thioacetamide

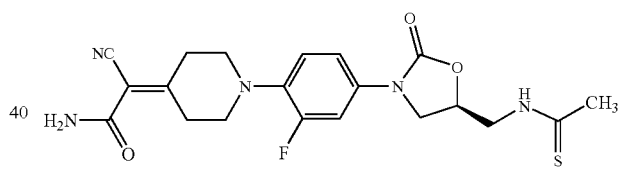

The title compound was prepared as per procedure described in Example 45 by using (S)-N-{3-[4-(4-(1-cyano-1-ethoxycarbonyl-methylidene)-piperidin-1-yl)-3-fluorophenyl]-2-oxo-oxazolidin-5-ylmethyl}-acetamide in 75% yield.

Mp. 182-85° C.

ESMS m/z 432 (MH+, 100%)

Example 121

(S)-N-{3-[4-(4-(1-cyano-1-(morpholin-1-yl-thiocarbonyl)-methylidene)-piperidin-1-yl)-3-fluorophenyl]-2-oxo-oxazolidin-5-ylmethyl}-thioacetamide

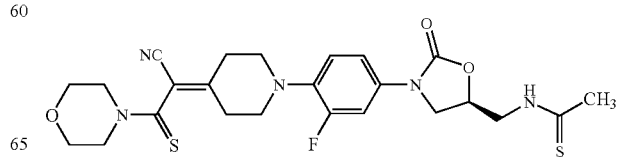

The mixture of (S)-N-{3-[4-(4-(1-cyano-1-(morpholin-1-yl-thiocarbonyl)-methylidene)-piperidin-1-yl)-3-fluorophenyl]-2-oxo-oxazolidin-5-ylmethyl}-acetamide (0.26 mmol), Lowesson's reagent (0.80 mmol) in dioxane (10 ml) was heated at 100° C. The reaction mixture was concentrated and the obtained residue was purified by silica gel column chromatography in 76% yield.

Mp. 180-182° C.

¹H-NMR (CDCl₃, 200 MHz): δ 2.40-2.58 (2H, m), 2.60 (3H, s), 2.62-2.95 (2H, m), 3.60-3.99 (8H, m), 4.00-4.42 (4H, m), 4.40-4.58 (1H, m), 4.85-5.10 (1H, m) (1H, m), 6.95 (1H, m), 7.10 (1H, m), 7.45 (1H, m).

ESMS m/z 518 (MH⁺, 100%).

Example 122

(S)-{3-[4-(4-cyanomethyl-piperidin-1-yl)-phenyl]-2-oxo-oxazolidin-5-ylmethyl}-azide

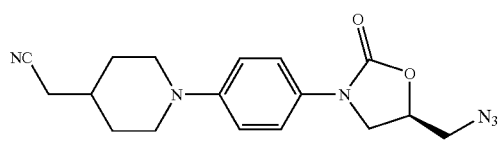

Step-1

Preparation of (R)-{3-[4-(4-cyanomethylidenepiperidin-1-yl)-phenyl]-2-oxo-oxazolidin-5-ylmethyl}-alcohol The compound was prepared as per procedure described in Example 1 by using (R)-{3-[4-(4-oxo-piperidin-1-yl)-phenyl]-2-oxo-oxazolidin-5-ylmethyl}-methanesulphonate in 87% yield.

Step-2

Preparation of (R)-{3-[4-(4-cyanomethypiperidin-1-yl)-phenyl]-2-oxo-oxazolidin-5-ylmethyl}-alcohol The suspension of (R)-{3-[4-(4-cyanomethylidenepiperidin-1-yl)-phenyl]-2-oxo-oxazolidin-5-ylmethyl}-alcohol (0.11 mmol), 10% palladium on carbon (0.1 g) tetrahydrofuran was stirred under atmospheric hydrogen pressure at 30° C. for overnight.

The suspension was filtered and the filtrate was concentrated to the dryness. The residue obtained was chromatographed on the silica gel to provide desired compound in 94% yield.

Step-3

The title compound was prepared as per procedure described in Preparation-6 followed by Preparation-7 by using (R)-{3-[4-(4-cyanomethypiperidin-1-yl)-phenyl]-2-oxo-oxazolidin-5-ylmethyl}-alcohol in 68% yield.

M.P. 85-86° C. and MS (M+1)=341 (MH⁺, 100%), M.F.=$C_{17}H_{20}F_2N_6O_2$.

Example 123

(S)-1-{3-[4-(4-cyanomethyl-piperidin-1-yl)-phenyl]-2-oxo-oxazolidin-5-ylmethyl}-4-carboethoxy-1,2,3-triazole

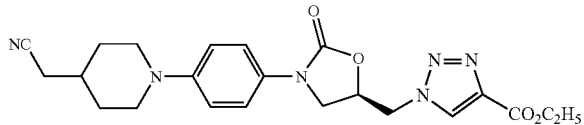

The suspension of (S)-1-{3-[4-(4-cyanomethylidene-piperidin-1-yl)-phenyl]-2-oxo-oxazolidin-5-ylmethyl}-4-carboethoxy-1,2,3-triazole (0.14 mmol), 10% palladium on carbon (0.1 g) tetrahydrofuran was stirred under atmospheric hydrogen pressure at 30° C. for overnight.

The suspension was filtered and the filtrate was concentrated to the dryness. The residue obtained was chromatographed on the silica gel to provide desired compound in 42% yield.

M.P. 198-200° C. and MS (M+1)=439 (MH⁺, 100%), M.F.=$C_{22}H_{26}N_6O_4$.

Example 124

(R)-{3-[4-(4-cyanomethyl-piperidin-1-yl)-phenyl]-2-oxo-oxazolidin-5-ylmethyl}-alcohol

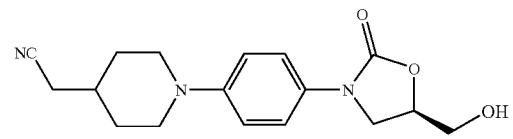

The preparation of the title compound is mentioned in Example 122.

M.P. 110-112° C. and MS (M+1)=316 (MH⁺, 100%), M.F.=$C_{17}H_{21}N_3O_3$.

Example 125

(R)-{3-[4-(4-cyanomethyl-piperidin-1-yl)-phenyl]-2-oxo-oxazolidin-5-ylmethyl}-methanesulphonate;

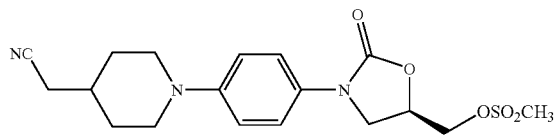

The preparation of the title compound is mentioned in Example-122.

M.P. 114-116° C. and MS (M+1)=394 (MH⁺, 100%), M.F.=$C_{18}H_{23}N_3O_5S$.

Example 126

(S)-N-{3-[4-(4-cyanomethyl-piperidin-1-yl)-phenyl]-2-oxo-oxazolidin-5-ylmethyl}-thioacetamide

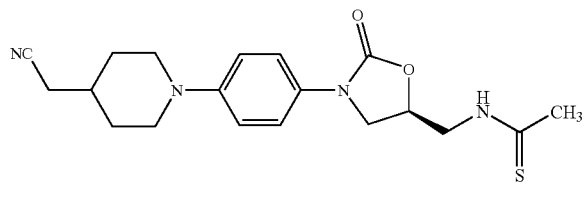

The title compound was prepared as per procedure described in Example 45 by using (S)-N-{3-[4-(4-cyanomethyl-piperidin-1-yl)-phenyl]-2-oxo-oxazolidin-5-ylmethyl}-acetamide in 65% yield.

MS (M+1)=373 (MH$^+$, 100%), M.F.=$C_{19}H_{24}N_4O_2S$.

Example 127

(S)-1-{3-[4-(4-cyanomethyl-piperidin-1-yl)-3-fluorophenyl]-2-oxo-oxazolidin-5-ylmethyl}-4-carboxamido-1,2,3-triazole

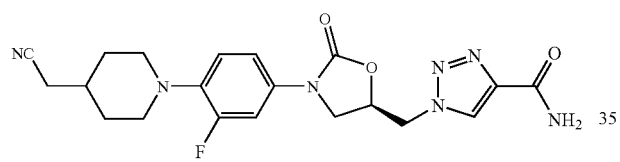

The title compound was prepared as per procedure described in Example-123 by using (S)-1-{3-[4-(4-cyanomethylidene-piperidin-1-yl)-3-fluorophenyl]-2-oxo-oxazolidin-5-ylmethyl}-4-carboxamido-1,2,3-triazole in 42% yield.

M.P. 248-250° C. and MS (M+1)=428 (MH$^+$, 100%), M.F.=$C_{20}H_{22}FN_7O_3$.

Example 128

(S)-1-{3-[4-(4-cyanomethyl-piperidin-1-yl)-3-fluorophenyl]-2-oxo-oxazolidin-5-ylmethyl}-4-cyano-1,2,3-triazole

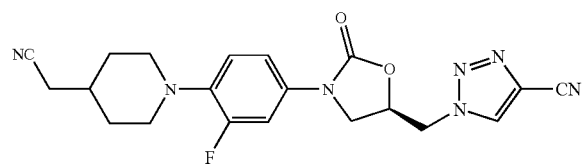

The title compound was prepared as per procedure described in Example-123 by using (S)-1-{3-[4-(4-cyanomethylidene-piperidin-1-yl)-3-fluorophenyl]-2-oxo-oxazolidin-5-ylmethyl}-4-cyano-1,2,3-triazole in 42% yield.

M.P. 200-202° C. and MS (M+1)=410 (MH$^+$, 100%), M.F.=$C_{20}H_{20}FN_7O_2$.

Example 129

(S)-N-{3-[4-(4-cyanomethyl-piperidin-1-yl)-3-fluorophenyl]-2-oxo-oxazolidin-5-ylmethyl}-thioacetamide

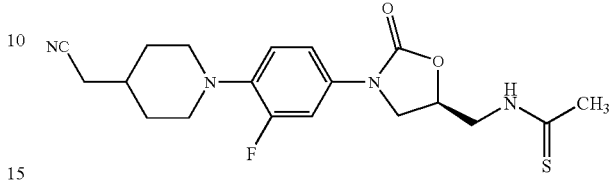

The title compound was prepared as per procedure described in Example-45 by using (S)-1-{3-[4-(4-cyanomethylidene-piperidin-1-yl)-3-fluorophenyl]-2-oxo-oxazolidin-5-ylmethyl}-acetamide in 87% yield.

Mp. 195-197° C.

$^1$H-NMR (CDCl$_3$, 200 MHz): δ 1.50-1.82 (2H, m), 1.85-2.00 (2H, m), 2.40-2.50 (2H, m), 2.59-2.81 (5H, m), 3.30-3.49 (2H, m), 3.75-3.90 (1H, m), 4.00-4.39 (3H, m), 4.90-5.10 (1H, m), 6.90-7.10 (2H, m), 7.41 (1H, m), 8.19-8.38 (1H, m)

ESMS m/z 391(MH$^+$, 100%).

Example 130

(S)-N-{3-[4-(4-cyanomethyl-3-fluoropiperidin-1-yl)-phenyl]-2-oxo-oxazolidin-5-ylmethyl}-thioacetamide

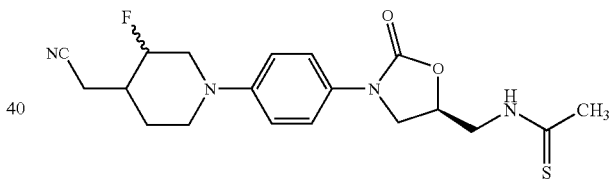

The title compound was prepared as per procedure described in Example-123 by using (S)-1-{3-[4-(4-cyanomethylidene-3-fluoropiperidin-1-yl)-phenyl]-2-oxo-oxazolidin-5-ylmethyl}-acetamide in 56% yield.

MS (M+1)=331 (MH$^+$, 100%), M.F.=$C_{19}H_{23}FN_4O_2S$.

Example 131

(R)-{3-[4-(4-cyanomethyl-3-fluoropiperidin-1-yl)-phenyl]-2-oxo-oxazolidin-5-ylmethyl}-alcohol The title compound was prepared as per procedure described in Example-123 by using (S)-1-{3-[4-(4-cyanomethylidene-piperidin-1-yl)-3-fluorophenyl]-2-oxo-oxazolidin-5-ylmethyl}-alcohol in 89% yield.

MS (M+1)=334 (MH$^+$, 100%), M.F.=$C_{17}H_{20}FN_3O_3$.

Example 132

(R)-{3-[4-(4-cyanomethyl-3-fluoropiperidin-1-yl)-phenyl]-2-oxo-oxazolidin-5-ylmethyl}-methanesulphonate

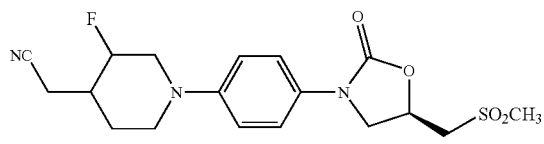

The title compound was prepared as per procedure described in Preparation-6 by using (R)-{3-[4-(4-cyanomethyl-3-fluoropiperidin-1-yl)-phenyl]-2-oxo-oxazolidin-5-ylmethyl}-alcohol in 78% yield.

M.P. 146-148° C. and MS (M+1)=449 (MH$^+$, 100%), M.F.=C$_{22}$H$_{26}$F$_2$N$_4$O$_4$.

Example 133

(S)-N-{3-[4-(4-(1-cyano-1-benzyl)-methylpiperidin-1-yl)-3-fluorophenyl]-2-oxo-oxazolidin-5-ylmethyl}-acetamide

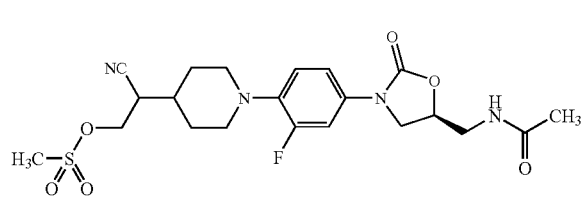

The title compound was prepared as per procedure described in Example 123 by using (S)-N-{3-[4-(4-(1-cyano-1-benzyl)-methylidenepiperidin-1-yl)-3-fluorophenylj-2-oxo-oxazolidin-5-ylmethyl}-acetamide in 76% yield.

Mp. 210-211° C.

$^1$H-NMR (CDCl$_3$, 200 MHz): δ 1.45-1.95 (3H, m), 2.01 (3H, s), 2.55-2.80 (3H, m), 2.90-3.00 (2H, m), 3.40-3.59 (2H, m), 3.60-3.80 (3H, m), 3.90-4.10 (1H, m) 4.70-4.85 (1H, m), 5.90 (1H, m), 6.90 (1H, m), 7.05 (1H, m), 7.20-7.39 (6H, m), 7.41 (1H, m).

ESMS m/z 465 (MH$^+$, 100%).

Example 134

(S)-N-{3-[4-(4-(1-cyano-2-methanesulphonyloxy)-ethylpiperidin-1-yl)-3-fluorophenyl]-2-oxo-oxazolidin-5-ylmethyl}-acetamide

Step-1

Preparation of (S)-N-{3-[4-(4-(1-cyano-2-hydroxy-ethyl)-piperidin-1-yl)-3-fluorophenyl]-2-oxo-oxazolidin-5-ylmethyl}-acetamide.

The mixture of sodium borohydride (5.26 mmol), (S)-N-{3-[4-(4-(1-cyano-1-ethoxycarbonyl-methylidene)-piperidin-1-yl)-3-fluorophenyl]-2-oxo-oxazolidin-5-ylmethyl}-acetamide (0.34 mmol) in methanol (15 ml) was stirred for 0.5 hours at room temperature. The reaction mixture was neutralized with dilute hydrochloric acid. The solid was filtered and purified on silica gel column chromatography recrystallized from chloroform:methanol to provide tile compound in 76% yield.

Step-2

The title compound was prepared as per procedure described in Preparation-6 by using (S)-N-{3-[4-(4-(1-cyano-2-hydroxy-ethyl)-piperidin-1-yl)-3-fluorophenyl]-2-oxo-oxazolidin-5-ylmethyl}-acetamide in 89% yield.

M.P. 136-138° C. and MS (M+1)=483 (MH$^+$, 100%), M.F.=C$_{21}$H$_{27}$FN$_4$O$_6$S.

Example 135

(S)-N-{3-[4-(4-(1-cyano-1-(3,4-difluorophenyl))-methyl)-piperidin-1-yl)-3-fluorophenyl]2-oxo-oxazolidin-5-ylmethyl}-acetamide

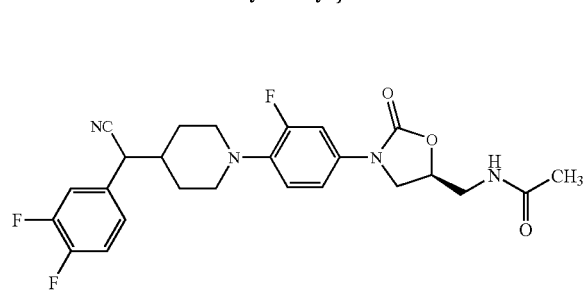

The title compound was prepared as per procedure described in Example 123 by using (S)-N-{3-[4-(4-(1-cyano-1-(3,4-difluorophenyl))-methylidene)-piperidin-1-yl)-3-fluorophenyl]-2-oxo-oxazolidin-5-ylmethyl}-acetamide in 88% yield.

MS (M+1)=487 (MH$^+$, 100%), M.F.=C$_{25}$H$_{25}$F$_3$N$_4$O$_3$.

Example 136

(S)-N-{3-[4-(4-(1-cyano-1-(imidazol-1-yl))-methylpiperidin-1-yl)-3-fluorophenyl]-2-oxo-oxazolidin-5-ylmethyl}-acetamide

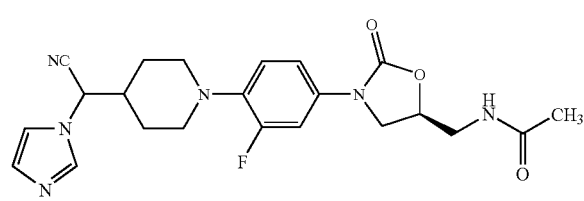

The title product was prepared as per procedure described in Example 123 by using (S)-N-{3-[4-(4-(1-cyano-1-(imidazol-1-yl)-methylidene)-piperidin-1-yl)-3-fluorophenyl]-2-oxo-oxazolidin-5-ylmethyl}-acetamide in 80% yield.

M.P. 210-212° C. and MS (M+1)=441 (MH⁺, 100%), M.F.=$C_{22}H_{25}FN_6O_3$.

Example 137

(S)-N-{3-[4-(4-(1-cyano-1-(thiophen-2-yl))-methylpiperidin-1-yl)-3-luorophenyl]-2-oxo-oxazolidin-5-ylmethyl}-acetamide

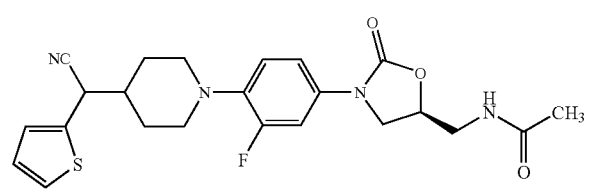

The title product was prepared as per procedure described in Example 123 by using (S)-N-{3-[4-(4-(1-cyano-1-(thiophen-2-yl))-methylidenepiperidin-1-yl)-3-fluorophenyl]-2-oxo-oxazolidin-5-ylmethyl}-acetamide in 92% yield.

Mp. 91-94° C.

¹H-NMR (CDCl₃, 200 MHz): δ 0.80-1.05 (2H, m), 1.58-1.82 (2H, m), 1.85-2.05 (1H, m), 2.10 (3H, s), 2.50-2.79 (2H, m), 3.39-3.60 (2H, m), 3.60-3.81 (3H, m), 3.90-4.10 (2H, m), 4.65-4.81 (1H, m), 6.10 (1H, t), 6.81-7.15 (4H, m), 721-7.45 (2H, m).

ESMS m/z 457 (MH⁺, 100%).

Example 138

(S)-N-{13-[4-(4-(1-cyano-1-(pyridin-2-yl))-methylpiperidin-1-yl)-3-fluorophenyl]-2-oxazolidin-5-ylmethyl}-acetamide;

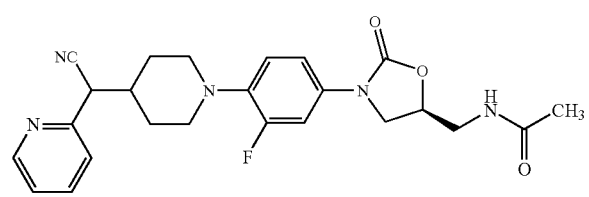

The title product was prepared as per procedure described in Example 123 by using (S)-N-{3-[4-(4-(1-cyano-1-(pyridin-2-yl))-methylidenepiperidin-1-yl)-3-fluorophenyl]-2-oxo-oxazolidin-5-ylmethyl}-acetamide in 78% yield.

Mp. 160-162° C.

¹H-NMR (CDCl₃, 200 MHz): δ 1.61-1.91 (3H, m), 2.01 (3H, s), 2.60-2.80 (2H, m), 3.30-3.50 (4H, m), 3.55-3.80 (3H, m), 3.90-4.10 (2H, m), 4.70-4.85 (1H, m), 6.15 (1H, t), 6.95-7.19 (2H, m), 7.21-7.39 (1H, m), 7.39-7.49 (2H, m) 7.70-7.85 (1H, m), 8.60 (1H, m).

ESMS m/z 452 (MH⁺, 100%).

Example 139

(S)-N-{3-[4-(4-(1-cyano-1-carboxamido)-methylpiperidin-1-yl)-3-fluorophenyl]-2-oxo-oxazolidin-5-ylmethyl}-acetamide

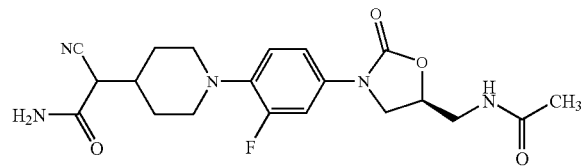

The title product was prepared as per procedure described in Example 123 by using (S)-N-{3-[4-(4-(1-cyano-1-carboxamido)-methylidenepiperidin-1-yl)-3-fluorophenyl]-2-oxo-oxazolidin-5-ylmethyl}-acetamide in 89% yield.

Mp. 180-182° C.

ESMS m/z 418 (MH⁺, 100%).

Example 140

(S)-N-{3-[4-(4-(1-Cyano-1-cyclohexylaminocarbonyl)-methylpiperidin-1-yl)-3-fluorophenyl]-2-oxo-oxazolidin-5-ylmethyl}-acetamide

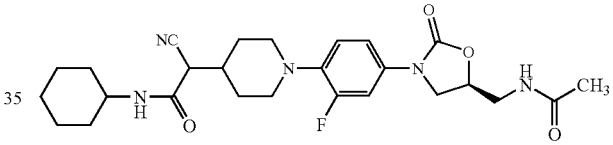

The title product was prepared as per procedure described in Example 123 by using (S)-N-{3-[4-(4-(1-cyano-1-cyclohexylaminocarbonyl)-methylidenepiperidin-1-yl)-3-fluorophenyl]-2-oxo-oxazolidin-5-ylmethyl}-acetamide in 90% yield.

Mp: 210-213° C.

¹H-NMR (CDCl₃, 200 MHz): δ 1.10-155 (m, 6H), 1.62-1.83 (5H, m), 1.85-2.00 (2H, m), 2.05 (3H, s), 2.19-2.40 (1H, m), 2.60-2.80 (2H, m), 3.25-3.59 )4H, m), 3.61-3.85 (3H, m), 3.90-4.10 (1H, m), 4.65-4.82 (1H, m), 5.92-6.19 (2H, m), 6.95 (1H, m), 7.10 (1H, m), 7.49 (1H, m)

ESMS m/z 500 (MH⁺, 100%).

Example 141

(S)-N-{3-[4-(4-(1-cyano-1-(pyrrolidin-1-yl-carbonyl))-methylpiperidin-1-yl)-3-fluorophenyl]-2-oxo-oxazolidin-5-ylmethyl}-acetamide

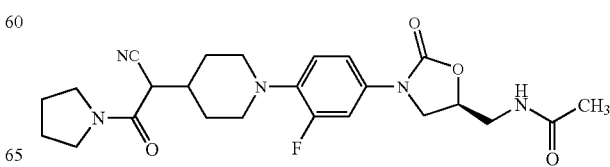

The title product was prepared as per procedure described in Example 123 by using (S)-N-{3-[4-(4-(1-cyano-1-(pyrrolidin-1-yl-carbonyl))-methylidenepiperidin-1-yl)-3-fluorophenyl]-2-oxo-oxazolidin-5-ylmethyl}-acetamide in 78% yield.

Mp: 100-102° C.

ESMS m/z 472 (MH+, 100%).

Example 142

(S)-N-{3-[4-(4-(1-cyano-1-(morpholin-1-yl-carbonyl))-methylpiperidin-1-yl)-3-fluorophenyl]-2-oxo-oxazolidin-5-ylmethyl}-acetamide

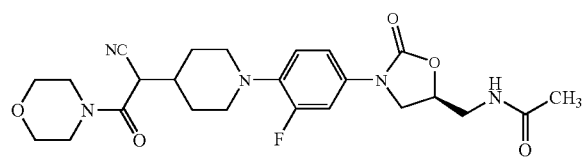

The title product was prepared as per procedure described in Example 123 by using (S)-N-{3-[4-(4-(1-cyano-1-(morpholin-1-yl-carbonyl))-methylidenepiperidin-1-yl)-3-fluorophenyl]-2-oxo-oxazolidin-5-ylmethyl}-acetamide in 79% yield.

Mp. 240-241° C.

$^1$H-NMR (CDCl$_3$, 200 MHz): δ 2.00 (31H, s), 2.10-2.35 (2H, m), 2.55-2.81 (2H, m), 3.25-3.85 (15H, m), 3.95-4.10 (1H, m), 4.62-4.83 (1H, m), 6.20-640 (1H, m), 6.90 (1H, m), 7.05 (1H, m), 7.41 (1H, m)

ESMS m/z 488 (MH+, 100%).

Example 143

(S)-N-{3-[4-(4-(1-cyano-1-ethoxycarbonyl)-methylpiperidin-1-yl)-3-fluorophenyl]-2-oxo-oxazolidin-5-ylmethyl}-acetamide

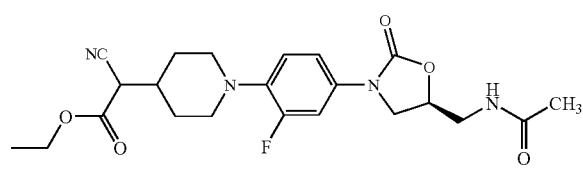

The title product was prepared as per procedure described in Example 123 by using (S)-N-{3-[4-(4-(1-cyano-1-ethoxycarbonyl)-methylienepiperidin-1-yl)-3-fluorophenyl]-2-oxo-oxazolidin-5-ylmethyl}-acetamide in 70% yield.

Mp. 98-100° C.

$^1$H-NMR (CDCl$_3$, 200 MHz): δ 1.30 (3H, t), 1.75-1.95 (2H, m), 2.10 (3H, s), 2.15-2.20 (1H, m), 2.60-2.81 (2H, m), 3.35-3.59 (4H, m), 3.60-3.80 (3H, m), 3.90-4.10 (1H, m), 4.30 (2H, q), 4.70-4.85 (1H, m), 6.10 (1H, t), 6.90 (1H, m), 7.05 (1H, m), 7.41 (1H, m)

ESMS m/z 447 (MH+, 100%).

Example 144

(S)-N-{3-4-(4-(1-cyano-1-(phenylmercapto))-methylpiperidin-1-yl)-3-fluorophenyl]2-oxo-oxazolidin-5-ylmethyl}-acetamide

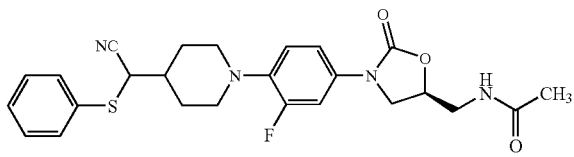

The title product was prepared as per procedure described in Example 123 by using (S)-N-{3-[4-(4-(1-cyano-1-(phenylmercapto))-methylidenepiperidin-1-yl)-3-fluorophenyl]-2-oxo-oxazolidin-5-ylmethyl}-acetamide in 78% yield.

Mp. 148-150° C.

$^1$H-NMR (CDCl$_3$, 200 MHz): δ 1.61-1.90 (2H, m), 2.00 (3H, s), 2.05-2.25 (2H, m), 2.60-2.79 (2H, m), 3.40-3.59 (2H, m), 3.60-3.81 (3H, m), 3.91-4.10 (1H, m), 4.70-4.90 (1H, m), 6.25 (1H, t), 6.95 (1H, dd), 7.10 (1H, m), 7.35-7.45 (4H, m), 7.59-7.65 (2H, m).

ESMS m/z 483 (MH+, 100%).

Example 145

(S)-N-{3-[4-(4-(1-cyano-1-(pyridin-2-yl))-methylpiperidin-1-yl)-3-fluorophenyl]-2oxo-oxazolidin-5-ylmethyl}-thioacetamide

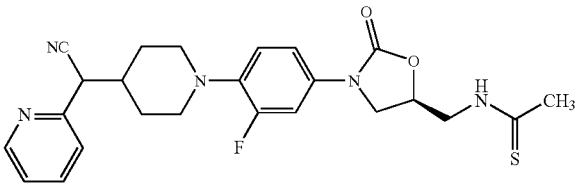

The title product was prepared as per procedure described in Example 45 by using (S)-N-{3-[4-(4-(1-cyano-1-(pyridin-2-yl))-methylpiperidin-1-yl)-3-fluorophenyl]-2-oxo-oxazolidin-5-ylmethyl}-acetamide in 77% yield.

Mp. 102-103° C.

$^1$H-NMR (CDCl$_3$, 200 MHz): δ 1.60-1.95 (3H, m), 2.01-2.30 (2H, m), 2.40 (3H, s), 3.20-3.90 (6H, m), 3.95-4.39 (3H, m), 4.81-5.10 (1H, m), 5.20-5.40 (1H, m), 6.70-7.10 (2H, m), 7.20-7.49 (2H, m), 7.65-8.10 (2H, m), 8.20-8.40 (1H, m), 860-8.80 (1H, m).

ESMS m/z 468 (MH+, 100%).

Example 146

(S)-N-{3-[4-(4-(1-cyano-1-(morpholin-1-yl-carbonyl))-methylpiperidin-1-yl)-3-fluorophenyl]-2-oxo-oxazolidin-5-ylmethyl}-thioacetamide

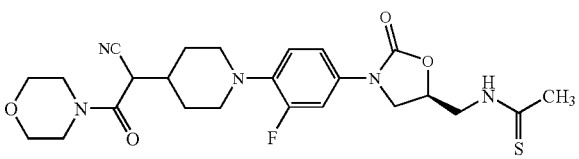

The title product was prepared as per procedure described in Example 45 by using (S)-N-{3-[4-(4-(1-cyano-1-(morpholin-1-yl-carbonyl))-methylpiperidin-1-yl)-3-fluorophenyl]-2-oxo-oxazolidin-5-ylmethyl}-acetamide in 75% yield.
Mp. 220-222° C.
ESMS m/z 504 (MH⁺, 100%).

Example 147

(S)-N-{3-[4-(4-(1-cyano-1-ethoxycarbonyl)-methylpiperidin-1-yl)-3-fluorophenyl]-2-oxo-oxazolidin-5-ylmethyl}-thioacetamide

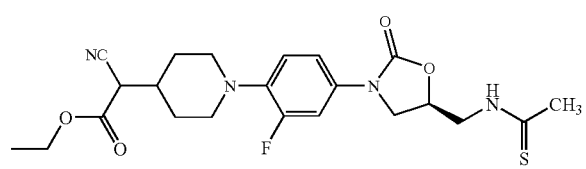

The title product was prepared as per procedure described in Example 45 by using (S)-N-{3-[4-(4-(1-cyano-1-ethoxycarbonyl)-methylpiperidin-1-yl)-3-fluorophenyl]-2-oxo-oxazolidin-5-ylmethyl}-thioacetamide in 82% yield.
Mp. 93-95° C.
ESMS m/z 463 (MH⁺, 100%).

Example 148

(S)-N-{3-[4-(4-(1-cyano-1-carboxamido)-methylpiperidin-1-yl)-3-fluorophenyl]-2-oxo-oxazolidin-5-ylmethyl}-thioacetamide

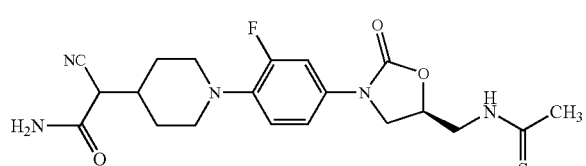

The title product was prepared as per procedure described in Example 45 by using (S)-N-{3-[4-(4-(1-cyano-1-carboxamido)-methylpiperidin-1-yl)-3-fluorophenyl]-2-oxo-oxazolidin-5-ylmethyl}-acetamide in 68% yield.
MS (M+1)=434 (MH⁺, 100%), M.F.=$C_{20}H_{24}FN_5O_3S$.

Example 149

(S)-N-{3-[4-(4-(1-cyano-1-thiocarboxamido)-methylpiperidin-1-yl)-3-fluorophenyl]-2-oxo-oxazolidin-5-ylmethyl}-thioacetamide

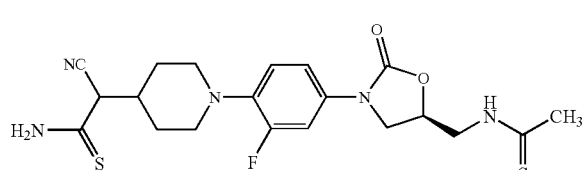

The title product was prepared as per procedure described in Example 121 by using (S)-N-{3-[4-(4-(1-cyano-1-carboxamido)-methylpiperidin-1-yl)-3-fluorophenyl]2-oxo-oxazolidin-5-ylmethyl}-acetamide in 38% yield.
Mp. 178-180° C.
ESMS m/z 449(MH⁺, 100%).

Example 150

(S)-1-{3-[4-(4-(1-cyano-2-hydroxy)-ethylpiperidin-1-yl)-3-fluorophenyl]-2-oxo-oxazolidin-5-ylmethyl}-4-methoxycarbonyl-1,2,3-triazole

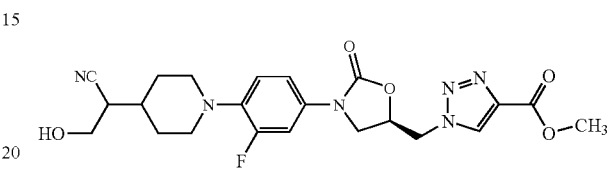

Step-1

Preparation of (S)-N-{3-[4-(4-(1-cyano-2-hydroxy-ethyl)-piperidin-1-yl)-3-fluorophenyl]-2-oxo-oxazolidin-5-ylmethyl}-azide.

The compound was prepared by using the procedure described in Example-134 from (S)-N-{3-[4-(4-(1-cyano-1-ethoxycarbonyl-methylidene)-piperidin-1-yl)-3-fluorophenyl]-2-oxo-oxazolidin-5-ylmethyl}-alcohol.

This compound was converted to the desired compound by using procedures of Preparation-6 followed by Preparation-7 in overall 64% yield.

Step-2

The title product was prepared as per procedure described in Example 4 by using (S)-N-{3-[4-(4-(1-cyano-2-hydroxy-ethyl)-piperidin-1-yl)-3-fluorophenyl]-2oxo-oxazolidin-5-ylmethyl}-azide and methyl propiolate in the place of ethyl propiolate in 68% yield.
M.P. 204-206° C. and MS (M+1)=474 (MH⁺, 100%), M.F.=$C_{22}H_{25}FN_6O_5$.

Example 151

(S)-1-{3-[4-(4-(1-cyano-2-hydroxy)-ethylpiperidin-1-yl)-3-fluorophenyl]-2-oxo-oxazolidin-5-ylmethyl}-4-ethoxycarbonyl-1,2,3-triazole

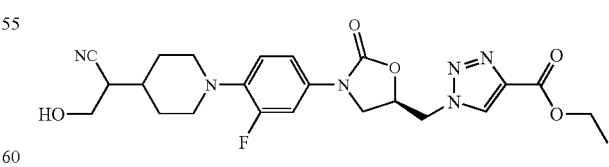

The isomeric mixture was prepared as per procedure described in Example 4 by using (S)-N-{3-[4-(4-(1-cyano-2-hydroxy-ethyl)-piperidin-1-yl)-3-fluorophenyl]-2-oxo-oxazolidin-5-ylmethyl}-azide in 59% yield as a isomeric mixture. The title compound isomer was separated on preparative HPLC in 44% yield.

M.P. 170-172° C. and MS (M+1)=487 (MH+, 100%), M.F.=$C_{23}H_{27}FN_6O_5$.

Example 152

(S)-1-{3-[4-(4-(1-cyano-2-hydroxy)-ethylpiperidin-1-yl)-3-fluorophenyl]-2-oxo-oxazolidin-5-ylmethyl}-5-ethoxycarbonyl-1,2,3-triazole

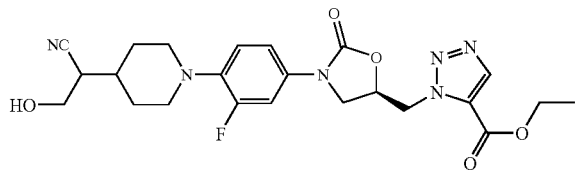

The other isomer obtained in Example 151 was separated by using preparative HPLC in 12% yield.
M.P. 76-78° C. and MS (M+1)=487 (MH+, 100%), M.F.=$C_{23}H_{27}FN_6O_5$.

Example 153

(R)-3-{3-[4-(4-(1-cyano-2-hydroxy)-ethylpiperidin-1-yl)-3-fluorophenyl]-2-oxo-oxazolidin-5-ylmethyloxy}-iso-oxazole

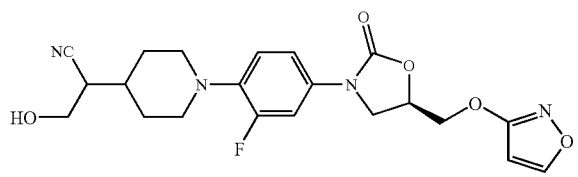

The title product was prepared as per procedure described in Example 83 by using (S)-N-{3-[4-(4-(1-cyano-2-hydroxy-ethyl)-piperidin-1-yl)-3-fluorophenyl]-2-oxo-oxazolidin-5-ylmethyl}-alcohol in 67% yield.
M.P. 146-148° C. and MS (M+1)=431 (MH+, 100%), M.F.=$C_{21}H_{23}FN_4O_5$.

Example 154

(R)-{3-[4-(4-(1-cyano-2-hydroxy)-ethylpiperidin-1-yl)-3-fluorophenyl]-2-oxo-oxazolidin-5-ylmethyl}-methanesulphonate

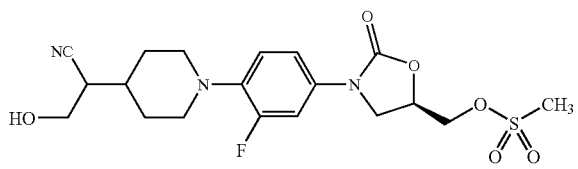

The title compound was prepared by using the procedure described in Preparation-6 from (S)-N-{3-[4-(4-(1-cyano-2-hydroxy-ethyl)-piperidin-1-yl)-3-fluorophenyl]-2-oxo-oxazolidin-5-ylmethyl}-alcohol in overall 74% yield.
M.P. 144-146° C. and MS (M+1)=442 (MH+, 100%), M.F.=$C_{19}H_{24}FN_3O_6S$.

Example 155

(R)-{3-[4-(4-(1-Cyano-1-hydroxycarbonyl)-methylpiperidin-1-yl)-3-fluorophenyl]-2-oxo-oxazolidin-5-ylmethyl}-methanesulphonate

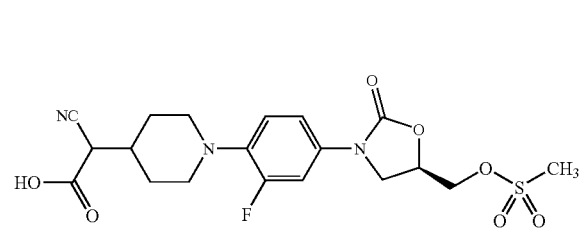

The title compound was prepared by using the procedure described in Preparation-6 from (S)-N-{3-[4-(4-(1-cyano-1-hydroxycarbonyl)-methylpiperidin-1-yl)-3-fluorophenyl]-2-oxo-oxazolidin-5-ylmethyl}-alcohol in overall 80% yield.
M.P. 108-110° C. and MS (M+1)=456 (MH+, 100%), M.F.=$C_{19}H_{22}FN_3O_7S$.

Example 156

(R)-{3-[4-(4-(1-cyano-1-ethoxycarbonyl)-methylpiperidin-1-yl)-3-fluorophenyl]-2-oxo-oxazolidin-5-ylmethyl}-methanesulphonate

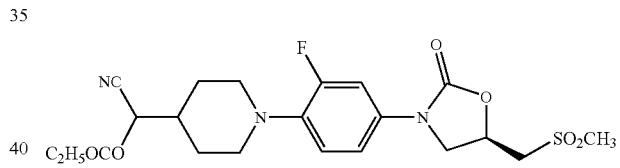

The title compound was prepared by using the procedure described in Preparation-6 from (S)-N-{3-[4-(4-(1-cyano-1-ethoxycarbonyl)-methylpiperidin-1-yl)-3-fluorophenyl]-2-oxo-oxazolidin-5-ylmethyl}-alcohol in overall 85% yield.
M.P. 102-104° C. and MS (M+1)=484 (MH+, 100%), M.F.=$C_{21}H_{26}FN_3O_7S$.

Example 157

(R)-{3-[4-(4-(1-cyano-1-(1,3-thiazol-2-yl))-methylpiperidin-1-yl)-3-fluorophenyl]-2-oxo-oxazolidin-5-ylmethyl}-methanesulphonate

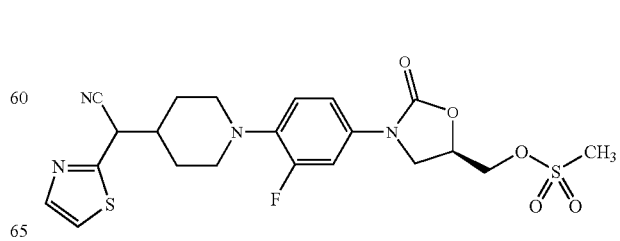

step-1

Preparation of (S)-N-{3-[4-(4-(1-cyano-1-(1,3-thiazol-2-yl))-methylidenepiperidin-1-yl)-3-fluorophenyl]-2-oxo-oxazolidin-5-ylmethyl}-alcohol The desired compound was prepared by following the procedure described in Example 94 and using (1,3-thiathiazol-2-yl)-acetonitrile in the place of cyclopropylacetonitrile in 66% yield.

Step-2

Preparation of (S)-N-{3-[4-(4-(1-cyano-1-(1,3-thiazol-2-yl))-methylpiperidin-1-yl)-3-fluorophenyl]-2-oxo-oxazolidin-5-ylmethyl}-alcohol The desired compound was prepared by following the procedure described in Example 122 and using (S)-N-{3-[4-(4-(1-cyano-1-(1,3-thiazol-2-yl))-methylidenepiperidin-1-yl)-3-fluorophenyl]-2-oxo-oxazolidin-5-ylmethyl}-alcohol in 63% yield.

Step-3

The title compound was prepared by using the procedure described in Preparation-6 from (S)-N-{3-[4-(4-(1-cyano-1-(1,3-thiazol-2-yl))-methylpiperidin-1-yl)-3-fluorophenyl]-2-oxo-oxazolidin-5-ylmethyl}-alcohol in 66% yield.

M.P. 64-66° C. and MS (M+1)=495 (MH$^+$, 100%), M.F.=$C_{21}H_{23}FN_4O_5S_2$.

Example 158

(R)-{3-[4-(4-(1-cyano-1-carboxamido)-methylpiperidin-1-yl)-3-fluorophenyl]-2-oxo-oxazolidin-5-ylmethyl}-methanesulphonate

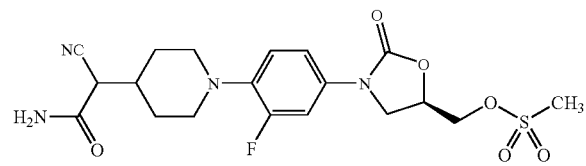

The title compound was prepared by using the procedure described in Preparation-6 from (S)-N-{3-[4-(4-(1-cyano-1-carboxamide)-methylpiperidin-1-yl)-3-fluorophenyl]-2-oxo-oxazolidin-5-ylmethyl}-alcohol in 80% yield.

M.P. 220-222° C. and MS (M+1)=455 (MH$^+$, 100%), M.F.=$C_{19}H_{23}FN_4O_6S$.

Example 159

(S)-N-{3-[4-(4-cyanomethyl-3,4-dehydropiperidin-1-yl)-3-fluorophenyl]-2-oxo-oxazolidin-5-ylmethyl}-acetamide

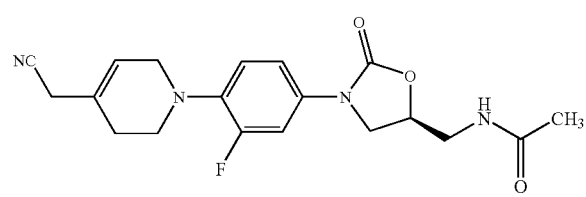

A mixture of (S)-N-{3-[4-(4-oxo-piperidin-1-yl)-3-fluorophenyl]-2-oxo-oxazolidin-5-ylmethyl}-acetamide (28.64 mmol), pyridine (6.32 mmol), cyanoacetic acid (30.00 mmol) and ammonium acetate (6.40 mmol) in toluene was refluxed with azeotropic removal of water for 5 to 6 hours. The reaction mixture was cooled at room temperature, diluted with ethyl acetate and washed with water. The organic layer was dried and concentrated in vacuo to afford crude product. The crude product was recrystallized from ethyl acetate to give the title compound in 67% yield.

Mp. 132° C. and MS (M+1)=373.

Example 160

(S)-N-{3-[4-(4-cyanomethyl-3,4-dehydropiperidin-1-yl)-3-fluorophenyl]-2-oxo-oxazolidin-5-ylmethyl}-thioacetamide

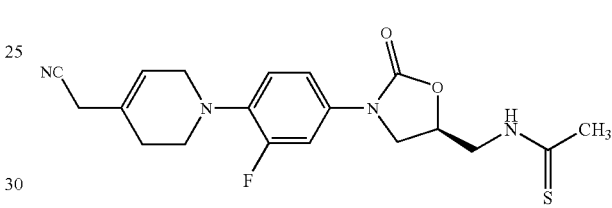

The title compound was prepared as per procedure described in Example-45 and by using (S)-N-{3-[4-(4-cyanomethyl-3,4-dehydropiperidin-1-yl)-3-fluorophenyl]-2-oxo-oxazolidin-5-ylmethyl}-acetamide in 87% yield as a solid.

Mp. 110-112° C. and MS (M+1)=389.

Example 161

(S)-N-{3-[4-(4-cyanomethyl-3-methyl-4,5-dehydropiperidin-1-yl)-3-fluorophenyl]-2-oxo-oxazolidin-5-ylmethyl}-acetamide

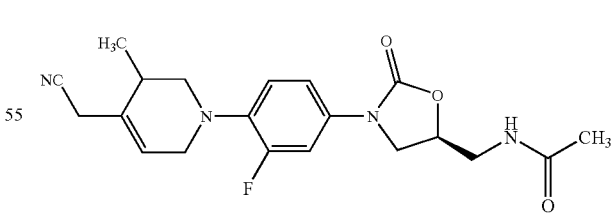

The title compound was prepared as per procedure described in Example-159 and by using (S)-{3-[4-(3-methyl-4-oxo-piperidin-1-yl)-phenyl]-2-oxo-oxazolidin-5-ylmethyl}-acetamide in 65% yield.

M.P. 149-150° C. and MS (M+1)=387 (MH$^+$, 100%), M.F.=$C_{20}H_{23}FN_4O_3$.

Example 162

(S)-N-{3-[4-(4-cyanomethyl-3-fluoro-4,5-dehydropiperidin-1-yl)-3-fluorophenyl]-2-oxo-oxazolidin 5-yl-methl}-acetamide

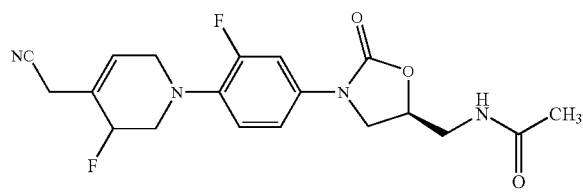

The title compound was prepared as per procedure described in Example 159 and by using (S)-{3-[4-(3-fluoro-4-oxo-piperidin-1-yl)-phenyl]-2-oxo-oxazolidin-5-ylmethyl}-acetamide in 71% yield.

M.P. 128-130° C. and MS (M+1)=391 (MH+, 100%), M.F.=$C_{19}H_{20}F_2N_4O_3$.

Example 163

(S)-N-{3-[4-(4-cyanomethyl-3-fluoro-4,5-dehydropiperidin-1-yl)-3-fluorophenyl]-2-oxo-oxazolidin-5-ylmethyl}-isobutylcarbamate

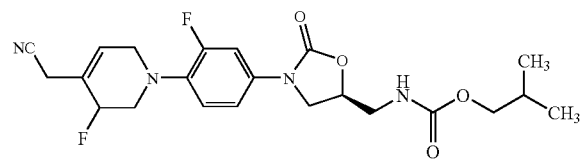

Step-1

Preparation of (S)-N-{3-[4-(4-cyanomethyl-3-fluoro-4,5-dehydropiperidin-1-yl)-3-fluorophenyl]-2-oxo-oxazolidin-5-ylmethyl}-amine.

The title compound was prepared as per procedure described in Example-159 and by using (S)-{3-[4-(3-fluoro-4-oxo-piperidin-1-yl)-phenyl]-2-oxo-oxazolidin-5-ylmethyl}-amine in 48% yield.

Step-2

The title compound was prepared by following the procedure of Example 10 and by using (S)-N-{3-[4-(4-cyanomethyl-3-fluoro-4,5-dehydropiperidin-1-yl)-3-fluorophenyl]-2-oxo-oxazolidin-5-ylmethyl}-amine and isobutylchloroformate in 77% yield.

M.P. 146-148° C. and MS (M+1)=449 (MH+, 100%), M.F.=$C_{22}H_{26}F_2N_4O_4$.

The invention claimed is:

1. A compound of Formula I

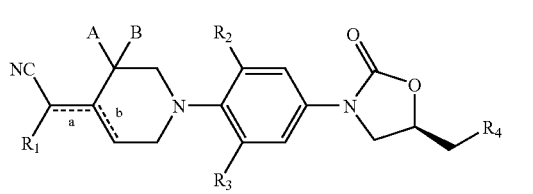

Formula I or pharmaceutical acceptable salts thereof, wherein

"a" represents a single bond or a double bond;

"b" represents a single bond or a double bond; wherein

"a" and "b" cannot both be double bonds at the same time;

"A" and "B" are each and independently selected from H, $C_1$-$C_6$ alkyl, $CO_2Et$, or halogen;

when "a" is a double bond, or "a" is a single bond and "A" is not H, $CH_3$, $CO_2Et$, or F $R_1$ is, H, $C_1$-$C_6$ alkyl, substituted $C_1$-$C_6$ alkyl, alkenyl, alkynyl, cycloalkyl, substituted cycloalkyl, alkanoyl, substituted alkanoyl, aralkanoyl, substituted aralkanoyl, alkoxycarbonyl, substituted alkoxycarbonyl, thioacyl, substituted thioacyl, aroyl, substituted aroyl, alkylmercapto, arylmercapto, aralkyl, aryl, substituted aryl, cyano, carboxylic acid, carboxamido, amino, substituted amino, or halogen;

when "a" is a single bond and "A" is H, $CH_3$,$CO_2Et$, or F, then $R_1$ is alkenyl, alkynyl, cycloalkyl, substituted cycloalkyl, alkanoyl, substituted alkanoyl, aralkanoyl, substituted aralkanoyl, alkoxycarbonyl, substituted alkoxycarbonyl, thioacyl, substituted thioacyl, aroyl, substituted aroyl, alkylmercapto, arylmercapto, aralkyl, aryl, substituted aryl, or carboxamido;

$R_2$ and $R_3$ are the same or different and are hydrogen or halo; and $R_4$ is $OSO_2CH_3$, amino, mono or di substituted amino, azido, CN, NHCN, N(CN)-allyl, NCO, NHCHO, $C_1$-$C_6$ alkyl amido, substituted $C_1$-$C_6$ alkyl amido, $NHCO_2CH_3$, $NHCO_2Et$, $NHCO_2iPr$, $NHCO_2CH_2CH(CH_3)_2$, $NHCOCH_2OCOC(CH_3)_3$, $N(CH_3)COCH_3$, $NHCSCH_3$, $NHCSOCH_3$, $NHCSCH_2OH$, $NHCSNHCH_2CH_2OH$, $NHCSCH_2NH_2$, $NHCONHCH_2CH_2N(CH_3)_2$, $NHCSNH_2$, $NHCSNHCH_3$, $NHSO_2CH_3$, or $NHSO_2$-($_3$-Me-Ph);

wherein the one or more substituents of substituted $C_1$-$C_6$ alkyl are selected from the group consisting of aryl, hydroxy, methanesulphonyloxy, cyano, halo, amino, and substituted amino groups;

wherein the one or more substituents of substituted cycloalkyl are selected from the group consisting of alkyl, hydroxyl, amino, substituted amino, alkoxycarbonyl, carboximido, cyano and halogen groups;

wherein the one or more substituents of substituted alkanoyl are selected from the group consisting of alkyl, hydroxyl, amino, substituted amino, alkoxycarbonyl, carboxamido, cyano and halogen groups;

wherein the one or more substituents of substituted aralkanoyl are selected from the group consisting of alkyl, hydroxyl, amino, substituted amino, alkoxycarbonyl, carboxamido, cyano and halogen groups;

wherein the one or more substituents of substituted alkoxycarbonyl are selected from the group consisting of alkyl, hydroxyl, amino, substituted amino, alkoxycarbonyl, carboxamido, cyano and halogen groups;

wherein the one or more substituents of substituted thioacyl are selected from the group consisting of alkyl, hydroxyl, amino, substituted amino, alkoxycarbonyl, carboxamido, cyano and halogen groups;

wherein the one or more substituents of substituted aroyl are selected from the group consisting of alkyl, hydroxyl, amino, substituted amino, alkoxycarbonyl, carboxamido, cyano and halogen groups;

wherein the one or more substituents of substituted aryl are selected from the group consisting of alkyl, hydroxyl, amino, substituted amino, alkoxycarbonyl, carboxamido, cyano and halogen groups and wherein the one or more substituents of substituted amino group are selected from one or more unsubstituted or substituted $C_1$-$C_3$ alkyl groups.

2. A compound according to claim 1, wherein a subset of compounds is selected from those of Formula II Formula II

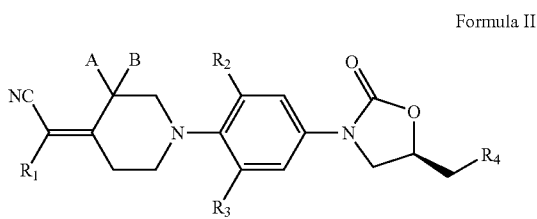

wherein $R_1$, $R_2$, $R_3$, $R_4$, A and B are as defined in claim 1.

3. A compound according to claim 1, wherein a subset of compounds is selected from those of Formula III Formula III

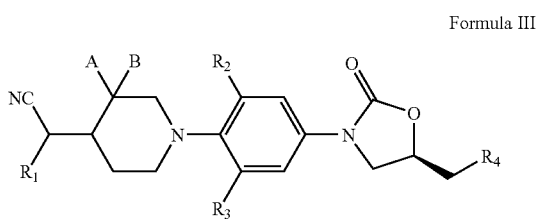

wherein $R_1$, $R_2$, $R_3$, $R_4$, A and B are as defined in claim 1.

4. A compound according to claim 1, wherein a subset of compounds is selected from those of Formula IV Formula IV

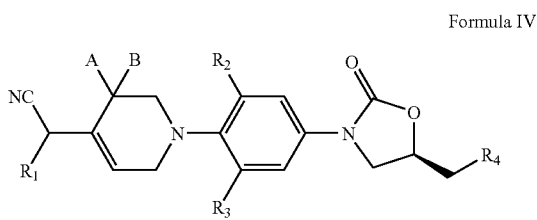

wherein $R_1$, $R_2$, $R_3$, $R_4$, A and B are as defined in claim 1.

5. A compound selected from the group consisting of:
(S)-{3-[4-(4-cyanomethylidene-piperidin-1-yl)-phenyl]-2-oxo-oxazolidin-5-ylmethyl}-azide;
(S)-N-{3-[4-(4-cyanomethylidene-piperidin-1-yl)-phenyl]-2-oxo-oxazolidin-5-ylmethyl}-formamide;
(S)-N-{3-[4-(4-cyanomethylidene-piperidin-1-yl)-phenyl]-2-oxo-oxazolidin-5-ylmethyl}-acetamide;
(R)-{3-[4-(4-cyanomethylidene-piperidin-1-yl)-phenyl]-2-oxo-oxazolidin-5-ylmethyl}-methanesulphonate;
(S)-N-{3-[4-(4-cyanomethylidene-piperidin-1-yl)-3-fluorophenyl]-2-oxo-oxazolidin-5-ylmethyl}-isocynate;
(S)-N-{3-[4-(4-cyanomethylidene-piperidin-1-yl)-3-fluorophenyl]-2-oxo-oxazolidin-5-ylmethyl}-formamide;
(S)-N-{3-[4-(4-cyanomethylidene-piperidin-1-yl)-3-fluorophenyl]-2-oxo-oxazolidin-5-ylmethyl}-acetamide;
(S)-N-{3-[4-(4-cyanomethylidene-piperidin-1-yl)-3-fluorophenyl]-2-oxo-oxazolidin-5-ylmethyl}-propionamide;
(S)-N-{3-[4-(4-cyanomethylidene-piperidin-1-yl)-3-fluorophenyl]-2-oxo-oxazolidin-5-ylmethyl}-2-dimethylpropionamide;
(S)-N-{3-[4-(4-cyanomethylidene-piperidin-1-yl)-3-fluorophenyl]-2-oxo-oxazolidin-5-ylmethyl}-3-dimethylbutanamide;
(S)-N-{3-[4-(4-cyanomethylidene-piperidin-1-yl)-3-fluorophenyl]-2-oxo-oxazolidin-5-ylmethyl}-2-hydroxyacetamide;
(S)-N-{3-[4-(4-cyanomethylidene-piperidin-1-yl)-3-fluorophenyl]-2-oxo-oxazolidin-5-ylmethyl}-2-pivolyloxyacetamide;
(S)-N-{3-[4-(4-cyanomethylidene-piperidin-1-yl)-3-fluorophenyl]-2-oxo-oxazolidin-5-ylmethyl}-N-methylacetamide;
(S)-{3-[4-(4-cyanomethylidene-piperidin-1-yl)-3-fluorophenyl]-2-oxo-oxazolidin-5-ylmethyl}-azide;
(S)-{3-[4-(4-cyanomethylidene-piperidin-1-yl)-3-fluorophenyl]-2-oxo-oxazolidin-5-ylmethyl}-amine;
(S)-{3-[4-(4-cyanomethylidene-piperidin-1-yl)-3-fluorophenyl]-2-oxo-oxazolidin-5-ylmethylamino}-prop-2-ene;
(S)-{3-[4-(4-cyanomethylidene-piperidin-1-yl)-3-fluorophenyl]-2-oxo-oxazolidin-5-ylmethylamino}-nitrile;
(S)-{3-[4-(4-cyanomethylidene-piperidin-1-yl)-3-fluorophenyl]-2-oxo-oxazolidin-5-ylmethylamino}-acetonitrile;
(S)-{3-[4-(4-cyanomethylidene-piperidin-1-yl)-3-fluorophenyl]-2-oxo-oxazolidin-5-ylmethylamino}-methylamine;
(S)-{N-{3-[4-(4-cynomethylidene-piperidin-1-yl)-3-fluorophenyl]-2-oxo-oxazolidin-5-ylmethylamino}N-cyano}-prop-2-ene;
(S)-N-{3-[4-(4-cyanomethylidene-piperidin-1-yl)-3-fluorophenyl]-2-oxo-oxazolidin-5-ylmethyl}-2-cyanoacetamide;
(S)-N-{3-[4-(4-cyanomethylidene-piperidin-1-yl)-3-fluorophenyl]-2-oxo-oxazolidin-5-ylmethyl}-difluoroacetamide;
(S)-N-{3-[4-(4-cyanomethylidene-piperidin-1-yl)-3-fluorophenyl]-2-oxo-oxazolidin-5-ylmethyl}-trifluoroacetamide;
(S)-N-{3-[4-(4-cyanomethylidene-piperidin-1-yl)-3-fluorophenyl]-2-oxo-oxazolidin-5-ylmethyl}-chloroacetamide;
(S)-N-{3-[4-(4-cyanomethylidene-piperidin-1-yl)-3-fluorophenyl]-2-oxo-oxazolidin-5-ylmethyl}-dichloroacetamide;

(S)-N-{3-[4-(4-cyanomethylidene-piperidin-1-yl)-3-fluorophenyl]-2-oxo-oxazolidin-5-ylmethyl}-trichloroacetamide;
(S)-N-{3-[4-(4-cyanomethylidene-piperidin-1-yl)-3-fluorophenyl]-2-oxo-oxazolidin-5-ylmethyl}-bromoacetamide;
(S)-N-{3-[4-(4-cyanomethylidene-piperidin-1-yl)-3-fluorophenyl]-2-oxo-oxazolidin-5-ylmethyl}-dibromoacetamide;
(S)-N-{3-[4-(4-cyanomethylidene-piperidin-1-yl)-3-fluorophenyl]-2-oxo-oxazolidin-5-ylmethyl}-iodoacetamide;
(S)-N-{3-[4-(4-cyanomethylidene-piperidin-1-yl)-3-fluorophenyl]-2-oxo-oxazolidin-5-ylmethyl}-4-methylphenylsulphonamide;
(S)-N-{3-[4-(4-cyanomethylidene-piperidin-1-yl)-3-fluorophenyl]-2-oxo-oxazolidin-5-ylmethyl}-methylcarbamate;
(S)-N-{3-[4-(4-cyanomethylidene-piperidin-1-yl)-3-fluorophenyl]-2-oxo-oxazolidin-5-ylmethyl}-ethylcarbamate;
(S)-N-{3-[4-(4-cyanomethylidene-piperidin-1-yl)-3-fluorophenyl]-2-oxo-oxazolidin-5-ylmethyl}-isopropylcarbamate;
(2S,5S)-{N-{3-[4-(4-cyanomethylidene-piperidin-1-yl)-3-fluorophenyl]-2-oxo-oxazolidin-5-ylmethyl}-propionamid-2-yl}-amine;
(2S,5S)-{N-{3-[4-(4-cyanomethylidene-piperidin-1-yl)-3-fluorophenyl]-2-oxo-oxazolidin-5-ylmethyl}-3-hydroxypropionamid-2-yl}-amine;
(S)-N-{3-[4-(4-cyanomethylidene-piperidin-1-yl)-3-fluorophenyl]-2-oxo-oxazolidin-5-ylmethyl}-thioacetamide;
(S)-N-{3-[4-(4-cyanomethylidene-piperidin-1-yl)-3-fluorophenyl]-2-oxo-oxazolidin-5-ylmethyl}-methylthiocarbamate;
(S)-N-{3-[4-(4-cyanomethylidene-piperidin-1-yl)-3-fluorophenyl]-2-oxo-oxazolidin-5-ylmethyl}-2-hydroxythioacetamide;
(S)-N-{3-[4-(4-cyanomethylidene-piperidin-1-yl)-3-fluorophenyl]-2-oxo-oxazolidin-5-ylmethyl}-2-hydroxyethylthiocarbamide;
(S)-N-{3-[4-(4-cyanomethylidene-piperidin-1-yl)-3-fluorophenyl]-2-oxo-oxazolidin-5-ylmethylamino}-thiocarbonylmethylamine;
(S)-N-{3-[4-(4-cyanomethylidene-piperidin-1-yl)-3-fluorophenyl]-2-oxo-oxazolidin-5-ylmethyl}-2-dimethylaminoethylthiocarbamide;
(S)-N-{3-[4-(4-cyanomethylidene-piperidin-1-yl)-3-fluorophenyl]-2-oxo-oxazolidin-5-ylmethyl}-thiocarbamide;
(S)-N-{3-[4-(4-cyanomethylidene-piperidin-1-yl)-3-fluorophenyl]-2-oxo-oxazolidin-5-ylmethyl}-methylthiocarbamide;
(S)-N-{3-[4-(4-cyanomethylidene-piperidin-1-yl)-3-fluorophenyl]-2-oxo-oxazolidin-5-ylmethyl}-methanesulphonamide;
(R)-{3-[4-(4-cyanomethylidene-piperidin-1-yl)-3-fluorophenyl]-2-oxo-oxazolidin-5-ylmethyl}-methanesulphonate;
(S)-N-{3-[4-(4-cyanomethylidene-3-fluoropiperidin-1-yl)-phenyl]-2-oxo-oxazolidin-5-ylmethyl}-acetamide;
E and Z isomers of (S)-N-{3-[4-(4-cyanomethylidene-3-fluoropiperidin-1-yl)-3-fluorophenyl]-2-oxo-oxazolidin-5-ylmethyl}-acetamide;
(S)-N-{3-[4-(4-cyanomethylidene-3-fluoropiperidin-1-yl)-3-fluorophenyl]-2-oxo-oxazolidin-5-ylmethyl}-difluoroacetamide;
(S)-N-{3-[4-(4-cyanomethylidene-3-fluoropiperidin-1-yl)-3-fluorophenyl]-2-oxo-oxazolidin-5-ylmethyl}-isobutylcarbamate;
(R)-{3-[4-(4-cyanomethylidene-3-fluoropiperidin-1-yl)-3-fluorophenyl]-2-oxo-oxazolidin-5-ylmethyl}-methanesulphonate;
(S)-N-{3-[4-(4-cyanomethylidene-3-fluoropiperidin-1-yl)-3-fluorophenyl]-2-oxo-oxazolidin-5-ylmethyl}-thioacetamide;
(S)-N-{3-[4-(4-cyanomethylidene-3,3-difluoropiperidin-1-yl)-phenyl]-2-oxo-oxazolidin-5-ylmethyl}-acetamide;
(S)-N-{3-[4-(4-cyanomethylidene-3-methylpiperidin-1-yl)-3-fluorophenyl]-2-oxo-oxazolidin-5-ylmethyl}-formamide;
(S)-N-{3-[4-(4-cyanomethylidene-3-methylpiperidin-1-yl)-3-fluorophenyl]-2-oxo-oxazolildin-5-ylmethyl}-acetamide;
(S)-N-{3-[4-(4-cyanomethylidene-3-methylpiperidin-1-yl)-3-fluorophenyl]-2-oxo-oxazolidin-5-ylmethyl}-trifluoroacetamide;
(S)-N-{3-[4-(4-cyanomethylidene-3-methylpiperidin-1-yl)-3-fluorophenyl]-2-oxo-oxazolidin-5-ylmethyl}-2-cyanoacetamide;
(S)-N-{3-[4-(4-cyanomethylidene-3-methylpiperidin-1-yl)-3-fluorophenyl]-2-oxo-oxazolidin-5-ylmethyl}-methylthiocarbamate;
(S)-N-{3-[4-(4-cyanomethylidene-3-methylpiperidin-1-yl)-3-fluorophenyl]-2-oxo-oxazolidin-5-ylmethyl}-thiocarbamide;
(S)-N-{3-[4-(4-cyanomethylidene-3-methylpiperidin-1-yl)-3-fluorophenyl]-2-oxo-oxazolidin-5-ylmethyl}-methylthiocarbamide;
(S)-N-{3-[4-(4-cyanomethylidene-3,3-dimethylpiperidin-1-yl)-3-fluorophenyl]-2-oxo-oxazolidin-5-ylmethyl}-acetamide;
(R)-{3-[4-(4-cyanomethylidene-3,3-dimethylpiperidin-1-yl)-3-fluorophenyl]-2-oxo-oxazolidin-5-ylmethyl}-methanesulphonate;
(S)-N-{3-[4-(4-(1-cyanoethylidene)-piperidin-1-yl)-phenyl]-2-oxo-oxazolidin-5-ylmethyl}-acetamide;
(S)-N-{3-[4-(4-(1-cyanoethylidene)-piperidin-1-yl)-3-fluorophenyl]-2-oxo-oxazolidin-5-ylmethyl}-formamide;
(S)-N-{3-[4-(4-(1-cyanoethylidene)-piperidin-1-yl)-3-fluorophenyl]-2-oxo-oxazolidin-5-ylmethyl}-acetamide;
(S)-N-{3-[4-(4-(1-cyanoethylidene)-piperidin-1-yl)-3-fluorophenyl]-2-oxo-oxazolidin-5-ylmethyl}-2-cyanoacetamide;
(S)-N-{3-[4-(4-(1-cyanoethylidene)-piperidin-1-yl)-3-fluorophenyl]-2-oxo-oxazolidin-5-ylmethylamino}-carboxymethylamine;
(S)-N-{3-[4-(4-(1-cyanoethylidene)-piperidin-1-yl)-3-fluorophenyl]-2-oxo-oxazolidin-5-ylmethyl}-difluoroacetamide;
(S)-N-{3-[4-(4-(1-cyanoethylidene)-piperidin-1-yl)-3-fluorophenyl]-2-oxo-oxazolidin-5-ylmethyl}-chloroacetamide;
(S)-N-{3-[4-(4-(1-cyanoethylidene)-piperidin-1-yl)-3-fluorophenyl]-2-oxo-oxazolidin-5-ylmethyl}-dichloroacetamide;

(S)-N-{3-[4-(4-(1-cyanoethylidene)-piperidin-1-yl)-3-fluorophenyl]-2-oxo-oxazolidin-5-ylmethyl}-trichloroacetamide;
(S)-N-{3-[4-(4-(1-cyanoethylidene)-piperidin-1-yl)-3-fluorophenyl]-2-oxo-oxazolidin-5-ylmethyl}-isobutyl-carbamate;
(R)-{3-[4-(4-(1-cyanoethylidene)-piperidin-1-yl)-3-fluorophenyl]-2-oxo-oxazolidin-5-ylmethyl}-alcohol;
(S)-N-{3-[4-(4-(1-cyanoethylidene)-piperidin-1-yl)-3-fluorophenyl]-2-oxo-oxazolidin-5-ylmethyl}-thioacetamide;
E/Z mixture of (S)-N-{3-[4-(4-(1-cyanoethylidene)-3-fluoropiperidin-1-yl)-3-fluorophenyl]-2-oxo-oxazolidin-5-ylmethyl}-acetamide;
E-(S)-N-{3-[4-(4-(1-cyanoethylidene)-3-fluoropiperidin-1-yl)-3-fluorophenyl]-2-oxo-oxazolidin-5-ylmethyl}-acetamide;
Z-(S)-N-{3-[4-(4-(1-cyanoethylidene)-3-fluoropiperidin-1-yl)-3-fluorophenyl]-2-oxo-oxazolidin-5-ylmethyl}-acetamide;
(S)-N-{3-[4-(4-(1-cyanopropylidene)-piperidin-1-yl)-phenyl]-2-oxo-oxazolidin-5-ylmethyl}-acetamide;
(S)-N-{3-[4-(4-(1-cyanopropylidene)-piperidin-1-yl)-3-fluorophenyl]-2-oxo-oxazolidin-5-ylmethyl}-acetamide;
(S)-N-{3-[4-(4-(1-cyanopropylidene)-piperidin-1-yl)-3-fluorophenyl]-2-oxo-oxazolidin-5-ylmethyl}-dichloroacetamide;
(S)-N-{3-[4-(4-(1-cyanopropylidene)-piperidin-1-yl)-3-fluorophenyl]-2-oxo-oxazolidin-5-ylmethyl}-trichloroacetamide;
(S)-N-{3-[4-(4-(1-cyanopropylidene)-piperidin-1-yl)-3-fluorophenyl]-2-oxo-oxazolidin-5-ylmethyl}-bromoacetamide;
(S)-N-{3-[4-(4-(1-cyanopropylidene)-piperidin-1-yl)-3-fluorophenyl]-2-oxo-oxazolidin-5-ylmethyl}-thioacetamide;
(S)-N-{3-[4-(4-(1-cyano-cyclopropylmethylidene)-piperidin-1-yl)-3-fluorophenyl]-2-oxo-oxoazolidin-5-ylmethyl}-acetamide;
(S)-N-{3-[4-(4-(1-cyano-3-ene-butylidene)-piperidin-1-yl)-3-fluorophenyl]-2-oxo-oxazolidin-5-ylmethyl}-acetamide;
(S)-N-{3-[4-(4-(1-cyano-3-yne-butylidene)-piperidin-1-yl)-3-fluorophenyl]-2-oxo-oxazolidin-5-ylmethyl}-acetamide;
(S)-N-{3-[4-(4-(1-cyano-2-phenyl-ethylidene)-piperidin-1-yl)-3-fluorophenyl]-2-oxo-oxazolidin-5-ylmethyl}-acetamide;
(S)-N-{3-[4-(4-(1-cyano-1-phenyl-methylidene)-piperidin-1-yl)-3-fluorophenyl]-2-oxo-oxazolidin-5-ylmethyl}-acetamide;
(S)-N-{3-[4-(4-(1-cyano-1-(3,4-difluorophenyl)-methylidene)-piperidin-1-yl)-3-fluorophenyl]-2-oxo-oxazolidin-5-ylmethyl}-acetamide;
(S)-N-{3-[4-(4-(1,1-dicyano-methylidene)-piperidin-1-yl)-3-fluorophenyl]-2-oxo-oxazolidin-5-ylmethyl}-acetamide;
(S)-N-{3-[4-(4-(1-cyano-1-carboxamido-methylidene)-piperidin-1-yl)-3-fluorophenyl]-2-oxo-oxazolidin-5-ylmethyl}-acetamide;
(S)-N-{3-[4-(4-(1-cyano-1-(N-prop-2-ene-carboxamido)-methylidene)-piperidin-1-yl)-3-fluorophenyl]-2-oxo-oxazolidin-5-ylmethyl}-acetamide;
(S)-N-{3-[4-(4-(1-cyano-1-(N-cyclopropyl-carboxamido)-methylidene)-piperidin-1-yl)-3-fluorophenyl]-2-oxo-oxazolidin-5-ylmethyl}-acetamide;
(S)-N-{3-[4-(4-(1-cyano-1-(N-cyclohexyl-carboxamido)-methylidene)-piperidin-1-yl)-3-fluorophenyl]-2-oxo-oxazolidin-5-ylmethyl}-acetamide;
(S)-N-{3-[4-(4-(1-cyano-3-hydroxy-propylidene)-piperidin-1-yl)-3-fluorophenyl]-2-oxo-oxazolidin-5-ylmethyl}-acetamide;
(S)-N-{3-[4-(4-(1-cyano-1-ethoxycarbonyl-methylidene)-piperidin-1-yl)-3-fluorophenyl]-2-oxo-oxazolidin-5-ylmethyl}-acetamide;
(S)-N-{3-[4-(4-(1-cyano-1-methylmercapto-methylidene)-piperidin-1-yl)-3-fluorophenyl]-2-oxo-oxazolidin-5-ylmethyl}-acetamide;
(S)-N-{3-[4-(4-(1-cyano-1-phenylmercapto-methylidene)-piperidin-1-yl)-3-fluorophenyl]-2-oxo-oxazolidin-5-ylmethyl}-acetamide;
(S)-N-{3-[4-(4-(1-cyano-1-bromo-methylidene)-piperidin-1-yl)-3-fluorophenyl]-2-oxo-oxazolidin-5-ylmethyl}-acetamide;
(S)-N-{3-[4-(4-(1,1-dicyano-methylidene)-piperidin-1-yl)-3-fluorophenyl]-2-oxo-oxazolidin-5-ylmethyl}-thioacetamide;
(S)-N-{3-[4-(4-(1-cyano-1-ethoxycarbonyl-methylidene)-piperidin-1-yl)-3-fluorophenyl]-2-oxo-oxazolidin-5-ylmethyl}-thioacetamide;
(S)-{3-[4-(4-cyanomethyl-piperidin-1-yl)-phenyl]-2-oxo-oxazolidin-5-ylmethyl}-azide;
(R)-{3-[4-(4-cyanomethyl-piperidin-1-yl)-phenyl]-2-oxo-oxazolidin-5-ylmethyl}-alcohol;
(R)-{3-[4-(4-cyanomethyl-piperidin-1-yl)-phenyl]-2-oxo-oxazolidin-5-ylmethyl}-methanesulphonate;
(S)-N-{3-[4-(4-cyanomethyl-piperidin-1-yl)-phenyl]-2-oxo-oxazolidin-5-ylmethyl}-thioacetamide;
(S)-N-{3-[4-(4-cyanomethyl-piperidin-1-yl)-3-fluorophenyl]-2-oxo-oxazolidin-5-ylmethyl}-thioacetamide;
(S)-N-{3-[4-(4-cyanomethyl-3-fluoropiperidin-1-yl)-phenyl]-2-oxo-oxazolidin-5-ylmethyl}-thioacetamide;
(R)-{3-[4-(4-cyanomethyl-3-fluoropiperidin-1-yl)-phenyl]-2-oxo-oxazolidin-5-ylmethyl}-alcohol;
(R)-{3-[4-(4-cyanomethyl-3-fluoropiperidin-1-yl)-phenyl]-2-oxo-oxazolidin-5-ylmethyl}-methanesulphonate;
(S)-N-{3-[4-(4-(1-cyano-1-benzyl)-methylpiperidin-1-yl)-3-fluorophenyl]-2-oxo-oxazolidin-5-ylmethyl}-acetamide;
(S)-N-{3-[4-(4-(1-cyano-2-methanesulphonyloxy)-ethylpiperidin-1-yl)-3-fluorophenyl]-2-oxo-oxazolidin-5-ylmethyl}-acetamide;
(S)-N-{3-[4-(4-(1-cyano-1-(3,4-difluorophenyl))-methylpiperidin-1-yl)-3-fluorophenyl]-2-oxo-oxazolidin-5-ylmethyl}-acetamide;
(S)-N-{3-[4-(4-(1-cyano-1-carboxamido)-methylpiperidin-1-yl)-3-fluorophenyl]-2-oxo-oxazolidin-5-ylmethyl}-acetamide;
(S)-N-{3-[4-(4-(1-cyano-1-cyclohexylaminocarbonyl)-methylpiperidin-1-yl)-3-fluorophenyl]-2-oxo-oxazolidin-5-ylmethyl}-acetamide;
(S)-N-{3-[4-(4-(1-cyano-1-ethoxycarbonyl)-methylpiperidin-1-yl)-3-fluorophenyl]-2-oxo-oxazolidin-5-ylmethyl}-acetamide;
(S)-N-{3-[4-(4-(1-cyano-1-(phenylmercapto))-methylpiperidin-1-yl)-3-fluorophenyl]-2-oxo-oxazolidin-5-ylmethyl}-acetamide;
(S)-N-{3-[4-(4-(1-cyano-1-ethoxycarbonyl)-methylpiperidin-1-yl)-3-fluorophenyl]-2-oxo-oxazolidin-5-ylmethyl}-thioacetamide;

(S)-N-{3-[4-(4-(1-cyano-1-carboxamido)-methylpiperidin-1-yl)-3-fluorophenyl]-2-oxo-oxazolidin-5-ylmethyl}-thioacetamide;

(S)-N-{3-[4-(4-(1-cyano-1-thiocarboxamido)-methylpiperidin-1-yl)-3-fluorophenyl]-2-oxo-oxazolidin-5-ylmethyl}-thioacetamide;

(R)-{3-[4-(4-(1-cyano-2-hydroxy)-ethylpiperidin-1-yl)-3-fluorophenyl]-2-oxo-oxazolidin-5-ylmethyl}-methanesulphonate;

(R)-{3-[4-(4-(1-cyano-1-hydroxycarbonyl)-methylpiperidin-1-yl)-3-fluorophenyl]-2-oxo-oxazolidin-5-ylmethyl}-methanesulphonate;

(R)-{3-[4-(4-(1-cyano-1-ethoxycarbonyl)-methylpiperidin-1-yl)-3-fluorophenyl]-2-oxo-oxazolidin-5-ylmethyl}-methanesulphonate;

(R)-{3-[4-(4-(1-cyano-1-carboxamido)-methylpiperidin-1-yl)-3-fluorophenyl]-2-oxo-oxazolidin-5-ylmethyl}-methanesulphonate;

(S)-N-{3-[4-(4-cyanomethyl-3,4-dehydropiperidin-1-yl)-3-fluorophenyl]-2-oxo-oxazolidin-5-ylmethyl}-acetamide;

(S)-N-{3-[4-(4-cyanomethyl-3,4-dehydropiperidin-1-yl)-3-fluorophenyl]-2-oxo-oxazolidin-5-ylmethyl}-thioacetamide;

(S)-N-{3-[4-(4-cyanomethyl-3-methyl-4,5-dehydropiperidin-1-yl)-3-fluorophenyl]-2-oxo-oxazolidin-5-ylmethyl}-acetamide;

(S)-N-{3-[4-(4-cyanomethyl-3-fluoro-4,5-dehydropiperidin-1-yl)-3-fluorophenyl]-2-oxo-oxazolidin-5-ylmethyl}-acetamide; and (S)-N-{3-[4-(4-cyanomethyl-3-fluoro-4,5-dehydropiperidin-1-yl)-3-fluorophenyl]-2-oxo-oxazolidin-5-ylmethyl}-isobutylcarbamate.

6. A compound selected from the group consisting of:

(S)-N-{3-[4-(4-cyanomethylidene-piperidin-1-yl)-phenyl]-2-oxo-oxazolidin-5-ylmethyl}-acetamide;

(S)-N-{3-[4-(4-cyanomethylidene-piperidin-1-yl)-3-fluorophenyl]-2-oxo-oxazolidin-5-ylmethyl}-acetamide;

(S)-N-{3-[4-(4-cyanomethylidene-piperidin-1-yl)-3-fluorophenyl]-2-oxo-oxazolidin-5-ylmethyl}-2-cyanoacetamide;

(S)-N-{3-[4-(4-cyanomethylidene-piperidin-1-yl)-3-fluorophenyl]-2-oxo-oxazolidin-5-ylmethyl}-trifluoroacetamide;

(S)-N-{3-[4-(4-cyanomethylidene-piperidin-1-yl)-3-fluorophenyl]-2-oxo-oxazolidin-5-ylmethyl}-chloroacetamide;

(S)-N-{3-[4-(4-cyanomethylidene-piperidin-1-yl)-3-fluorophenyl]-2-oxo-oxazolidin-5-ylmethyl}-dichloroacetamide;

(S)-N-{3-[4-(4-cyanomethylidene-piperidin-1-yl)-3-fluorophenyl]-2-oxo-oxazolidin-5-ylmethyl}-thioacetamide;

(S)-N-{3-[4-(4-cyanomethylidene-piperidin-1-yl)-3-fluorophenyl]-2-oxo-oxazolidin-5-ylmethyl}-methylthiocarbamate;

(S)-N-{3-[4-(4-cyanomethylidene-piperidin-1-yl)-3-fluorophenyl]-2-oxo-oxazolidin-5-ylmethyl}-2-hydroxythioacetamide;

(S)-N-{3-[4-(4-cyanomethylidene-piperidin-1-yl)-3-fluorophenyl]-2-oxo-oxazolidin-5-ylmethyl}-thiocarbamide;

E-(S)-N-{3-[4-(4-cyanomethylidene-3-fluoropiperidin-1-yl)-3-fluorophenyl]-2-oxo-oxazolidin-5-ylmethyl}-acetamide;

Z-(S)-N-{3-[4-(4-cyanomethylidene-3-fluoropiperidin-1-yl)-3-fluorophenyl]-2-oxo-oxazolidin-5-ylmethyl}-acetamide;

(S)-N-{3-[4-(4-cyanomethylidene-3-fluoropiperidin-1-yl)-3-fluorophenyl]-2-oxo-oxazolidin-5-ylmethyl}-difluoroacetamide;

(S)-N-{3-[4-(4-cyanomethylidene-3-fluoropiperidin-1-yl)-3-fluorophenyl]-2-oxo-oxazolidin-5-ylmethyl}-thioacetamide;

(S)-N-{3-[4-(4-cyanomethylidene-3-methylpiperidin-1-yl)-3-fluorophenyl]-2-oxo-oxazolidin-5-ylmethyl}-thiocarbamide;

(S)-N-{3-[4-(4-cyanomethylidene-3-methylpiperidin-1-yl)-3-fluorophenyl]-2-oxo-oxazolidin-5-ylmethyl}-methylthiocarbamide;

(S)-N-{3-[4-(4-(1-cyanoethylidene)-piperidin-1-yl)-3-fluorophenyl]-2-oxo-oxazolidin-5-ylmethyl}-acetamide;

(S)-N-{3-[4-(4-(1-cyanoethylidene)-piperidin-1-yl)-3-fluorophenyl]-2-oxo-oxazolidin-5-ylmethyl}-difluoroacetamide;

(S)-N-{3-[4-(4-(1-cyanoethylidene)-piperidin-1-yl)-3-fluorophenyl]-2-oxo-oxazolidin-5-ylmethyl}-dichloroacetamide;

(S)-N-{3-[4-(4-(1-cyanoethylidene)-piperidin-1-yl)-3-fluorophenyl]-2-oxo-oxazolidin-5-ylmethyl}-thioacetamide;

(S)-N-{3-[4-(4-(1-cyanopropylidene)-piperidin-1-yl)-3-fluorophenyl]-2-oxo-oxazolidin-5-ylmethyl}-acetamide;

(S)-N-{3-[4-(4-(1-cyanopropylidene)-piperidin-1-yl)-3-fluorophenyl]-2-oxo-oxazolidin-5-ylmethyl}-dichloroacetamide;

(S)-N-{3-[4-(4-(1-cyanopropylidene)-piperidin-1-yl)-3-fluorophenyl]-2-oxo-oxazolidin-5-ylmethyl}-thioacetamide;

(S)-N-{3-[4-(4-(1-cyano-3-yne-butylidene)-piperidin-1-yl)-3-fluorophenyl]-2-oxo-oxazolidin-5-ylmethyl}-acetamide;

(S)-N-{3-[4-(4-(1-cyano-1-(thiophen-2-yl)-methylidene)-piperidin-1-yl)-3-fluorophenyl]-2-oxo-oxazolidin-5-ylmethyl}-acetamide;

(S)-N-{3-[4-(4-(1-cyano-1-methylmercapto-methylidene)-piperidin-1-yl)-3-fluorophenyl]-2oxo-oxazolidin-5-ylmethyl}-acetamide;

(S)-N-{3-[4-(4-(1-cyano-1-bromo-methylidene)-piperidin-1-yl)-3-fluorophenyl]-2-oxo-oxazolidin-5-ylmethyl}-acetamide;

(S)-N-{3-[4-(4-(1,1-dicyano-methylidene)-piperidin-1-yl)-3-fluorophenyl]-2-oxo-oxazolidin-5-ylmethyl}-thioacetamide;

(S)-N-{3-[4-(4-(1-cyano-1-ethoxycarbonyl-methylidene)-piperidin-1-yl)-3-fluorophenyl]-2-oxo-oxazolidin-5-ylmethyl}-thioacetamide;

(S)-N-{3-[4-(4-cyanomethyl-3,4-dehydropiperidin-1-yl)-3-fluorophenyl]-2-oxo-oxazolidin-5-ylmethyl}-acetamide;

(S)-N-{3-[4-(4-cyanomethyl-3,4-dehydropiperidin-1-yl)-3-fluorophenyl]-2-oxo-oxazolidin-5-ylmethyl}-thioacetamide; and (S)-N-{3-[4-(4-cyanomethyl-3-fluoro-4,5-dehydropiperidin-1-yl)-3-fluorophenyl]-2-oxo-oxazolidin-5-ylmethyl}-acetamide.

7. A composition comprising a compound according to claim 1, and an excipient, diluent, solvent or carrier.

8. A composition comprising a compound according to claim 2, and an excipient, diluent, solvent or carrier.

9. A composition comprising a compound according to claim 3, and an excipient, diluent, solvent or carrier.

10. A composition comprising a compound according to claim 4, and an excipient, diluent, solvent or carrier.

11. A composition comprising a compound according to claim 5, and an excipient, diluent, solvent or carrier.

12. A composition comprising a compound according to claim 6, and an excipient, diluent, solvent or carrier.

* * * * *